United States Patent
Kusters et al.

(10) Patent No.: US 10,207,042 B2
(45) Date of Patent: Feb. 19, 2019

(54) MEMBRANE SEPARATION DEVICES, SYSTEMS AND METHODS EMPLOYING SAME, AND DATA MANAGEMENT SYSTEMS AND METHODS

(71) Applicant: Fenwal, Inc., Lake Zurich, IL (US)

(72) Inventors: Benjamin Kusters, Racine, WI (US); Kyungyoon Min, Kildeer, IL (US); Christopher Wegener, Libertyville, IL (US)

(73) Assignee: Fenwal, Inc., Lake Zurich, IL (US)

( * ) Notice: Subject to any disclaimer, the term of this patent is extended or adjusted under 35 U.S.C. 154(b) by 422 days.

(21) Appl. No.: 15/066,047

(22) Filed: Mar. 10, 2016

(65) Prior Publication Data
US 2016/0184504 A1    Jun. 30, 2016

Related U.S. Application Data

(63) Continuation of application No. 14/422,032, filed as application No. PCT/US2013/030111 on Mar. 11, 2013, now Pat. No. 9,388,383.
(Continued)

(51) Int. Cl.
*A61M 1/34* (2006.01)
*A61M 1/26* (2006.01)
(Continued)

(52) U.S. Cl.
CPC ......... *A61M 1/3496* (2013.01); *A01N 1/0242* (2013.01); *A61M 1/0272* (2013.01);
(Continued)

(58) Field of Classification Search
CPC ........ A61M 1/26; A61M 1/262; A61M 1/265; A61M 1/3496; A61M 1/0272;
(Continued)

(56) References Cited

U.S. PATENT DOCUMENTS

| | | | | |
|---|---|---|---|---|
| 5,034,135 A | * | 7/1991 | Fischel | A61M 1/30 210/321.68 |
| 5,298,016 A | | 3/1994 | Gordon | |

(Continued)

FOREIGN PATENT DOCUMENTS

| | | |
|---|---|---|
| EP | 0310205 A2 | 4/1989 |
| EP | 0531540 A1 | 3/1993 |

(Continued)

OTHER PUBLICATIONS

PCT International Search Report for International Application No. PCT/US2013/030111 filed Mar. 11, 2013 for Applicant Fenwal, Inc. dated Sep. 25, 2013, 7 pages.

(Continued)

*Primary Examiner* — Pranav N Patel
(74) *Attorney, Agent, or Firm* — Cook Alex Ltd

(57) ABSTRACT

A membrane separation device is disclosed along with systems and methods employing the device in blood processing procedures. In one embodiment, a spinning membrane separator is provided in which at least two zones or regions are created in the gap between the spinning membrane and the shell, such that mixing of the fluid between the two regions is inhibited by a radial rib or ridge associated with the spinning membrane that decreases the gap between the spinning membrane and the shell to define two fluid regions, the ridge isolating the fluid in the two regions to minimize mixing between the two. Automated systems and methods are disclosed for separating a unit of previously-collected whole blood into selected blood components, such as concentrated red cells and plasma, for collecting red cells and plasma directly from a donor in a single pass, and for cell washing. Data management systems and methods and priming methods are also disclosed.

11 Claims, 62 Drawing Sheets

Related U.S. Application Data

(60) Provisional application No. 61/698,974, filed on Sep. 10, 2012, provisional application No. 61/699,006, filed on Sep. 10, 2012, provisional application No. 61/699,067, filed on Sep. 10, 2012, provisional application No. 61/699,046, filed on Sep. 10, 2012, provisional application No. 61/699,015, filed on Sep. 10, 2012.

(51) Int. Cl.
*A61M 1/36* (2006.01)
*A61M 1/02* (2006.01)
*B01D 61/18* (2006.01)
*B01D 63/16* (2006.01)
*C12N 5/078* (2010.01)
*A01N 1/02* (2006.01)

(52) U.S. Cl.
CPC ............ *A61M 1/265* (2014.02); *A61M 1/342* (2013.01); *A61M 1/3635* (2014.02); *A61M 1/3643* (2013.01); *A61M 1/3644* (2014.02); *A61M 1/3649* (2014.02); *A61M 1/3672* (2013.01); *B01D 61/18* (2013.01); *B01D 63/16* (2013.01); *C12N 5/0641* (2013.01); *A61M 2202/0429* (2013.01); *A61M 2202/0439* (2013.01); *A61M 2205/6072* (2013.01); *A61M 2205/7554* (2013.01); *B01D 2313/08* (2013.01); *B01D 2313/20* (2013.01); *B01D 2313/243* (2013.01); *B01D 2315/02* (2013.01)

(58) Field of Classification Search
CPC .. A61M 1/342; A61M 1/3635; A61M 1/3643; A61M 1/3649; A61M 1/3672; A61M 1/34; A61M 1/3403; A61M 1/38; B01D 2313/08; B01D 2313/20; B01D 2313/243; B01D 2315/02; B01D 61/18; B01D 63/16; B01D 2221/10
See application file for complete search history.

(56) References Cited

U.S. PATENT DOCUMENTS

| | | | |
|---|---|---|---|
| 5,460,715 A * | 10/1995 | Kawamura | A61M 1/3472 210/108 |
| 6,527,957 B1 | 3/2003 | Deniega et al. | |
| 6,582,386 B2 | 6/2003 | Min | |
| 7,651,474 B2 | 1/2010 | Van Waeg | |
| 9,279,104 B2 | 3/2016 | Kusters et al. | |
| 2004/0186408 A1* | 9/2004 | Behague | A61M 1/0272 604/4.01 |
| 2012/0220915 A1 | 8/2012 | Wegener et al. | |
| 2012/0282234 A1 | 11/2012 | Min | |

FOREIGN PATENT DOCUMENTS

| | | |
|---|---|---|
| EP | 1484390 A1 | 12/2004 |
| EP | 1867353 A1 | 12/2007 |
| WO | WO 88/01193 A1 | 2/1988 |
| WO | WO 99/26678 A1 | 6/1999 |
| WO | WO 99/32211 A1 | 7/1999 |
| WO | WO 01/17652 A1 | 3/2001 |
| WO | WO 2011/091281 A2 | 7/2011 |

OTHER PUBLICATIONS

PCT Written Opinion of the International Searching Authority for PCT/US2013/030111 filed Mar. 11, 2013 dated Oct. 1, 2013, 14 pages.

* cited by examiner

MEMBRANE SEPARATION DEVICES, SYSTEMS AND METHODS EMPLOYING SAME, AND DATA MANAGEMENT SYSTEMS AND METHODS

FIELD OF THE DISCLOSURE

The present application is related, in part, to separation devices of the type employing relatively rotating surfaces, at least one of which carries a membrane for filtering a component from fluid passed between the surfaces; to fluid flow circuits and systems incorporating such a separator; and to the use of such systems to separate biological cells, such as red cells, plasma or white cells, from whole blood, a storage medium, a suspension medium, a supernatant, or the like.

BACKGROUND

Traditional blood collection continues to rely heavily on manual collection of whole blood from healthy donors through blood drives, from donor visits to blood centers or hospitals and the like. In typical manual collection, whole blood is collected by simply flowing it, under the force of gravity and venous pressure, from the vein of the donor into a collection container. The amount of whole blood drawn is typically a "unit," which is about 450 ml.

More specifically, such a collection typically employs a pre-assembled arrangement of tubing and containers or bags, including a flexible plastic primary container or bag for receiving a unit of whole blood from a donor and one or more "satellite" containers or bags. The blood is first collected in the primary container, which also contains an anticoagulant (typically containing sodium citrate, phosphate and dextrose—often referred to as CPD). A preservative (often called an "additive solution" or AS, and commonly containing a saline, adenine and glucose medium—which is referred to as SAG) may be included as part of a larger assembly of bags and tubes that are used in processing after the blood is collected.

After collection of a unit of whole blood, it is common practice in blood banking to transport the unit of whole blood, with connected tubing and containers, to a blood component processing laboratory, commonly referred to as a "back lab," for further processing. Further processing usually entails manually loading the primary container and associated tubing and satellite containers into a centrifuge to separate the whole blood into components such as concentrated red cells and platelet-rich or platelet-poor plasma. These components are then manually expressed from the primary container into other pre-connected satellite containers, and may be again centrifuged to separate the platelets from plasma. Subsequently, the blood components may be leukoreduced by filtration for further processing or storage. In short, this process is time consuming, labor intensive, and subject to possible human error.

Another routine task performed by blood banks and transfusion center is "cell washing." This may be performed to remove and/or replace the liquid medium (or a part thereof) in which the cells are suspended, to concentrate or further concentrate cells in a liquid medium, and/or to purify a cell suspension by the removal of unwanted cellular or other material.

Previous cell washing systems most typically involved centrifugation of a cell-suspension, decanting of the supernatant, re-suspension of concentrated cells in new media, and possible repetition of these steps until the cells of the suspension are provided at an adequately high or otherwise desirable concentration. Centrifugal separators used in the processing of blood and blood components have commonly been used in such cell-washing methods.

These processes are also quite time consuming, requiring repeated manual manipulation of the blood or blood components and assembly or disassembly of various fluid processing apparatus. This, of course, increases not only the costs, but the potential for human error or mistake. Accordingly, despite decades of advancement in blood separation devices and processes, there continues to be a desire for better and/or more efficient separation devices, systems and methods applicable to basic blood collection and processing modalities.

While many of the prior blood separation apparatus and procedures have employed centrifugal separation principles, there is another class of devices, based on the use of a membrane, that has been used for plasmapheresis, that is separating plasma from whole blood. More specifically, this type of device employs relatively rotating surfaces, at least one or which carries a porous membrane. Typically the device employs an outer stationary housing and an internal spinning rotor covered by a porous membrane.

One such well-known plasmapheresis device is the Autopheresis-C® separator sold by Fenwal, Inc. of Lake Zurich, Ill. A detailed description of a spinning membrane separator may be found in U.S. Pat. No. 5,194,145 to Schoendorfer, which is incorporated by reference herein. This patent describes a membrane-covered spinner having an interior collection system disposed within a stationary shell. Blood is fed into an annular space or gap between the spinner and the shell. The blood moves along the longitudinal axis of the shell toward an exit region, with plasma passing through the membrane and out of the shell into a collection bag. The remaining blood components, primarily red blood cells, platelets and white cells, move to the exit region between the spinner and the shell and then are typically returned to the donor.

Spinning membrane separators have been found to provide excellent plasma filtration rates, due primarily to the unique flow patterns ("Taylor vortices") induced in the gap between the spinning membrane and the shell. The Taylor vortices help to keep the blood cells from depositing on and fouling or clogging the membrane.

While spinning membrane separators have been widely used for the collection of plasma, they have not typically been used for the collection of other blood components, specifically red blood cells. Spinning membrane separators also have not typically been used for cell washing. One example of a spinning membrane separator used in the washing of cells such as red blood cells is described in U.S. Pat. No. 5,053,121 which is also incorporated by reference in its entirety. However, the system described therein utilizes two separate spinners associated in series or in parallel to wash "shed" blood of a patient. Other descriptions of the use of spinning membrane separators for separation of blood or blood components may also be found in U.S. Pat. Nos. 5,376,263; 4,776,964; 4,753,729; 5,135,667 and 4,755,300.

The subject matter disclosed herein provides further advances in membrane separators, potential cost reduction and various other advances and advantages over the prior manual collection and processing of blood.

SUMMARY OF THE DISCLOSURE

The present subject matter has a number of aspects which may be used in various combinations, and the disclosure of one or more specific embodiments is for the purpose of disclosure and description, and not limitation. This summary highlights only a few of the aspects of this subject matter, and additional aspects are disclosed in the drawings and the more detailed description that follows.

In accordance with one aspect of the disclosure, an automated whole blood separation system is provided that comprises a disposable fluid flow circuit module and a durable controller module that is configured to cooperate with and control fluid flow through the fluid circuit. The disposable fluid circuit includes a whole blood fluid flow path with a whole blood inlet for connection to a unit of whole blood, such as the primary container of whole blood previously collected from a donor, and a cell preservation solution flow path with an inlet for connection to a source of cell preservation solution, such as Adsol® solution, available from Fenwal, Inc. of Lake Zurich Ill., USA.

The disposable fluid circuit also includes a separator with an outer housing, such as a generally cylindrical outer housing, and an inner rotor mounted within the housing for rotation relative to the housing. A gap is defined between an outer surface of the rotor and an inner surface of the housing and at least one of the surfaces comprises a filter membrane configured to allow the passage of plasma through the membrane while substantially blocking red blood cells. The outer housing has an inlet that is in fluid communication with the whole blood and/or cell preservation solution flow paths and is also in flow communication with the gap between the housing and the rotor, for directing whole blood and/or cell preservation solution into the gap. The housing includes a first outlet communicating with the gap for withdrawing a blood component such as concentrated red cells and the housing and/or rotor includes a second outlet communicating with the side of the membrane facing away from the gap for collecting a blood component that passes through the membrane, such as plasma. The housing is configured to have a top and a bottom, with the inlet located proximate to the bottom of the housing and the first and second outlets located proximate to the top of the housing. The first housing outlet communicating with the gap is in flow communication with an outlet fluid flow path for connection to a storage container, such as a red cell storage container and, optionally, a leukocyte reduction filter.

The durable controller of the system may include a programmable control system for controlling processing of whole blood through the fluid circuit and, if desired, for controlling the rotational speed of the separator rotor, and/or any associated pumps and/or clamps for controlling flow rates of fluid through the fluid circuit.

For example, the durable controller may include an inlet pump configured to control fluid flow through the whole blood and/or cell preservative solution flow paths and an outlet pump configured to control fluid flow through the housing outlet that communicates with the gap. As noted above, these may be controlled by a programmable control system of the durable controller. The controller may also include a hematocrit detector that cooperates with the whole blood flow path for measuring hematocrit of the blood flowing through the whole blood path and other valves, pumps and sensors, as desired.

The fluid circuit may also include a leukocyte reduction filter in flow communication with a separator outlet fluid flow path, for example, for removing leukocytes from concentrated red cells collected by the separator. The leukocyte reduction filter may also reduce the number platelets contained with the red cells. The durable controller control system may be programmed to prime the fluid circuit with cell preservation solution before processing whole blood and, if desired, to flush the fluid circuit of whole blood and/or red cells after substantially all the whole blood is processed, in order to increase the efficiency or maximize the collection of red cells from the unit of whole blood.

As described in more detail below, the durable controller may also include a drive unit for causing relative rotation between the house and the rotor to create Taylor-Couette flow conditions in the gap between rotor and housing. More specifically, the relative rotational speeds and the width of the gap between the facing surfaces of the rotor and housing may be such as to create Taylor vortices in the gap, which vortices act to continuously sweep the membrane free of accumulated cells, allowing increased flow of plasma through the membrane and, consequently, reduce processing time for processing a unit of whole blood.

Further, in connection with the subject matter described herein a pre-assembled disposable fluid flow circuit is described for separating whole blood into a plasma component and a concentrated red component. The fluid flow circuit, is preferably pre-assembled and pre-sterilized, and includes a whole blood fluid flow path with a whole blood inlet for connection to a container containing a collected unit of whole blood, and a cell preservation solution flow path with an inlet for connection to a source of cell preservation solution, such as Adsol® solution referred to earlier. The fluid circuit includes a separator with an outer housing and an inner rotor mounted within the housing for rotation relative to the housing, with a gap defined between the outer surface of the rotor and an inner surface of the housing. At least one of the inner or outer surfaces of the housing and rotor, respectfully, comprises a filter membrane configured to allow passage of plasma therethrough while substantially blocking red cells. The outer housing includes an inlet in fluid communication with the whole blood and/or cell preservation solution flow paths and in flow communication with the gap between the interior rotor and the outer housing, for directing whole blood and/or cell preservation solutions into the gap. The housing includes a first outlet communicating with the gap, for example, for removing concentrated red cells from the gap. The housing and/or the rotor also may include a second outlet communicating with the side of membrane facing away from the gap for collecting fluid that passes through the membrane, such as plasma. The first and second outlets are proximate to a top portion of the housing and/or rotor, while the inlet is proximate to a bottom portion of the housing. Further, the first housing outlet that communicates with the gap is preferably in flow communication with an outlet fluid flow path for connection to a red cell storage container which may be pre-assembled and pre-attached to the rest of the fluid circuit if desired.

Further, the pre-assembled disposable fluid flow circuit may include a leukocyte reduction filter in flow communication with the outlet fluid flow path, for reduction of leukocytes in the concentrated red cells. If desired, a leukocyte reduction filter could also be provided in a flow path communicating with a side of the membrane facing away from the gap for filtering fluid passing through the membranes, such as plasma. Optionally the pre-assembled disposable fluid circuit may also include a pre-attached container of red cell or other cell preservation solution, such as a Fenwal Adsol® solution.

In another aspect of the disclosure, a disposable fluid circuit configured to interface with a hardware component to form an automated blood collection system for collecting red blood cells and plasma from a donor comprising is provided. The disposable component includes a donor access device for withdrawing whole blood from a donor, with a whole blood collection container in communication with the donor access device for receipt of whole blood from a donor. The circuit further includes a blood separation device communicating with the whole blood collection container and employing relatively rotating surfaces, with at least one of the surfaces carrying a membrane substantially permeable to plasma and substantially impermeable to red blood cells to separate the whole blood into substantially concentrated red cells and plasma. A first collection container is provided that communicates with the blood separation chamber for receipt of the substantially concentrated red blood cells, with a source of preservative solution communicating with the first collection container. A second collection container communicating with the blood separation chamber is provided for receipt of the plasma.

In another aspect, the disposable fluid circuit includes a leukocyte filter communicating with the first collection container. Further, the source of the preservative solution and the whole blood collection container and donor access device may either be formed integrally with the fluid circuit, or formed separately from the fluid circuit and are configured to be attached thereto.

In a further aspect of the disclosure, a method for collecting red blood cells using a spinning membrane separation device is provided in which an increased volume of red blood cells may be collected. Pursuant to the method, a first quantity of whole blood is withdrawn from the donor. The first quantity of whole blood is then separated into a first quantity of red blood cells and a first quantity of plasma using the spinning membrane separator. The first quantity of separated red blood cells and the first quantity of separated plasma are then flowed to respective collection containers. Then, at least a portion of the first quantity of separated plasma is returned to the donor. Optionally, the whole blood may be flowed into a processing container before being flowed to the spinning membrane separation device so as to permit the return of plasma to the donor simultaneously with the separation of whole blood into red blood cells and plasma. A second quantity of whole blood is then withdrawn from the donor and separated into a second quantity of red blood cells and a second quantity of plasma using the spinning membrane separator. The second quantities of red blood cells and plasma are flowed to the respective collection containers, and at least a portion of the second quantity of red blood cells, and at least a portion of the second quantity of plasma is returned to the donor In another aspect, the spinning membrane separator is primed prior to withdrawing whole blood from the donor. Further, after at least a portion of the second quantity of plasma is returned to the donor, saline may also be returned to the donor. If a filter is used for leukoreduction of the separated red blood cells, the filter may be flushed with additive solution after the total desired volume of red blood cells is collected.

In accordance with another aspect of the present disclosure, a fluid processing circuit for the collection of leukoreduced red blood cells. The circuit includes a blood separator for separating red blood cells from whole blood. The separator has a membrane configured to spin about a generally vertically-oriented axis within a housing which includes an upper end region and a lower end region in the operating position. The separator also includes a red blood cell outlet in the upper end region of the housing and a whole blood inlet in the lower end region of the housing. The circuit further includes an additive solution flow path connecting a source of additive solution to the whole blood inlet and a red blood cell flow path connecting a leukoreduction filter to the red blood cell outlet. A red blood cell collection container is connected to the leukoreduction filter for collecting red blood cells after passage through the leukoreduction filter. The system also includes another or second flow path for additive solution that connects the source of additive solution to the red blood cell flow path at a junction upstream of the leukoreduction filter. The additive solution is mixed with red blood cells prior to passage through the leukoreduction filter.

In accordance with yet another aspect, a method for collecting leukoreduced red blood cells that employs a spinning membrane separator including a membrane configured to spin about a generally vertically-oriented axis within a housing. The housing includes an upper end region and a lower end region in the operating position. The separator also includes a red blood cell outlet in the upper end region of the housing and a whole blood inlet in the lower end region of the housing. The method includes flowing additive solution into the whole blood inlet of the housing to prime the separator. Whole blood is flowed into the whole blood inlet of the housing wherein red blood cells are separated from the whole blood. The separated red blood cells flow out of the red blood cell outlet of the housing and are combined with additive solution. The separated red blood cells and additive solution combination are passed through a leukoreduction filter and collected.

In accordance with yet another aspect, a system for separating blood includes a blood separator for separating red blood cells from whole blood and a leukoreduction filter that filters leukocytes from the red blood cells as the red blood cells pass through the filter. The system also includes a pump that pumps additive solution through the leukoreduction filter to flush remaining red blood cells from the filter after filtration. The pump increases the flush rate of the additive solution through the leukoreduction filter during flushing of the filter.

In accordance with a further aspect, a blood processing system includes a leukoreduction filter for removing leukocytes from red blood cells as the red blood cells pass through the filter and a pump for pumping an additive solution through the leukoreduction filter to flush the leukoreduction filter of red blood cells that remain in the leukoreduction filter after filtration of the red blood cells. The pump controls the flush rate of the additive solution through the filter and varies the flush rate of the additive solution during flushing of the leukoreduction filter.

In accordance with another aspect, a method of flushing a leukoreduction filter includes flowing additive solution through the leukoreduction filter at an initial flush rate to flush remaining red blood cells from the leukoreduction filter and increasing the flush rate of the leukoreduction filter during flushing of the filter.

In accordance with yet another aspect, a method of creating an additive solution flush rate ramp-up schedule for flushing a leukoreduction filter. The method includes forming a first correlation between hematocrit and hemolysis at selected additive solution flush rates through the leukoreduction filter and forming a second correlation between hematocrit decay and the time it takes to decay hematocrit at the selected additive solution flush rates through the leukoreduction filter. The first and second correlations are used to determine the additive solution flush rate ramp-up schedule.

BRIEF DESCRIPTION OF THE DRAWINGS

These and other features of the present subject matter are described in the following detailed description and shown in the attached figures, of which.

DETAILED DESCRIPTION

A more detailed description of the spinning membrane separator in accordance with the present disclosure and its use in various automated systems is set forth below. It should be understood that description below of specific devices and methods is intended to be exemplary, and not exhaustive of all possible variations or applications. Thus, the scope of the disclosure is not intended to be limiting, and should be understood to encompass variations or embodiments that would occur to persons of ordinary skill.

Figures 1, 2:
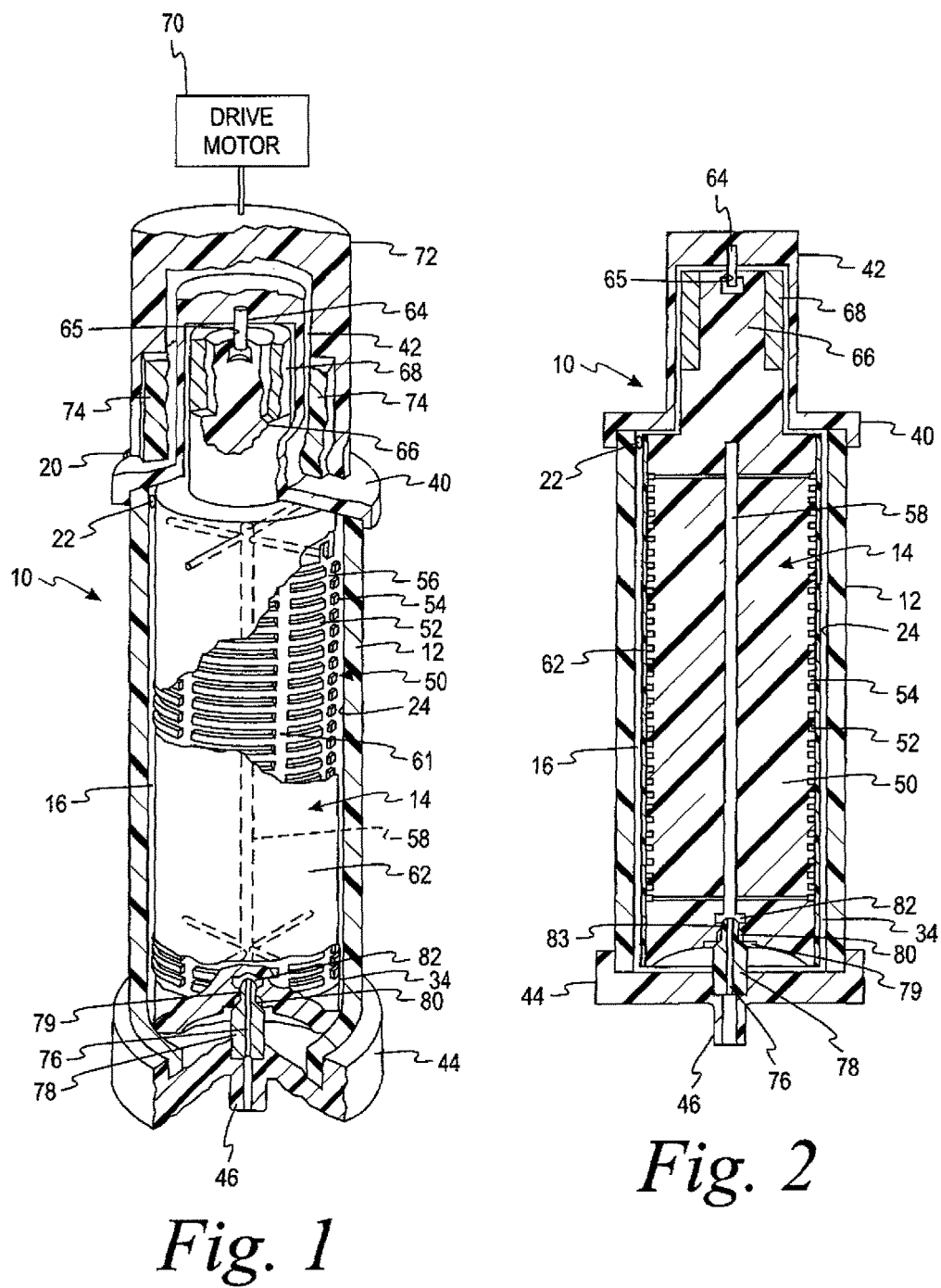
FIG. 1 is a perspective view a spinning membrane separator, in partial cross section and with portions removed to show detail.
FIG. 2 is a longitudinal cross sectional view of the spinning membrane separator of FIG. 1.

Turning to FIGS. 1 and 2, a spinning membrane blood separation or fractionation system, generally designated 10, is shown. Such a system 10 is typically used to extract plasma from whole blood obtained from an individual human donor. For ease of understanding, only the plasma separation device and the associated drive unit are shown, although it should be understood that such a separator forms part of a disposable system including collection bags, bags of additives such as saline or ACD, return bags, tubing, etc., and that there are also associated control and instrumentation systems for operation of the device.

The system 10 includes a generally cylindrical housing 12, mounted concentrically about a longitudinal vertical central axis. An internal member 14 is mounted concentric with the central axis. The housing and internal member is relatively rotatable. In the preferred embodiment, as illustrated, the housing is stationary and the internal member is a rotating spinner that is rotatable concentrically within the cylindrical housing 12. The boundaries of the blood flow path are generally defined by the gap 16 between the interior surface of the housing 12 and the exterior surface of the rotary spinner 14. The spacing between the housing and the spinner is sometimes referred to as the shear gap. A typical shear gap may be approximately 0.025-0.050 inches (0.067-0.127 cm) and may be of a uniform dimension along the axis, for example, where the axis of the spinner and housing are coincident. The shear gap may also vary circumferentially for example, where the axis of the housing and spinner are offset.

The shear gap also may vary along the axial direction, for example preferably an increasing gap width in the direction of flow to limit hemolysis. Such a gap width may range from about 0.025 to about 0.075 inches (0.06-0.19 cm). For example the axes of the housing and rotor could be coincident and the diameter of the rotor decrease in the axial direction (direction of flow) while the diameter of inner surface of the housing remains constant or the diameter of the housing increases while the rotor diameter remains constant, or both surfaces vary in diameter. For example the gap width may be about 0.035 inches (0.088 cm) at the upstream or inlet end of the gap and about 0.059 inches (0.15 cm) at the downstream end or terminus of the gap. The gap width could be varied by varying the outer diameter of the rotor and/or the inner diameter of the facing housing surface. The gap width could change linearly or stepwise or in some other manner as may be desired. In any event, the width dimension of the gap is preferably selected so that at the desired relative rotational speed, Taylor-Couette flow, such as Taylor vortices, are created in the gap and hemolysis is limited.

Whole blood is fed from an inlet conduit 20 through an inlet orifice 22, which directs the blood into the blood flow entrance region in a path tangential to the circumference about the upper end of the spinner 14. At the bottom end of the cylindrical housing 12, the housing inner wall includes an exit orifice 34.

The cylindrical housing 12 is completed by an upper end cap 40 having an end boss 42, the walls of which are nonmagnetic, and a bottom end housing 44 terminating in a plasma outlet orifice 46 concentric with the central axis.

The spinner 14 is rotatably mounted between the upper end cap 40 and the bottom end housing 44. The spinner 14 comprises a shaped central mandrel or rotor 50, the outer surface of which is shaped to define a series of spaced-apart circumferential grooves or ribs 52 separated by annular lands 54. The surface channels defined by the circumferential grooves 52 are interconnected by longitudinal grooves 56. At each end of the mandrel 50, these grooves 56 are in communication with a central orifice or manifold 58.

In the illustrated embodiment, the surface of the rotary spinner 14 is at least partially, and is preferably substantially or entirely, covered by a cylindrical porous membrane 62. The membrane 62 typically has a nominal pore size of 0.6 microns, but other pore sizes may alternatively be used. Membranes useful in the washing methods described herein may be fibrous mesh membranes, cast membranes, track etched membranes or other types of membranes that will be known to those of skill in the art. For example, in one embodiment, the membrane may have a polyester mesh (substrate) with nylon particles solidified thereon, thereby creating a tortuous path through which only certain sized components will pass. In another embodiment, the membrane may be made of a thin (approximately 15 micron thick) sheet of, for example, polycarbonate. In this embodiment, pores (holes) may be larger than those described above. For example, pores may be approximately 3-5 microns. The pores may be sized to allow small formed components (e.g., platelets, microparticles, etc.) to pass, while the desired cells (e.g., white blood cells) are collected.

The rotary spinner is mounted in the upper end cap to rotate about a pin 64, which is press fit into the end cap 40 on one side and seated within a cylindrical bearing surface 65 in an end cylinder 66 forming part of the rotary spinner 14. The internal spinner or outer housing may be rotated by any suitable rotary drive device or system. As illustrated, the end cylinder 66 is partially encompassed by a ring 68 of magnetic material utilized in indirect driving of the spinner 14. A drive motor 70 exterior to the housing 12 is coupled to turn an annular magnetic drive member 72 that includes at least a pair of interior permanent magnets 74. As the annular drive member 72 is rotated, magnetic attraction between the ring 68 interior to the housing 12 and the magnets 74 exterior to the housing locks the spinner 14 to the exterior drive, causing the spinner 14 to rotate.

At the lower end of the rotary spinner 14, the central outlet orifice 58 communicates with a central bore 76 in an end bearing 78 that is concentric with the central axis. An end bearing seat is defined by an internal shoulder 80 that forms a lower edge of a central opening 82. The central opening 82 communicates with the plasma outlet orifice 46. If the inner facing surface of the housing is covered entirely or partially by a membrane, a fluid collection or manifold may be provided beneath the membrane to collect plasma and direct it through a housing outlet (not shown).

I. Membrane Separator Design

In keeping with one aspect of the application, a spinning membrane separator is provided that provides for improved plasma flow rates with an acceptably low level of hemolysis in the retained blood. Various factors are known to affect the filtration flow rate through spinning membrane separators, including the speed of rotation, the size of the gap between the spinning membrane and the shell, the effective area of the membrane, the concentration of red blood cells (or hematocrit), and the blood viscosity. Previous practices in the design of spinning membrane devices have been largely empirical, aided to some extent by vague phenomenological descriptions of the effects of the various design parameters on performance and hemolysis. This has proved to be inefficient in terms of development time and technical resources spent.

In contrast, the parameters of the spinning membrane separator of the present application were determined based on quantitative differential models that take into account the local plasma velocity through the membrane and the local hemoglobin concentration. These differential models were integrated over the length of the device to provide a total plasma flow rate and plasma hemoglobin concentration at the outlet of the device.

The method included the operational inputs based upon the existing Plasmacell-C separator geometry and operating conditions, including donor hematocrit, inlet blood flow rate, rotational speed, and effective membrane area. Also factored in were the geometric inputs of rotor radius, the width of the annular gap, and the length over which the integration is performed. See Table 1 below. To obtain predicted values for hypothetical separators, rotor radius and filtration length were varied from about 1.0 to up to about 2.0 times the current Plasmacell-C values in increments of 0.05, providing a 21×21 design space grid for each output variable of interest. For all devices, the housing taper and the gap at the outlet were held constant, and the inlet gap and rotational speed were varied accordingly. Models were also developed which related blood viscosity and density to hematocrit, temperature, and anticoagulant concentration.

Figure 3:
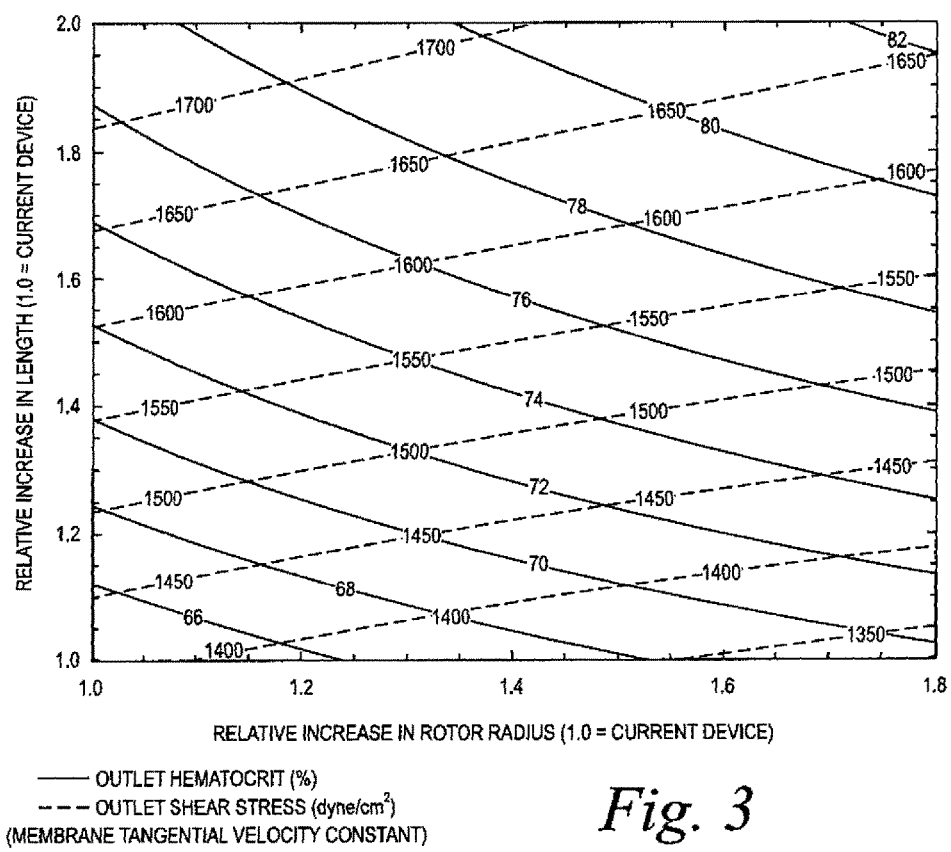
FIG. 3 is a contour plot of outlet hematocrit and outlet wall shear stress as a function of relative filtration length and spinner radius based on a theoretical design model.
Figure 4:
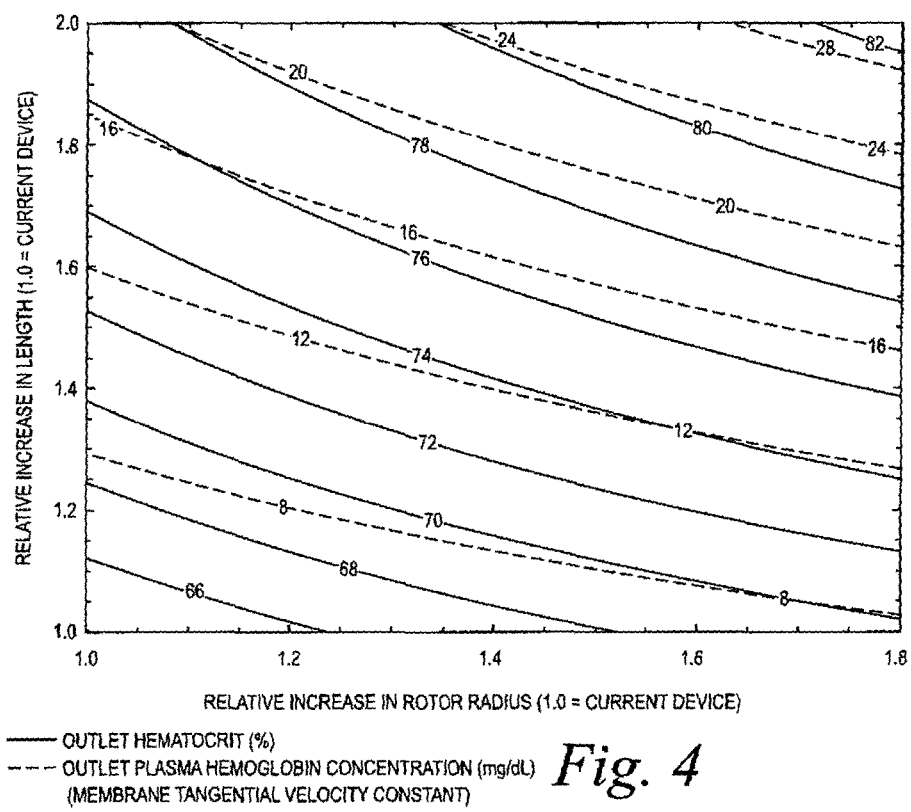
FIG. 4 is a contour plot of outlet hematocrit and outlet plasma hemoglobin concentration as a function of relative filtration length and spinner radius based on a theoretical design model for which the membrane tangential velocity is constant.
Figure 5:
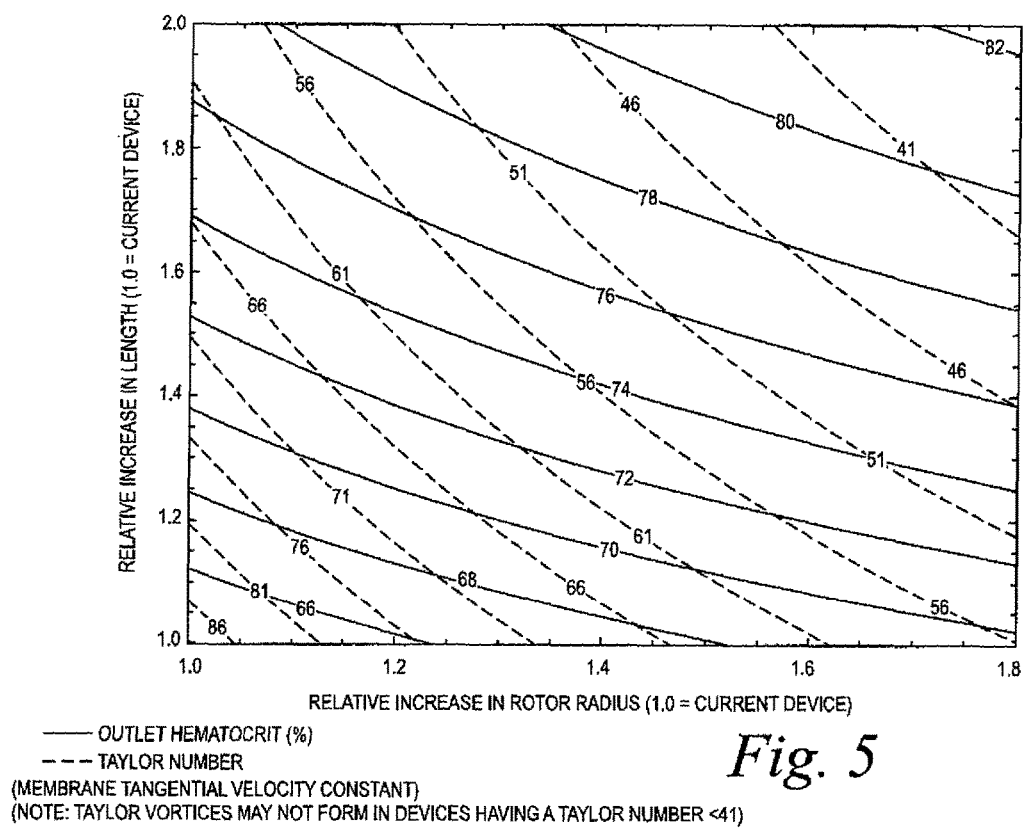
FIG. 5 is a contour plot of outlet hematocrit and Taylor number as a function of relative filtration length and spinner radius based on a theoretical design model.
Figure 6:
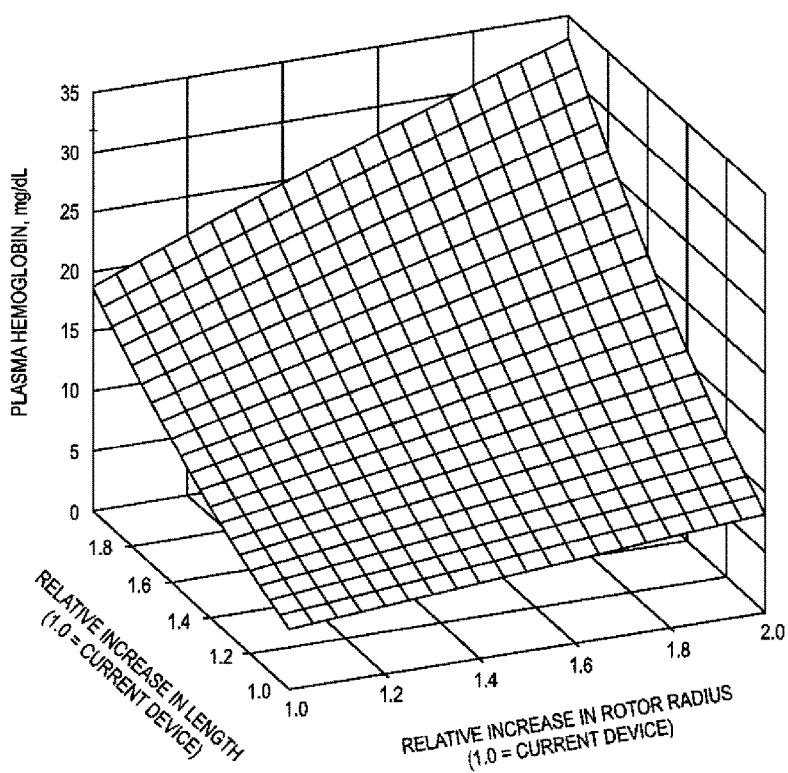
FIG. 6 is a three-dimensional plot of plasma hemoglobin concentration as a function of relative filtration length and spinner radius based on a theoretical design model.

In one implementation of the method, outputs of plasma flow rate and hemoglobin concentration were obtained for various values of the rotor radius, the rotational speed, and the integration length. The results of the models are shown in superimposed contour plots of the outlet hematocrit and outlet wall shear stress (FIG. 3), the outlet hematocrit and the outlet plasma hemoglobin concentration (FIG. 4), and the outlet hematocrit and Taylor number (FIG. 5), all as a function of the relative filtration length and spinner radius. (The "Taylor number" is a dimensionless quantity that characterizes the inertial forces due to rotation of a fluid about an axis relative to viscous forces.) As used herein, "filtration length" is understood to be axial length of the central mandrel or rotor 50 from the beginning to the end of grooves or ribs 52. It generally represents the length of the membrane available for filtration. The "spinner radius" or "spinner diameter" is understood to be the radius or diameter of the rotor with the membrane attached. FIG. 6 shows the plasma hemoglobin results as a function of filtration length and spinner radius in a three-dimensional plot, showing the increase in hemoglobin with larger devices. These results were then evaluated to provide the best balance of high plasma flow rate with acceptably low levels of hemolysis.

The models indicated that the effective area of the membrane has the strongest positive influence on performance. Further, while increasing the membrane area by increasing the diameter of the rotor more positively impacts flow rates than increasing the membrane area by increasing the length of the rotor, it also increases the potential for hemolysis due to the increased velocity of the membrane, and thus the increase in shear forces in the gap.

Accordingly, the models predicted lengths and diameters for the rotor that would result in increased membrane areas whose use would also have acceptably low levels of hemolysis. Prototype separators (based on the results of the models) were made and tested to validate the results predicted by the models. Table 2, below, compares a current Plasmacell-C plasmapheresis device with two potential alternatives based on the models.

TABLE 1

| Inputs for Model Calculations | |
|---|---|
| Parameter, units | Value |
| Inlet blood flow rate, ml/min | 106 |
| Inlet hematocrit, % | 42 |
| Temperature, ° C. | 35 |
| Citrate concentration, % | 5.66 |
| Filtration length, in | 2.992 |
| Rotor radius with membrane, in | 0.5335 |
| Inlet gap, in | 0.0265 |
| Outlet gap, in | 0.0230 |
| Effective membrane fraction | 0.50 |
| Width of membrane bonding area, in | 0.18 |
| Rotation speed, rpm | 3600 |
| Wall hematocrit, % | 0.90 |
| Red cell radius, μm | 2.75 |
| Red cell hemoglobin concentration, mg/dL | 335.60 |
| Density of plasma, g/cm3 | 1.024 |
| Density of packed red cells, g/cm3 | 1.096 |
| Viscosity of citrated plasma, cP | 1.39 |

TABLE 2

| | Device | | |
|---|---|---|---|
| Parameter, units | Plasmacell-C | RL 140-162 | RL 140-185 |
| Relative filtration length | 1.00 | 1.62 | 1.85 |
| Relative spinner radius | 1.00 | 1.40 | 1.40 |
| Relative spinner speed | 1.00 | 0.70 | 0.75 |
| Filtration length, in | 2.992 | 4.847 | 5.535 |
| Spinner radius, in | 0.5335 | 0.7469 | 0.7469 |
| Spinner speed, rpm | 3600 | 2520 | 2700 |
| Inlet gap, in | 0.0265 | 0.0287 | 0.0295 |
| Outlet gap, in | 0.0230 | 0.0230 | 0.0230 |
| Inlet flow rate, ml/min | 106 | 106 | 106 |
| Inlet hematocrit, % | 42 | 42 | 42 |
| Citrate concentration, % | 5.66 | 5.66 | 5.66 |
| Plasma flow rate. ml/min | 36.33 | 47.42 | 50.57 |
| Outlet hematocrit, % | 63.90 | 76.00 | 80.32 |
| Outlet plasma hemoglobin concentration, mg/dL | 5.04 | 14.36 | 27.84 |
| Residence time, s | 2.98 | 7.99 | 9.77 |
| Centripetal pressure, mmHg | 100.22 | 96.25 | 110.50 |

TABLE 2-continued

| | Device | | |
|---|---|---|---|
| Parameter, units | Plasmacell-C | RL 140-162 | RL 140-185 |
| Torque, in-oz | 1.48 | 4.70 | 6.29 |
| Outlet Taylor number | 89.07 | 51.00 | 46.96 |

Figure 7:
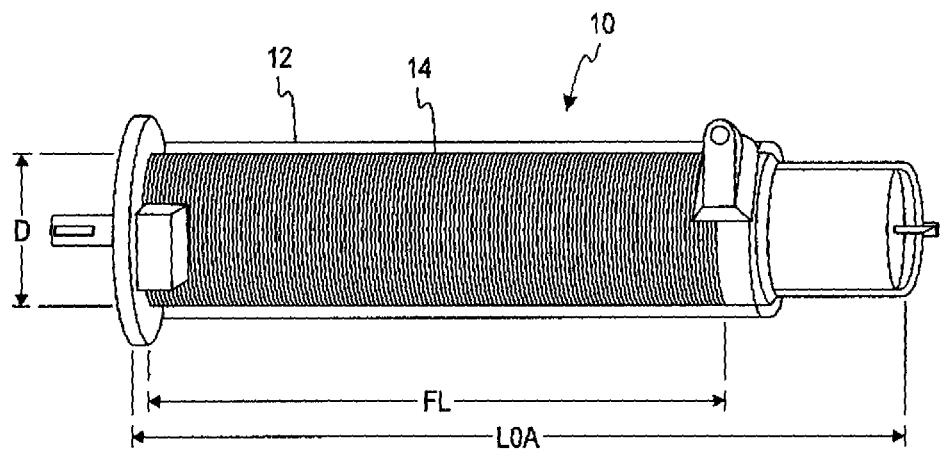
FIG. 7 is a perspective view of a spinning membrane device or separator according to the present application.

With reference to Table 2 and FIG. 7, a spinning membrane separator 10 includes a rotary spinner 14 which has a spinner diameter D, a filtration length FL, and an overall length LOA. In a typical plasmapheresis device, such as the Plasmacell-C separator, the rotor has a diameter D of approximately 1.1", a filtration length FL, of approximately 3", and an overall length, LOA, of approximately 5.0".

In accordance with the present application, it has been found that the diameter of the membrane can be increased by up to about 2.0 times the diameter of the membrane found in a typical plasmapheresis device, while the length can be increased up to about 2.5 times the length of the spinning membrane in a typical plasma pheresis device. An increase in the rotor size within these perimeters increases the filter membrane area sufficient to provide for a high plasma flow rate, while providing for an acceptably low level of hemolysis. In a specific example, a spinning membrane separator according to the present application may advantageously have a diameter D of 1.65", a filtration length FL of 5.52", and an overall length LOA of 7.7".

Prototype spinning membrane separators were tested with bovine and human blood to validate the results predicted by the models. Blood flow rates of 100 ml/min were obtained with spinner speeds varying from 1000-3500 rpm. Outlet hematocrit levels of 80% and higher were obtained before high levels of fouling of the membrane were experienced. Collection times for 880 ml of plasma ranged from between approximately 18 and 20 minutes.

As noted above, the residence time of the red blood cells in the shear gap has a direct relationship to the amount of hemolysis. In spinning membrane separation devices, flow regions exist along the axial length of the rotor where the fluid flows is relatively stagnant, resulting in pockets of hemolysis. To the extent that red blood cells from the high hemolysis region intermix with the flow in the low hemolysis region, the quality of the collected red blood cells is degraded.

Accordingly, in keeping with another aspect of the application, a method is provided for creating separate fluid flow regions in the gap of a spinning membrane separator without the use of seals. The separate flow regions reduce or minimize the influence of mixing of the fluids between the two flow regions. The separate flow regions are achieved by having a raised rib or ridge in the gap to reduce or minimize the gap between the spinner and the outer cylinder. Preferably, the ridge or rib is provided on the surface of the rotor beyond where the spinning membrane is attached thereto.

The ridge is preferably located so as to define the boundary of the high perfusion flow region. The radial size of the ridge is inversely proportional to the decree of mixing allowed between the two regions defined thereby, with a larger radial dimension for the ridge allowing for less mixing. The axial dimension or extent of the ridge is also inversely proportional to the degree of mixing allowed, with a larger axial dimension allowing for less mixing. The axial dimension of the ridge is preferably at least one gap-size long to minimize the formation of adjacent Taylor vortices causing unwanted mixing.

Figure 8:
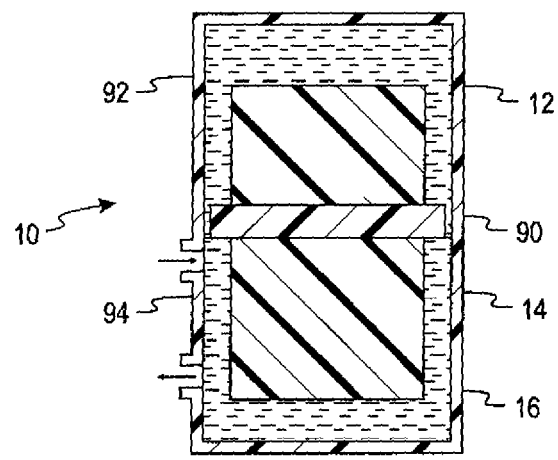
FIG. 8 is a schematic cross sectional view of a spinning membrane separator in accordance with the present application in which the spinner includes a radially-extending ridge for defining separate fluid regions.

With reference to FIG. 8, a schematic cross sectional representation of a spinning membrane separation device 10 is shown. The device comprises a fixed outer cylinder 12 and a rotating inner cylinder 14 having a filter member carried thereon. In accordance with the present application, the inner cylinder is provided with a radial ridge 90. This ridge serves to divide the gap 16 between the spinner and the outer housing into two fluid regions. A first fluid region 92 has a stagnant, non-perfused region of flow, typically on the portion of the spinner that extends beyond the filter membrane. A second fluid region 94, which typically contacts the filter membrane, has a highly perfused region of flow.

Because the first fluid region 92 is not perfused, blood residing therein is exposed to increased shear stresses for longer periods of time than the blood in the second fluid region 94. Thus, the blood in the first fluid region 92 may often become hemolyzed and has high concentrations of free hemoglobin (Hb). The ridge 90 inhibits fluid flow between the two fluid regions, thus minimizing the extent of mixing of the Hb-contaminated blood in the first region 92 with the low Hb blood in the second region 94.

While the ridge 90 is shown as being integral with the rotor, it could also be formed on the inside of the outer cylinder to achieve the same effect. As noted above, the axial dimension of the ridge should be at least one-gap size long. A typical spinning membrane separation device for performing plasmapheresis typically has a gap between the spinner and the containment wall of from 0.023" to 0.0265", and a ridge in accordance with the present application could have an axial dimension within the same general range. However, larger axial dimensions for the ridge will result in reduced mixing and, in one example, a rotor having a radially-extending ridge with an axial dimension of 0.092" has been found to be effective.

II. Systems and Methods for Processing Previously Collected Whole Blood

A spinning membrane separation device as described above may be advantageously used in various blood processing systems and methods for which prior devices generally were not suited, particularly systems and process for obtaining Red Blood Cells. In one type of system and method, the spinner may be used for "back lab" processing of previously collected whole blood, as shown in FIGS. 9-15A.

Figure 9:
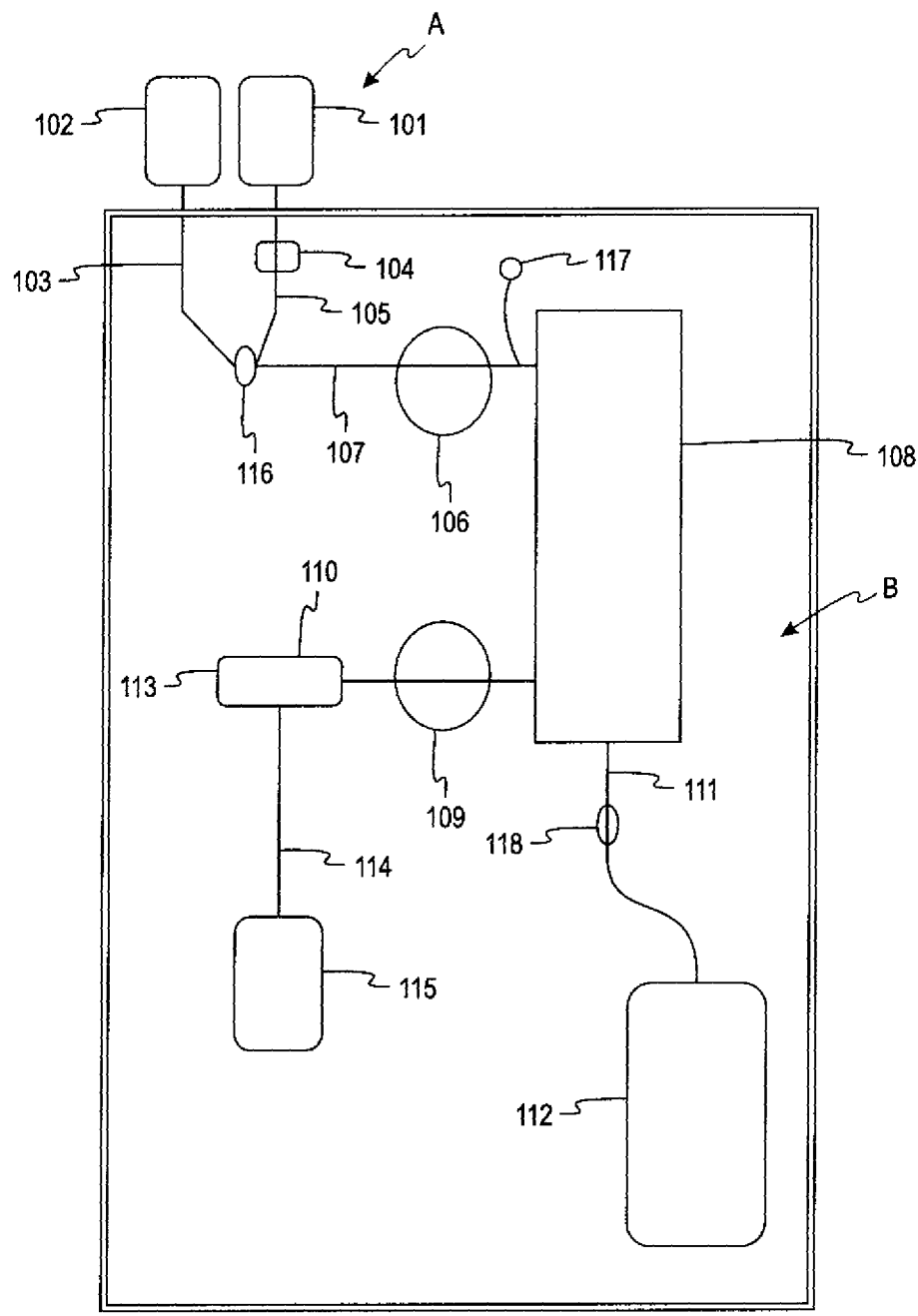
FIG. 9 is a schematic view of an automated whole blood separation system for processing previously-collected whole blood including a disposable fluid flow circuit module and a durable controller or control module with the fluid flow circuit module assembled thereon.

Turning now to FIG. 9, a disposable fluid flow circuit or module A and a reusable durable controller or module B configured to cooperate with and control flow through the fluid circuit A are schematically illustrated. The disposable fluid circuit A as illustrated in FIG. 9 includes various components interconnected by flexible plastic tubing defining flow paths between the components. The circuit is preferably fully pre-assembled and pre-sterilized with the possible exception of the unit of whole blood container and the cell preservative container. More specifically, the illustrated disposable circuit in FIG. 9 includes whole blood container 101, a cell preservation solution container 102, blood component separator 108, plasma collection container 112, optional leukocyte reduction filter 113, and red cell collection container 115. While not illustrated in FIG. 9, the reusable module B may have hangers with associated weigh scales for supporting any or all of the containers 101, 102, 112 and 115. In various of the other embodiments discussed herein, such hangers/weigh scales may not be illustrated, but are understood to be part of the described systems.

The whole blood collection container 101 may be any suitable container but is typically a flexible plastic pouch or bag in which approximately 450 ml of whole blood have been previously collected. The container 101 may be part of a separate system during collection and then joined to the rest of the fluid circuit A or actually part of the circuit A at the time of collection. At the time collection, in accordance with customary procedure, the whole blood is mixed with an anticoagulant located in the primary container to prevent premature coagulation. Accordingly, "whole blood" as used herein includes blood mixed with anticoagulant.

Flexible plastic tubing 105 is attached to the whole blood collection container, such as by a sterile connection device or other suitable attachment mechanism, and defines a whole blood fluid flow path between the whole blood container 101 and a junction with cell preservative solution tubing 103, which extends from the cell preservation solution container 102 to the flow path junction. The flow path junction between the whole blood flow path and all preservative flow path is located at inlet clamp 116. From the junction, the flow path extends through tubing 107 to an inlet port in the separator 108.

As shown in FIG. 9 of this description, the separator housing has an outlet that communicates with the gap between the housing and rotor and with concentrated red cell flow path tubing 110 for withdrawing concentrated red cells from the separator gap. In addition, the housing includes an outlet from the rotor that communicates with the side of the membrane facing away from the gap (for example, the interior of the rotor) and communicates with plasma flow path tubing 111.

For reducing the number of leukocytes that may be present in the red cells, the disposable fluid flow circuit A optionally includes a leukocyte reduction filter 113, which may be of any suitable well known construction for removing leukocytes from concentrated red cells without unduly causing hemolysis of red cells or reducing the number of red cells in the collected product. The concentrated red cells flow from the leukocyte reduction filter 113 through a continuation 114 of the concentrated red cell flow path into storage container 15 which may be of any suitable plastic material compatible with red cell storage.

The reusable or durable controller module B, as shown in the FIG. 9 schematic, preferably includes a hematocrit sensor 104 for detecting the hematocrit and the whole blood flowing from the whole blood container 101. The hematocrit detector may be of any suitable design or construction but is preferably as described in U.S. Pat. No. 6,419,822, which is hereby incorporated by reference.

The durable reusable controller or control module B also includes an inlet clamp 116 which may be operated to control fluid from the whole blood container 101 or the cell preservative container 102 or, optionally, simultaneously and proportionally from both of the containers 101 and 102. For controlling flow of blood into the separator, the reusable module includes an inlet pump 106, which also may be of any suitable construction, and may be, for example, a peristaltic type pump which operates by progressive compression or squeezing of the tubing 107 forming the inlet flow path into the separator, a flexible diaphragm pump or other suitable pump. A pressure sensor 117 communicates with the inlet flow path between the pump 106 and the separator 108 to determine the inlet pumping pressure. The sensor may output to the control system to provide an alarm function in the event of an over-pressure condition or an under-pressure condition or both.

To control the flow rate of concentrated red cells from the separator 108, the reusable module also includes an outlet pump 109 that is associated with the outlet flow path 110, and functions in the manner similar to that described with respect to inlet pump 106. It also may be of any suitable construction such as a peristaltic pump, a flexible diaphragm or other suitable pumping structure. The plasma flow path 111 exiting the separator is preferably not controlled by a pump, and the volumetric flow rate through the plasma flow path tubing is the difference between the inlet volumetric flow rate from pump 106 and the outlet volumetric flow rate from pump 109. Reusable module B may, however, also include a clamp 118 for controlling flow of plasma through the plasma flow path tubing 111.

The disposable module A may also include a plasma collection container 112 in fluid communication with the plasma flow path for receiving plasma separated by the separator 108. Because the plasma passes through a porous membrane in the separator 108, the plasma that is collected in container 112 is largely cell free plasma and may be suitable for administration to patients, freezing for storage or subsequent processing.

Figure 10:
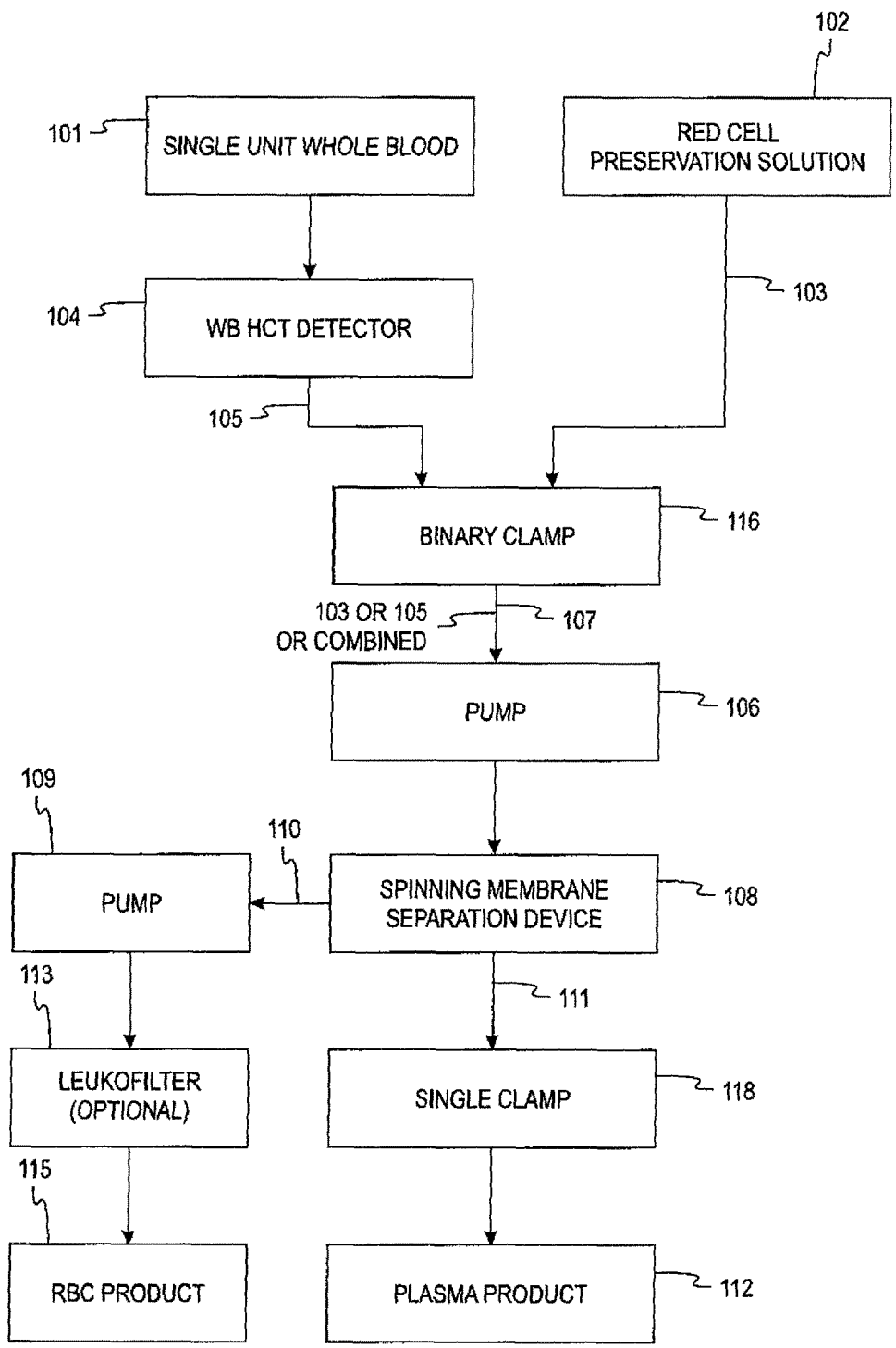
FIG. 10 is a flow diagram showing one embodiment of fluid flow through a fluid flow circuit as described herein for processing a unit of whole blood into a concentrated red cell product and a plasma product.

FIG. 10 generally shows the flow path(s) of fluid through the system illustrated in FIG. 9. Specifically, it shows flow of whole blood from the single unit whole blood container 101 through the whole blood hematocrit detector 104, to a junction in the flow path located at the binary clamp 116. Cell preservation solution, such as a red cell preservation solution, flows from the red cell container 102 also to the junction at the binary clamp 116. Depending on the processing stage, the binary clamp allows the flow of whole blood or cell preservative downstream into the remainder of the system. Optionally, the clamp 116 could be a proportional clamp to allow a selected proportionate flow of whole blood and red cell preservative simultaneously.

From the binary clamp 116, the whole blood or cell preservative fluid flows through the inlet pump 106 and into the separation device 108. As explained earlier, the separation device employs a relatively rotating housing and rotor, at least one of which carries a membrane through which plasma is allowed to pass. In one embodiment, the membrane is carried on the surface of the rotor and plasma passes through the membrane and through internal passage labyrinth within the rotor exiting eventually to the plasma collection container 112. When the membrane is mounted on the rotor, the device is commonly referred to a spinning membrane separator, as shown in FIG. 10. However, it should be recognized that the membrane could potentially be mounted on the inside surface of the housing, facing the gap between the inside surface of the housing wall and the outer surface of the membrane, or a membrane could be carried on both the outer surface of the rotor and the inner surface of the housing so that plasma flows through membranes simultaneously, therefore potentially increasing the separation speed or performance of the separator 108. From the separator 108, the concentrated red cells flow through the housing outlet communicating with the gap between rotor and housing and through the red cell flow path 110 and the outlet pump 109, which controls the volumetric flow rate of the concentrated red cells.

While the hematocrit of the concentrated red cells removed from separator 108 may vary, it is anticipated that the hematocrit of the concentrated red cells will be approximately 80-85%. The outlet pump 109 pumps the concentrated red cells into the red cell collection container 115 and, optionally, through a leukocyte reduction filter located in the red cell flow path between the pump 109 and the collection container 115. The force of the pump pushing the concentrated red cells through the leukocyte reduction filter helps to maintain the processing time within a reasonable range, as compared, for example, to the time it would be required for gravity flow of concentrated red cells through a leukocyte reduction filter in a manual setting.

The plasma separated by the separator 108, as shown in the FIG. 10, flows from the separator device, for example, from an outlet communicating with a labyrinth of passageways within the rotor through a single control clamp 118 and to the plasma collection container 112. As noted earlier, because the plasma passes through the membrane, it is largely cell free and suitable for subsequent administration to patients, freezing, and/or for the processing, such as by fractionation to obtain plasma components for use in other therapeutic products. The system could also include a filter such as a leukocyte reduction filter in the plasma flow line 111 if desired.

Figure 11:
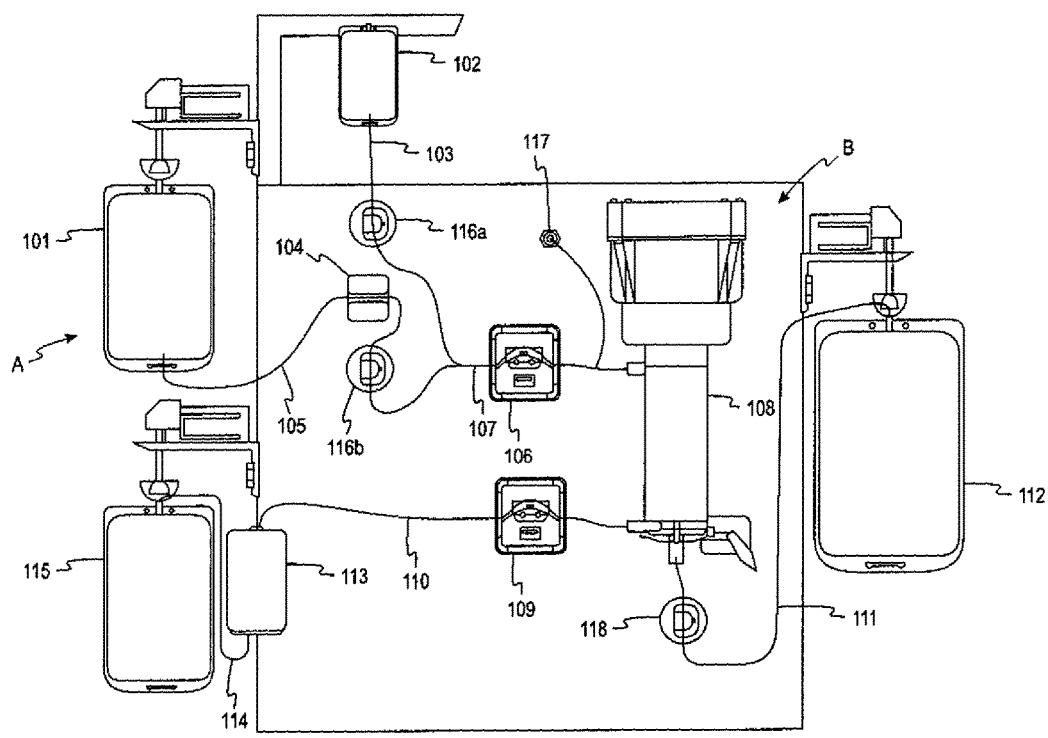
FIG. 11 is similar to FIG. 9 but a somewhat more detailed view of components of a disposable fluid flow circuit or module and a durable controller module.

FIG. 11 illustrates one version of a potential system employing both a disposable fluid circuit module A and a reusable or durable controller module B. Although shown assembled, the fluid circuit module A and durable module B have separate and independent utility and may be used with other systems as well. As can be seen in FIG. 11, the disposable module A is conveniently mounted to the face of the reusable module B, which has associated hangars or supports, some of which may be associated with weight scales, for supporting the various containers of the disposable system. The disposable module is, as indicated earlier, preferably preassembled, and pre-sterilized. The cell preservative solution container may be pre-attached as part of the disposable system or may be added later, such as by a sterile connection device or other suitable attachment. The whole blood container which contains the unit of previously collected whole blood may also be pre-attached to the pre-assembled fluid circuit or attached by way of a sterile connection device or other suitable attachment mechanism.

The face of the reusable module B includes, in this embodiment, a separate solution clamp 116a for controlling flow of cell preservation solution from the solution container 102, which is hung from an elevated solution support pole. The whole blood container 101 is hung from a weight scale. The weight scale may be of conventional construction and may provide a weight measurement signal that may be used by the control system of the module B for sensing the amount of whole blood that remains in the container and/or the amount of whole blood that has been processed through the system. The disposable system includes a red cell flow path 105 that extends from the whole blood container, through the hematocrit detector 104, and through a separate whole blood clamp 116b for controlling flow of whole blood from the container into the system. The cell preservative solution flow path 103 and the whole blood flow path 105 combine at a junction, such as a v-site or y-site, upstream of the inlet pump 106. The combined flow path extends through the inlet pump and to an inlet on the separator device 108. As is visible in FIG. 11, the reusable module B includes a drive unit, such as a magnetic drive unit for causing rotation of the rotor within the separator housing without requiring drive members or components to physically extend through the housing. In this arrangement, the rotor includes a magnetically coupled drive element that is rotated by the magnetic drive unit associated with the reusable module. This system is described more fully in U.S. Pat. No. 5,194,145 to Schoendrofer, incorporated by reference herein.

The concentrated red cell outlet from the separator 108 is attached to the red cell flow path 110, which extends through outlet pump 109 and to an inlet into the optional leukocyte reduction filter 113. Filter media located between the inlet and outlet of the leukocyte reduction filter substantially removes leukocytes from the red cells. From the filter outlet, the red cell flow path tubing 114 conveys the red cells into the red cell collection container 115.

Plasma is conducted from the plasma outlet of the separator through a plasma flow control clamp 118 and into the plasma collection container 112. In a manner similar to the whole blood container, the concentrated red cell container 115 and the plasma container 112 are suspended from weight scales which may be in electronic communication with the control system of the durable or reusable module B to provide information regarding the amount of concentrated red cells and/or plasma collected from the whole blood or the rate of collection.

While this system has been illustrated with certain basic components and features as described above, this description is not intended to preclude the addition of other components, such as sensors, pumps, filters or the like as may be desired. For example, it may optionally be desired to filter plasma before it enters the plasma collection container or to omit a leukoreduction filter for red cells. Although the plasma removed from the separator 108 is largely cell free, there may be a further desire to filter the plasma for reasons of subsequent administration or processing. The present description is not intended to preclude the possible addition of further components or the deletion of one or more of the components described above.

Turning now to the processing of whole blood in the illustrated system, the separation process begins by priming the system. "Priming" refers to the method by which the filter membrane is prepared (i.e., wetted) prior to use. Wetting with a fluid helps to displace air present in the matrix of the membrane prior to pressure-induced fluid flow through the membrane. Typically, a low viscosity non-biological fluid, such as a cell preservation solution (red cell solution such as, Adsol® solution) is used for wetting to allow the most effective displacement of air. During the prime, fluid is removed from the cell preservation solution bag 102 by the inlet pump 106 until the solution line 103, whole blood line 105, inlet line 107, and spinning membrane device 108 are completely filled with the solution. To ensure proper priming, the inlet pump 106 may move both clockwise and counterclockwise during the prime. The purpose of the solution prime is to prevent an air-blood interface from forming by creating a solution-blood interface and to wet the membrane within the separation device. Each is a measure taken to reduce the hemolysis of red blood cells.

After the system is successfully primed, the cell solution flow path 103 will be closed by the inlet clamp 116. The illustrated inlet clamp is a binary clamp that can close either the cell preservation solution flow path 103 or the whole blood flow path 107. Whole blood will then be pumped through the whole blood flow path 105 and the inlet flow path 107 by the inlet pump 106 into the separator 108. Inlet pump 106 flow rates can vary from about 10 ml/min to 150 ml/min depending on desired product outcomes for a specific procedure. As the whole blood leaves the whole blood container 101 it will pass through the whole blood hematocrit detector 104 which will generate an estimation of the whole blood hematocrit through IR LED reflectance measurements. Details of the hematocrit detector are explained in U.S. Pat. No. 6,419,822 (Title: Systems and methods for sensing red blood cell hematocrit), incorporated by reference. The whole blood hematocrit value is required for an initial control algorithm of the illustrated system, but may not be essential in other systems.

After whole blood has filled the separator 108, the system will begin to draw plasma from the separator which separates the whole blood entering the spinning membrane device into a red cell concentrate and virtually cell free plasma. Packed red blood cells at approximately 80-85% hematocrit will be pumped out of the separator 108 through the red cell flow path 110 and into the red blood cell leukofilter 113 by the outlet pump 109. The outlet pump forces the packed red blood cells through the red blood cell leukofilter 113 and the red cell concentrate which exits the red blood cell leukofilter 13 through the red blood cell line 114 and into the red blood cell product bag 115 will be successfully depleted of white blood cells and also depleted of platelets. It is also possible to complete a whole blood automated separation without the use of a red blood cell leukofilter 113. In this case the red blood cell leukofilter 114 would be removed from the system and the red blood cell product 115 would not be depleted of white blood cells or platelets.

Throughout the procedure, plasma will flow through the plasma flow path 111 into the plasma bag 112 at a flow rate equal to the difference between the inlet pump 106 flow rate and outlet pump 109 flow rate as is currently done in other spinning membrane separation applications like that applied in the Autopheresis-C® instrument sold by Fenwal, Inc. The pressure across the membrane generated by the offset in flow rates is monitored by the pressure sensor 117. The pressure measurements are used to control the plasma flow rate using the algorithm described in U.S. patent application Ser. No. 13/095,633, filed Apr. 27, 2011 (Title: SYSTEMS AND METHODS OF CONTROLLING FOULING DURING A FILTRATION PROCEDURE) hereby incorporated by reference.

The system in FIGS. 9-11 will continue to separate packed red blood cells and plasma until the whole blood bag 101 is empty as detected by air passing through the whole blood hematocrit detector 104. At this point the whole blood line 105 will be closed and the cell preservative solution line will be opened by the inlet clamp 116 to start the solution rinse or flush. During the solution rinse, preservative solution will be removed from the solution bag 102 and pumped into the separator 108 by the inlet pump 106. The plasma flow path 111 is closed by the plasma clamp 118 during the solution rinse. The solution rinse is used to flush any blood remaining in the system into the red blood cell product container 115. The solution rinse will also increase the red blood cell product container 115 volume to the level desired for proper red blood cell storage. After the solution rinse is finished the separation of the whole blood unit is complete.

Figure 12:
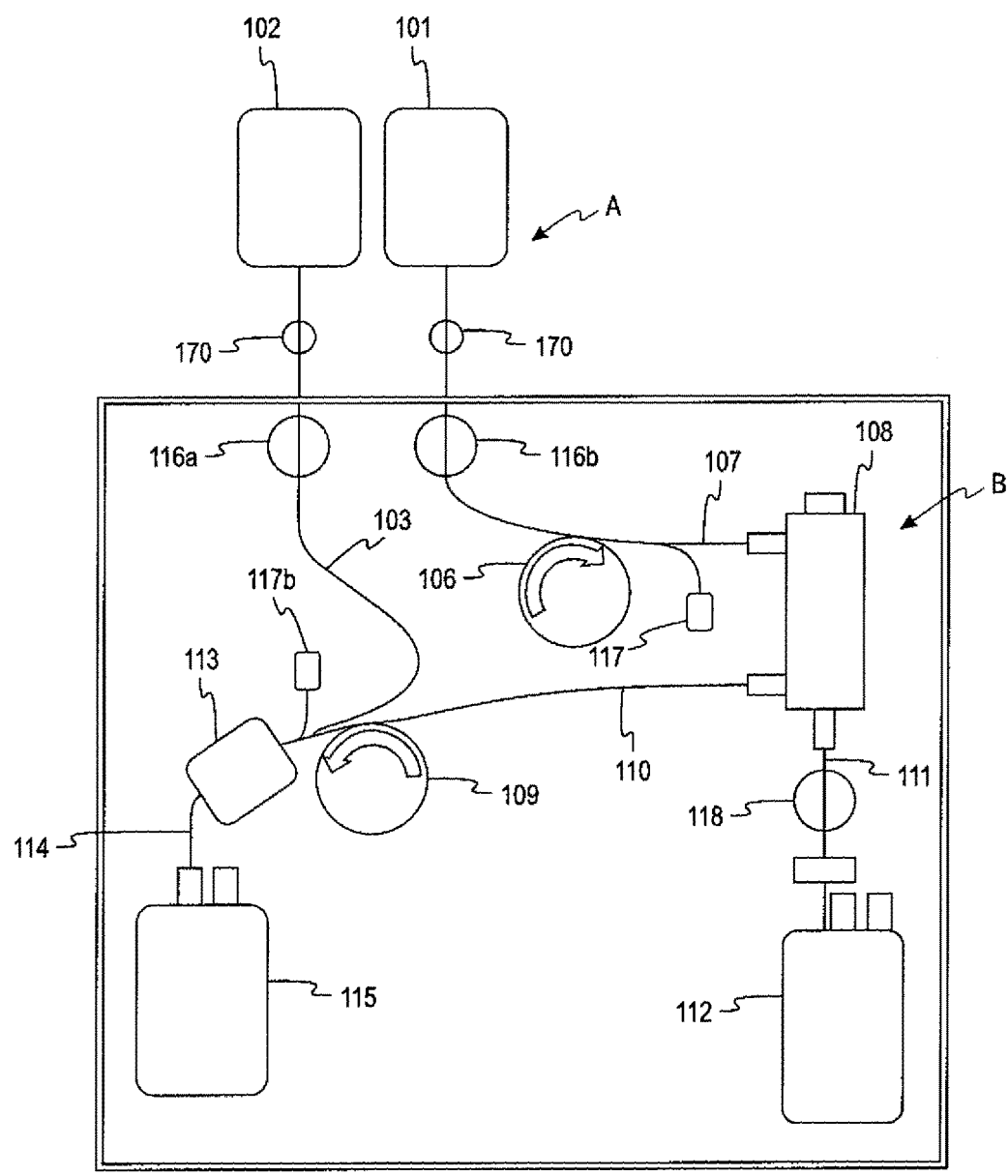
FIG. 12 is a schematic view of an alternate embodiment of the system according to the present disclosure in which the system is used for the separation of previously-collected whole blood.

Turning to FIG. 12, a further alternative two-pump system is shown. This embodiment differs from that in FIG. 9 primarily in that the fluid from the blood cell preservative solution is added after the red blood cells have been separated from the whole blood. More particularly, a container/bag 101 containing previously-collected whole blood (preferably already combined with an anticoagulant) is connected to the disposable system A through tubing segment 107 that leads to the blood separator 108. Pump 106 cooperates with tubing 107 to pump whole blood to the separator 108. Container 102 containing the red blood cell preservative additive solution is connected to the collection container 115 for the separated red blood cells through tubing 114, through which the separated red blood cells are also directed to container 115 through the leukocyte filter 114.

Sterile connection of the containers 101, 102 to the disposable system may be accomplished by a number of different ways. Container 102 for the additive solution may be supplied as part of the disposable system A, and may be joined to the remainder of the disposable (after sterilization by, e.g., gamma or E-Beam processing) during final packaging after the remainder of the disposable has been sterilized (by, e.g., moist heat processing). Alternatively, the container 102 may be formed integrally with the remainder of the disposable. In a further alternative, both the container 102 and the whole blood container 101 may be separate from the remainder of the disposable and connected at the time of use through, e.g., sterile spike connections 170, shown schematically in FIG. 10. Such spike connections preferably include a 0.2 micron filter to maintain sterility.

In another aspect of this embodiment, the tubing 103 connecting the additive solution container 102 to the leukocyte filter 62 may also be cooperatively engaged by the pump 109. Specifically, pump 109 may be a dual pump head that flows both the additive solution and the red blood cells exiting the separator 108 to control the flow rate of each based upon the inside diameter of the tubings 103 and 110.

The embodiment of FIG. 12 also utilizes an additional pressure sensor 117b to monitor the back pressure from the leukocyte filter 113. Should the back pressure become excessive, as in the event of filter occlusion, the sensor will act to control the flow rate in order to ensure that the disposable does not rupture due to excessive pressure.

III. Membrane Priming

In keeping with another aspect of the disclosure, a method for priming a membrane filter is provided by which is more likely that the maximum amount of the surface area of the filter membrane is wetted, thus maximizing the membrane area available for filtration/separation. Specifically, when a spinning membrane filter system is primed as described above, with the spinning membrane oriented so that the axis of rotation is substantially vertical, the wetting solution enters at the top inlet port of the spinning separator, and gravity pulls the fluid toward the outlet at the bottom of the separator. Under such circumstances, the surface tension of the priming fluid will form an air-fluid interface that may move unevenly across the membrane surface, creating disruptions. The result is that certain areas of the filter membrane may not be wetted during priming, thus increasing the potential for air being trapped in the membrane matrix. The unwetted area of the membrane then becomes unavailable for separation, adversely affecting the separation efficiency of the membrane, until sufficient pressure is generated to displace the air.

Accordingly, a method for priming a membrane separator is provided that more uniformly wets the membrane surface by providing a more uniform air-fluid interface during priming. To this end, priming fluid is introduced into the separator so that it works against the force of gravity as the fluid-air interface advances in an upward direction across the surface of the membrane. This helps to ensure a more uniform wetting of the membrane, as the air displaced during priming is able to move in a single direction without being trapped as the air-fluid interface advances across the membrane.

Thus, according to this alternate method for priming, the priming fluid is introduced into the separator through a port at the bottom of the separator. The priming solution advances upwardly in the housing of the separator against the force of gravity to wet the surface of the membrane, with the air being expelled from the separator through a port at the top of the separator. While this "bottom to top" priming is described in the context of a spinning membrane separator, it is also applicable to any type of membrane separator that requires fluid priming prior to use.

With reference to FIGS. 9 and 12, the separator 108 is oriented vertically, so that the membrane separator and housing are relatively rotatable to one another about a generally-vertical axis, with the port for receiving the whole blood at the top of the separator and the ports through which the separated RBCs and plasma exit at the bottom of the separator. Thus, according to one way for performing this alternative priming method, and with reference to FIGS. 1 and 2, the priming solution may be introduced through one of the exit orifice 34 or plasma outlet orifice 46 of the spinning membrane separator 10, while air is expelled through the inlet orifice 22.

Figure 12A:
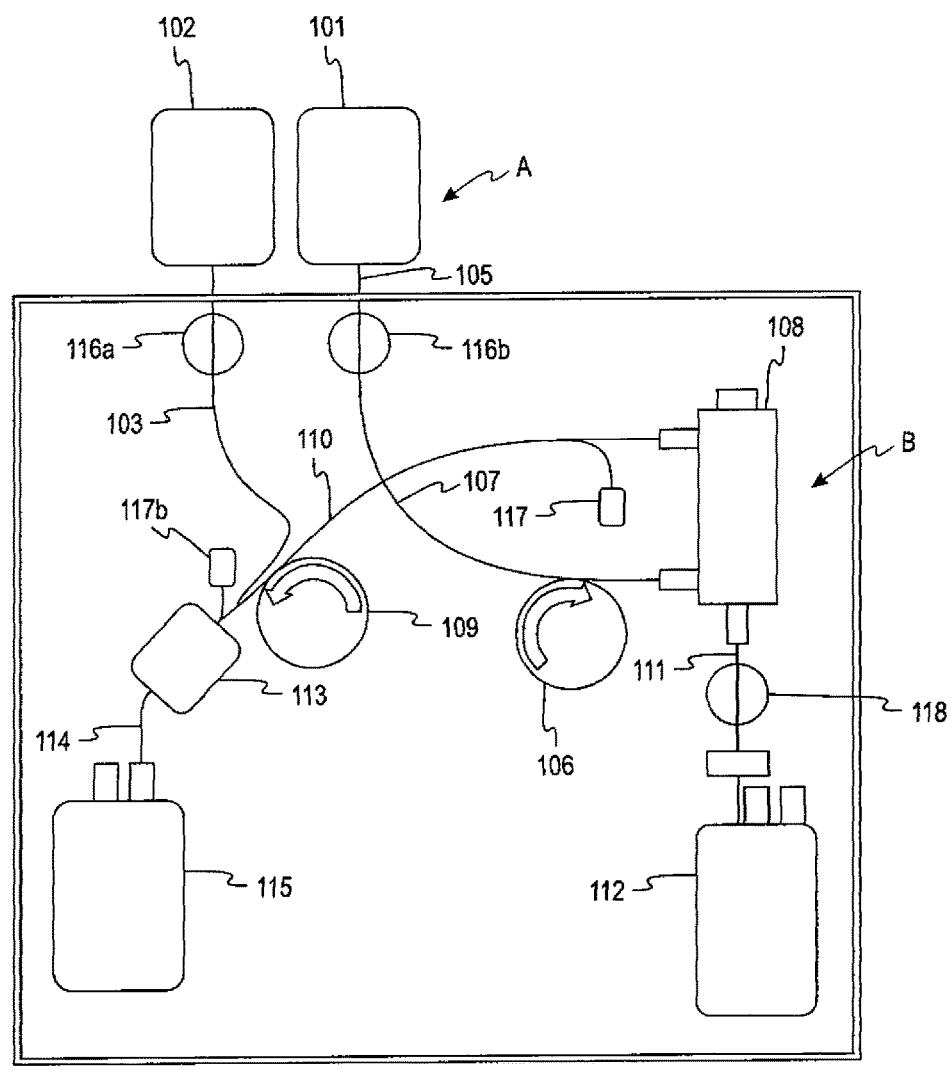
FIG. 12A is a schematic view of a further alternate embodiment, similar to FIG. 12.
Figure 12B:
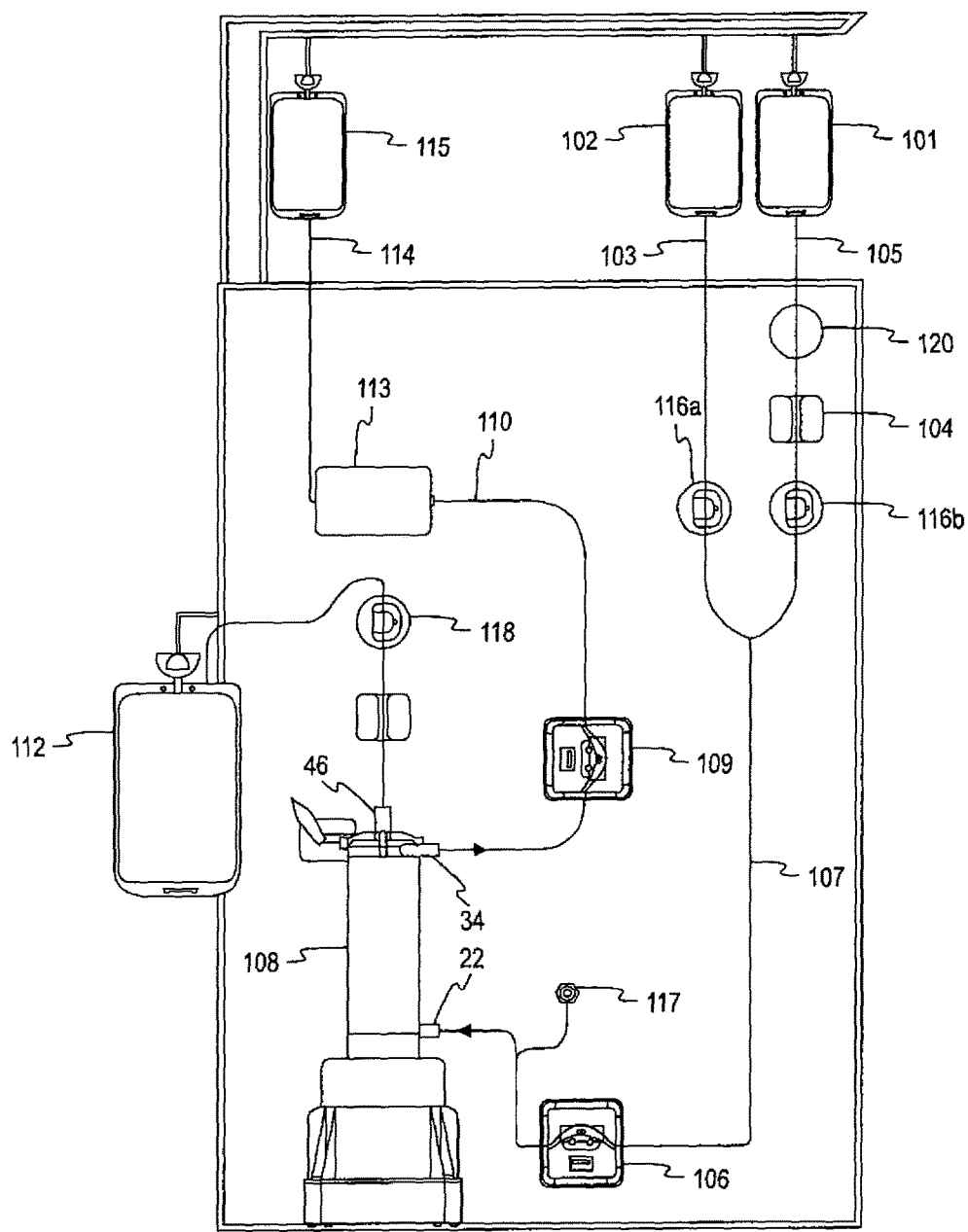
FIGS. 12B-12E are schematic views of a further embodiment alternative to those of FIGS. 9, 11 and 12.
Figure 12C:
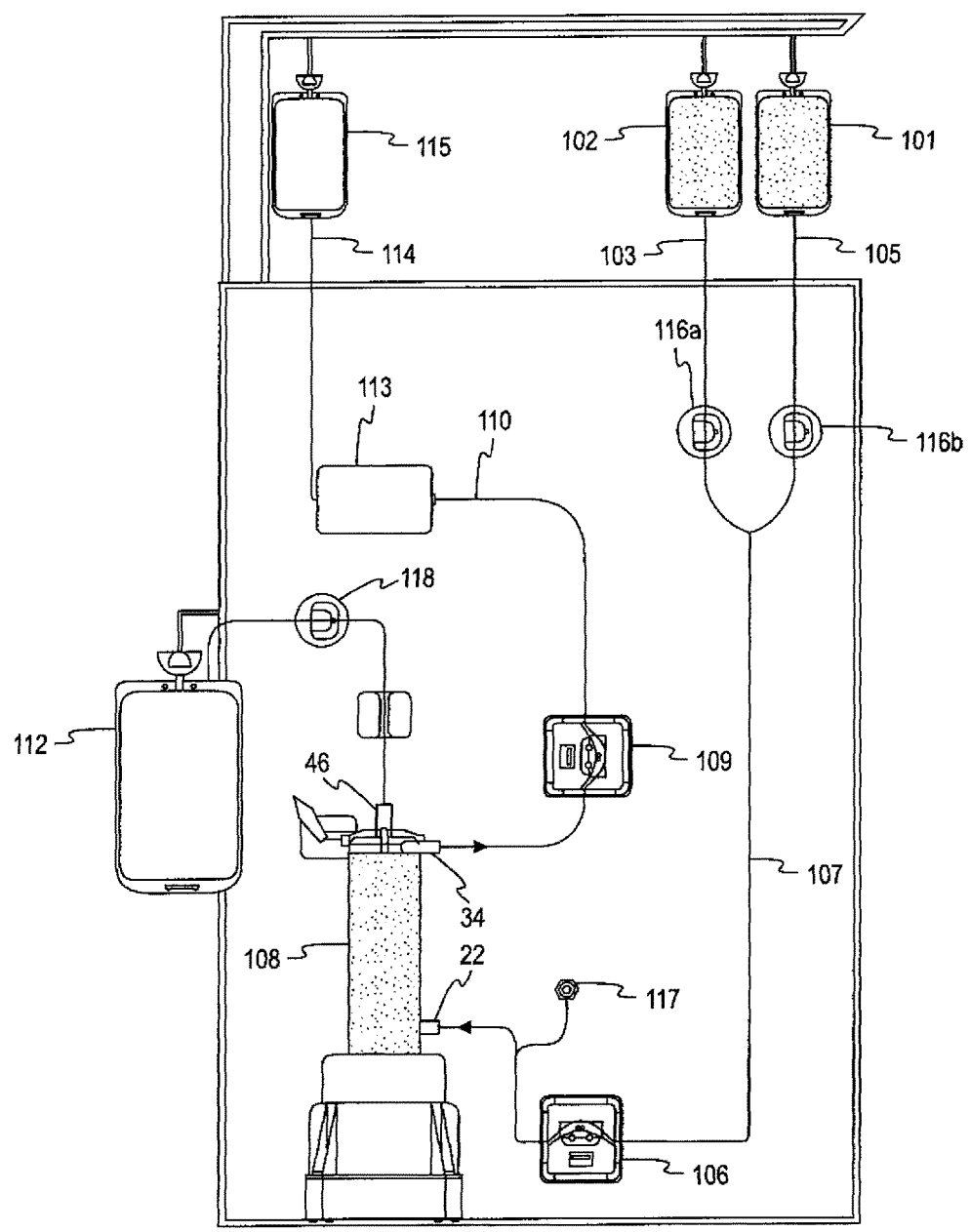
Figure 12D:
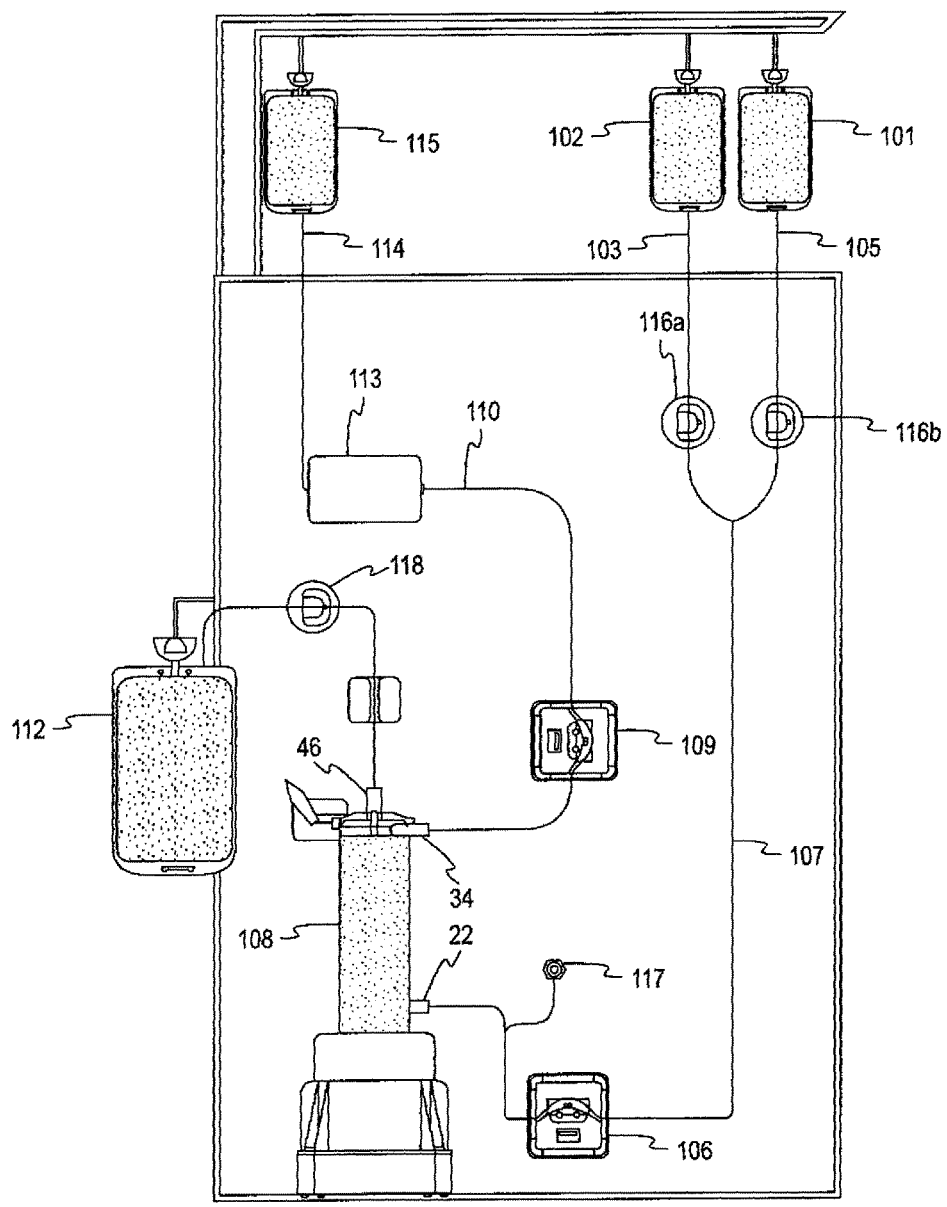
Figure 12E:
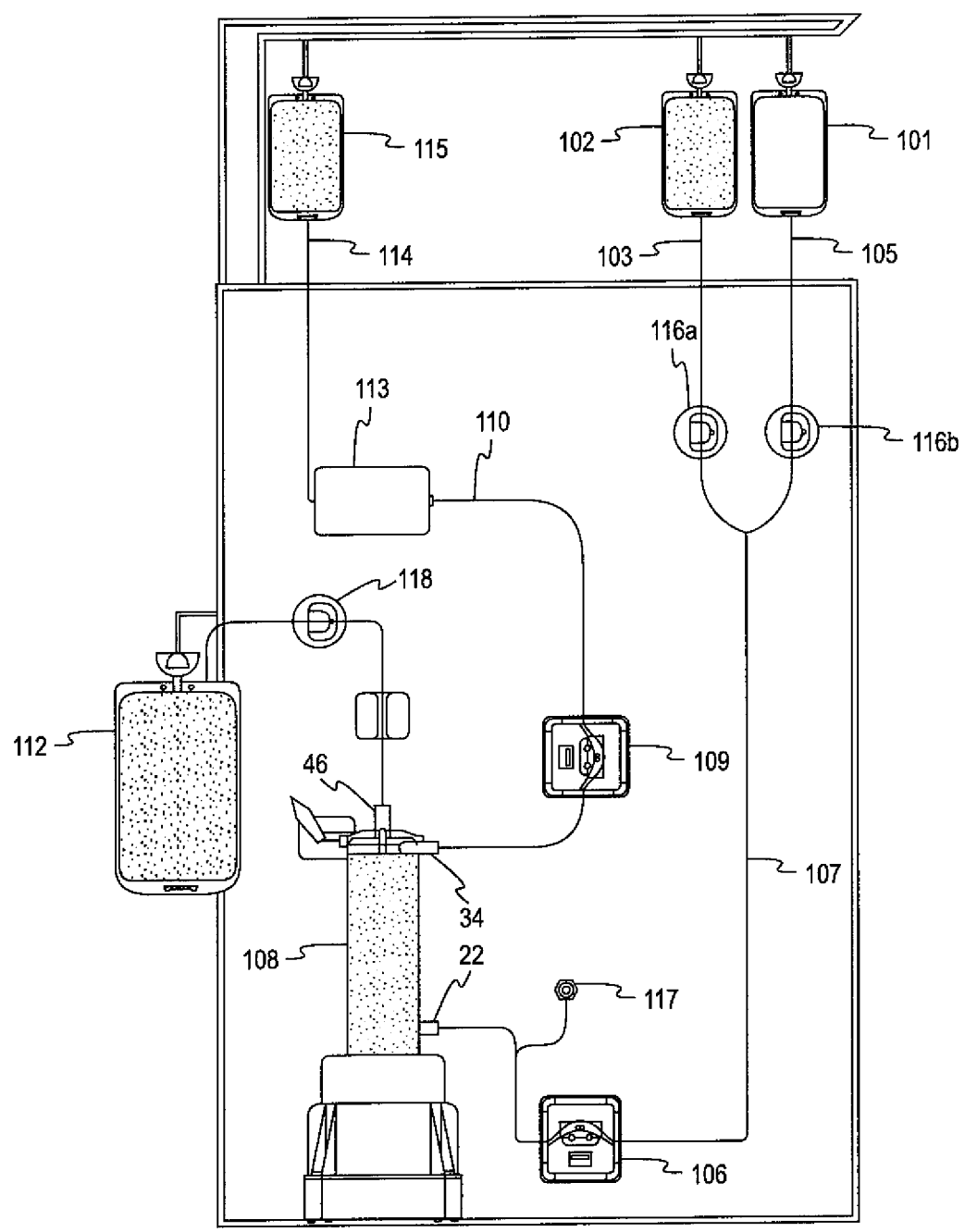
Figure 13:
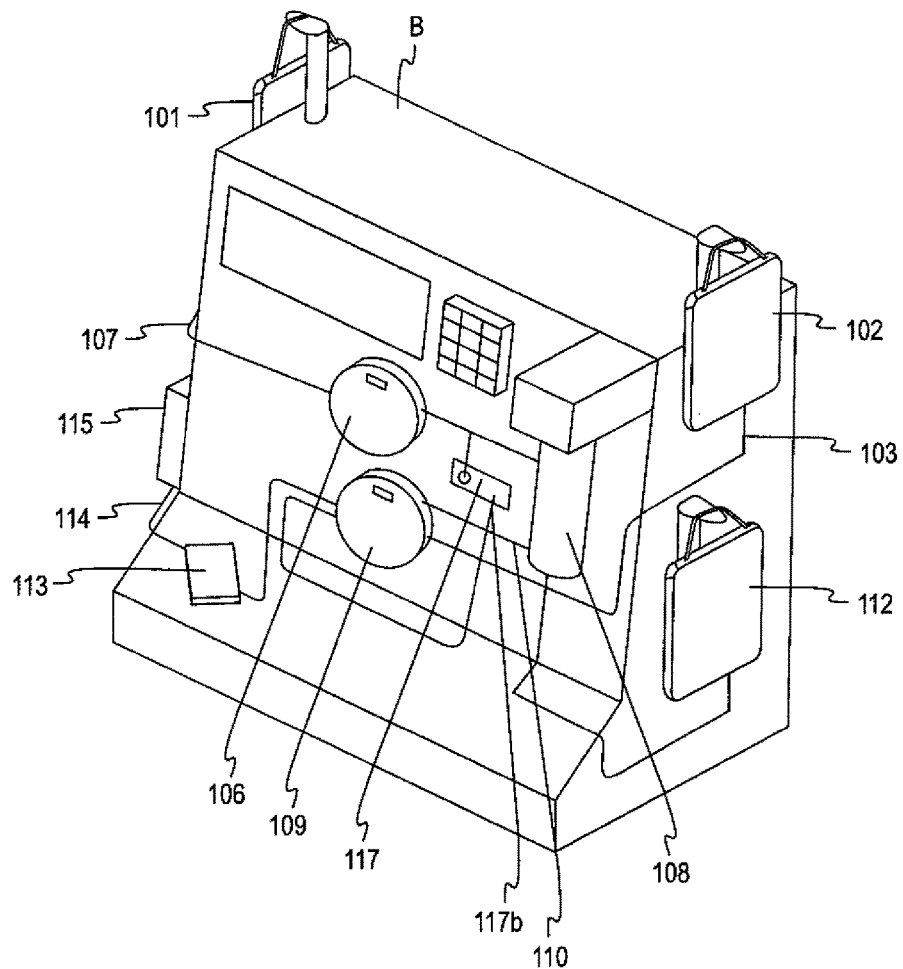
FIG. 13 is a perspective view of a two-pump blood separation system such as that shown in FIGS. 9, 11, 12 and 12A.

According to another way for performing this alternative priming method, and as seen in FIG. 12B, separator 108 may be inverted or upturned for priming, so that the exit orifice 34 and plasma outlet orifice 46 are at the top of the separator 10, and the inlet orifice 22 is at the bottom of the separator 108. As also illustrated in FIG. 12B, the system includes a sterile dock device 120 to connect the whole blood bag 101 to the rest of the kit. The sterile dock device is explained in further detail in U.S. Provisional Application Ser. No. 61/578,690, filed Dec. 21, 2011, incorporated by reference herein and a copy of which is attached. As seen in FIG. 12C, the priming solution may be introduced through the inlet 22, with the fluid-air interface advancing upwardly and air being expelled through either or both of the exit orifice 34 and the plasma outlet orifice 46. After priming, separation of the whole blood may commence. To this end, the separator 10 may be returned to its original orientation, with the inlet orifice 22 at the top and the exit orifice 34 and plasma outlet orifice 46 at the bottom. Preferably the upside-down configuration of the spinning membrane 108 is maintained, and separation commences, as illustrated in FIG. 12D, until the whole blood bag 101 is emptied. The spinning membrane 108 is then preferably flushed with preservative additive solution (from container 102) pumped into the spinning membrane 108 through inlet orifice 22 to flow the red blood cells left in the spinning membrane 108 into the red blood cell collection container 115. The flush with additive solution is continued until the total volume of additive solution in the collection container 115 meets requirements.

A further alternative in which the "bottom to top" priming of the blood separator 108 described above may be used is shown in FIG. 12A. In contrast to FIG. 12, the inlet line 107 for the whole blood connects to the lower port of the separator 108 (to which the outlet line 110 had been attached in the embodiment of FIG. 12), while the outlet line 110 is connected to the port at the top of the separator 108 (to which the inlet line 107 had been attached in the embodiment of FIG. 12). To prime the system of FIG. 12A, clamp 116B is opened and pump 106 activated to flow whole blood (preferably with anticoagulant added) through the inlet line 107 so that it enters the separator 108 through the port at the lower end of the housing. As the whole blood fills the separator housing, air is expelled through the top port, to substantially eliminate all air from the device, and the filter membrane is wetted.

After priming is completed, the system continues to operate as shown in FIG. 12A to separate the whole blood into plasma, received in container 112, and red blood cells, received in container 115. At the end of the separation procedure, the separator may be rinsed with additive solution from container 102.

Figure 14:
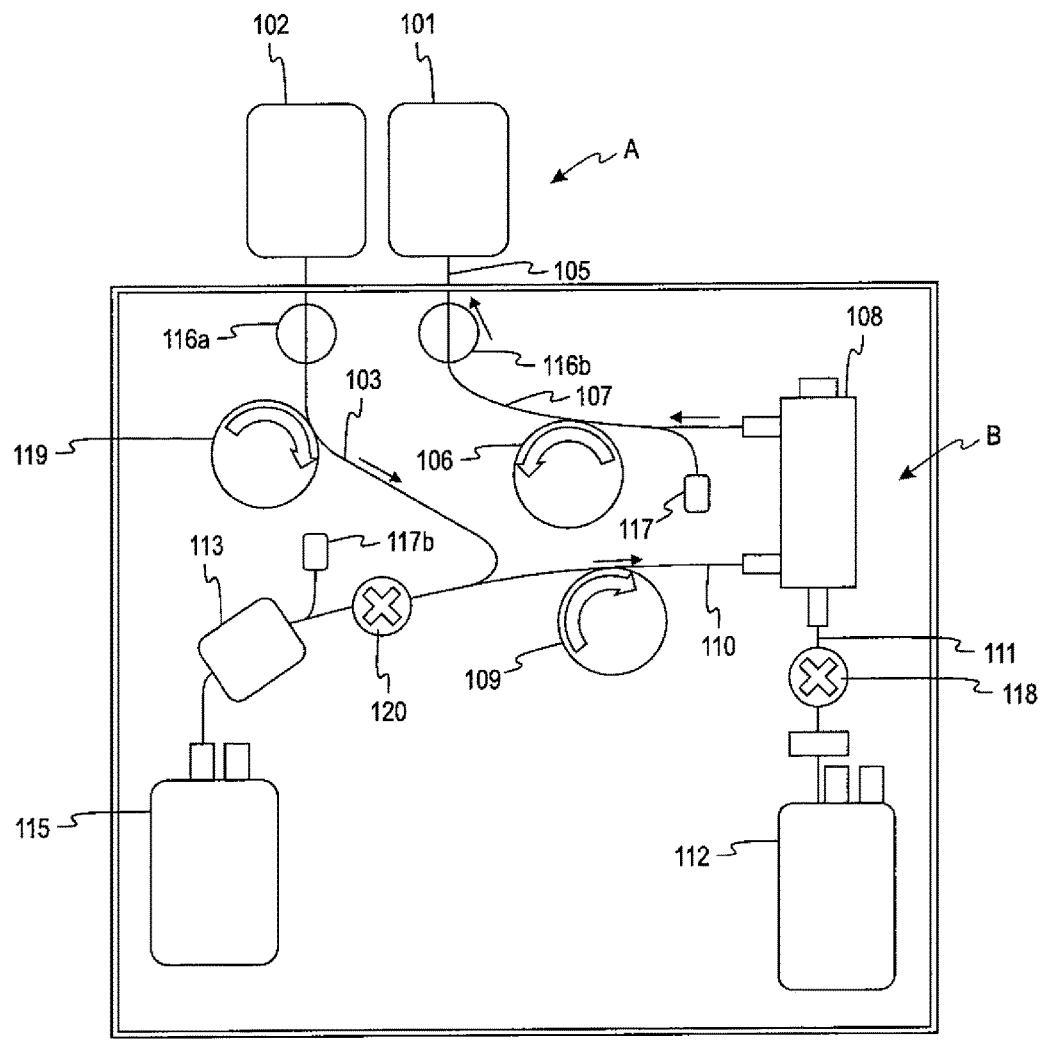
FIG. 14 is a schematic view of a further alternative similar to FIG. 12, except incorporating three pumps, illustrating the system in the priming phase.
Figure 15:
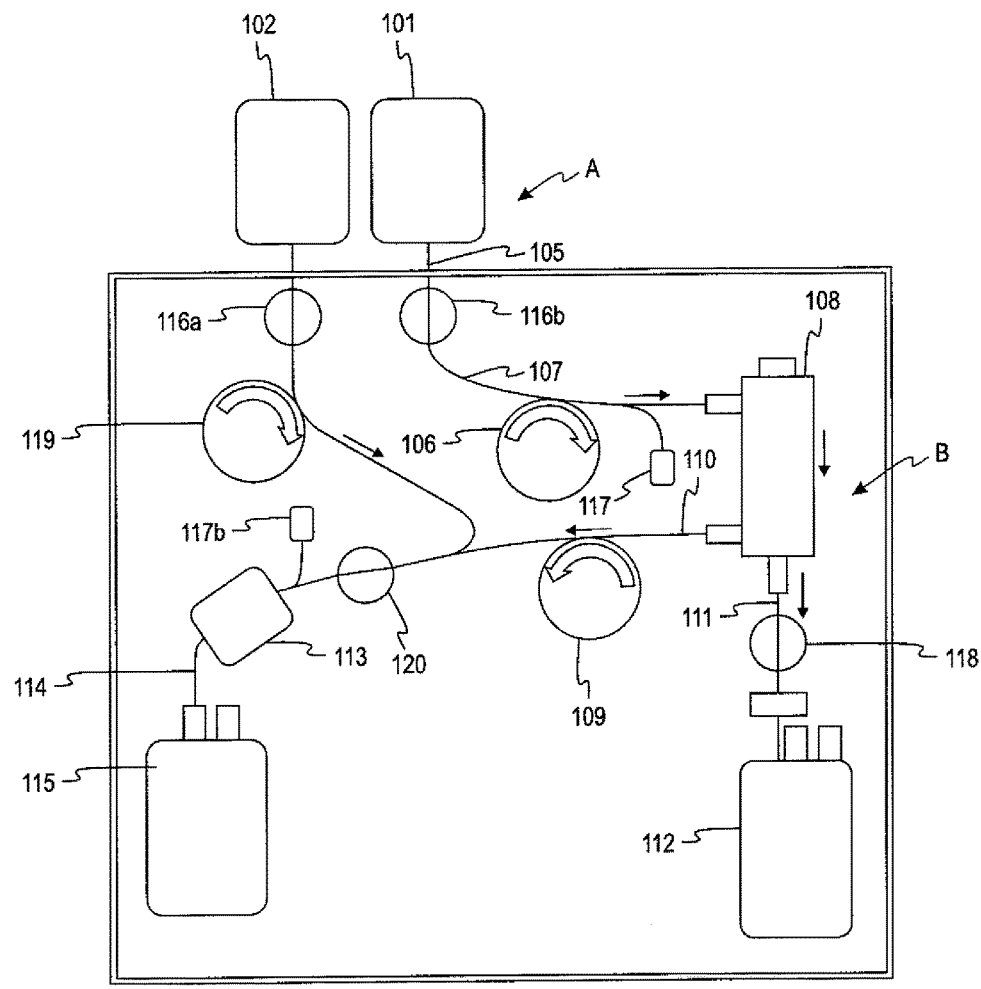
FIG. 15 is a schematic view of the system of FIG. 14 illustrating the system in the separation phase.

Turning to FIGS. 14 and 15, a further alternative blood separation system according to the present disclosure is shown. The system of FIGS. 14 and 15 is similar to that of FIGS. 9, 11, and 12 except that the durable module B includes a third pump 119 for selectively flowing additive solution to either the separator 108 during the priming phase (as shown in FIG. 14), or to the separated red blood cells during the separation phase (as shown in FIG. 15). The system of FIGS. 14 and 15 also includes a further clamp 120 for selectively permitting or preventing flow of fluid (separated red blood cells and additive solution) through the leukofilter 113 and into the red blood cell container 115. Prior to priming, clamp 120 could briefly remain open and pump 109 could pump residual air from container 115 and filter 113, minimizing the amount of air remaining in container 115 at the end of the procedure. Like FIG. 12A, the system of FIGS. 14 and 15 employs bottom to top priming of the separator 108, except using additive solution for the priming fluid instead of whole blood. During priming of the system, as shown in FIG. 14, air from the disposable system A is pushed to the whole blood container 101.

During the separation phase, the system is operated as shown in FIG. 15. At the conclusion of the separation phase, additive solution is pumped to the separator 108 (as shown in the prime phase illustrated in FIG. 14) to rinse the separator.

Figure 15A:
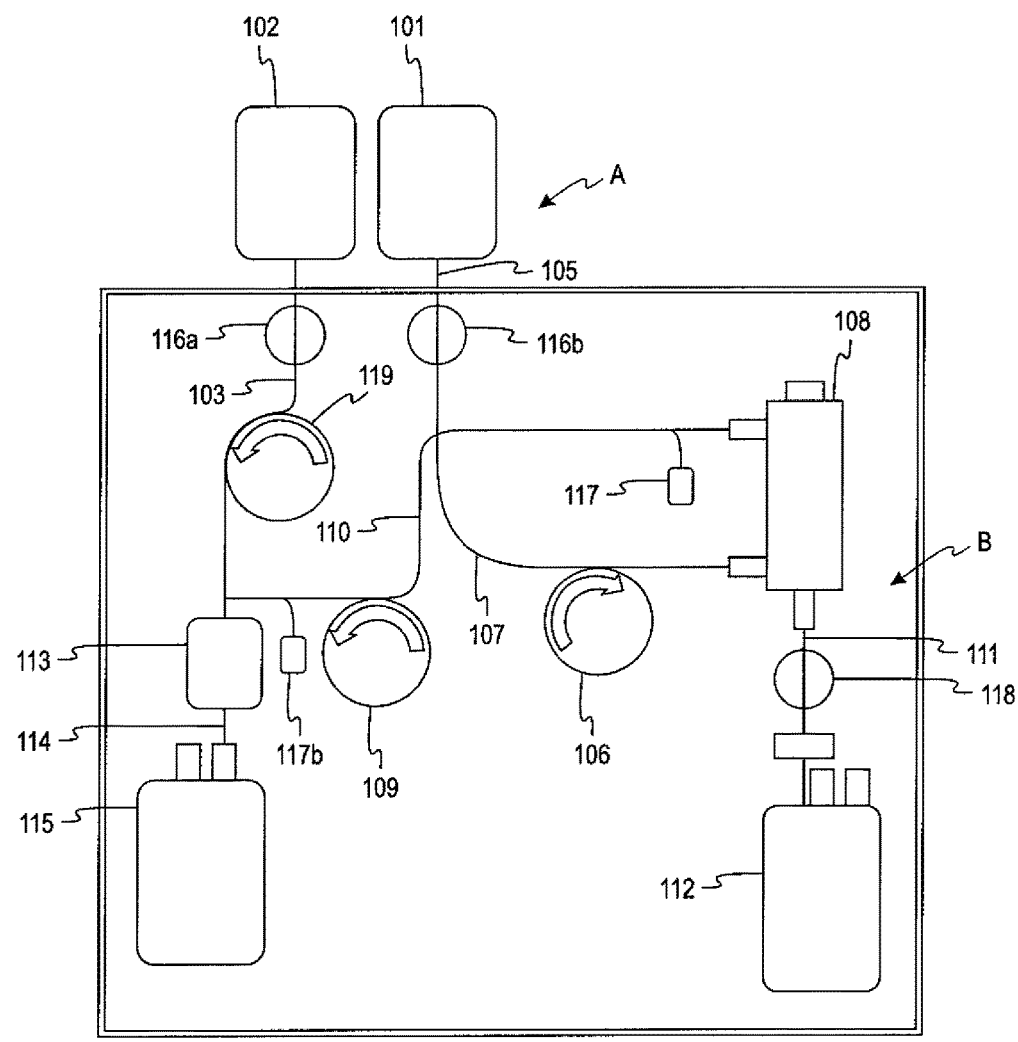
FIG. 15A is a schematic view of a further alternative three-pump system, similar to FIGS. 14 and 15.

Turning to FIG. 15A, a further alternative system is shown. The system of FIG. 15A is like that of FIGS. 14 and 15, in that the reusable component B comprises three pumps 106, 109, and 119. However, the system of FIG. 15A is similar to that of FIG. 12A, in that the inlet line 107 for the whole blood is connected to the port at the bottom of the separator 108, while the outlet line for the separated red blood cells is connected to the port at the top of the separator. Thus, the system of FIG. 15A, whole blood is used for priming the system, similar to the system of FIG. 12A.

Figure 15B:
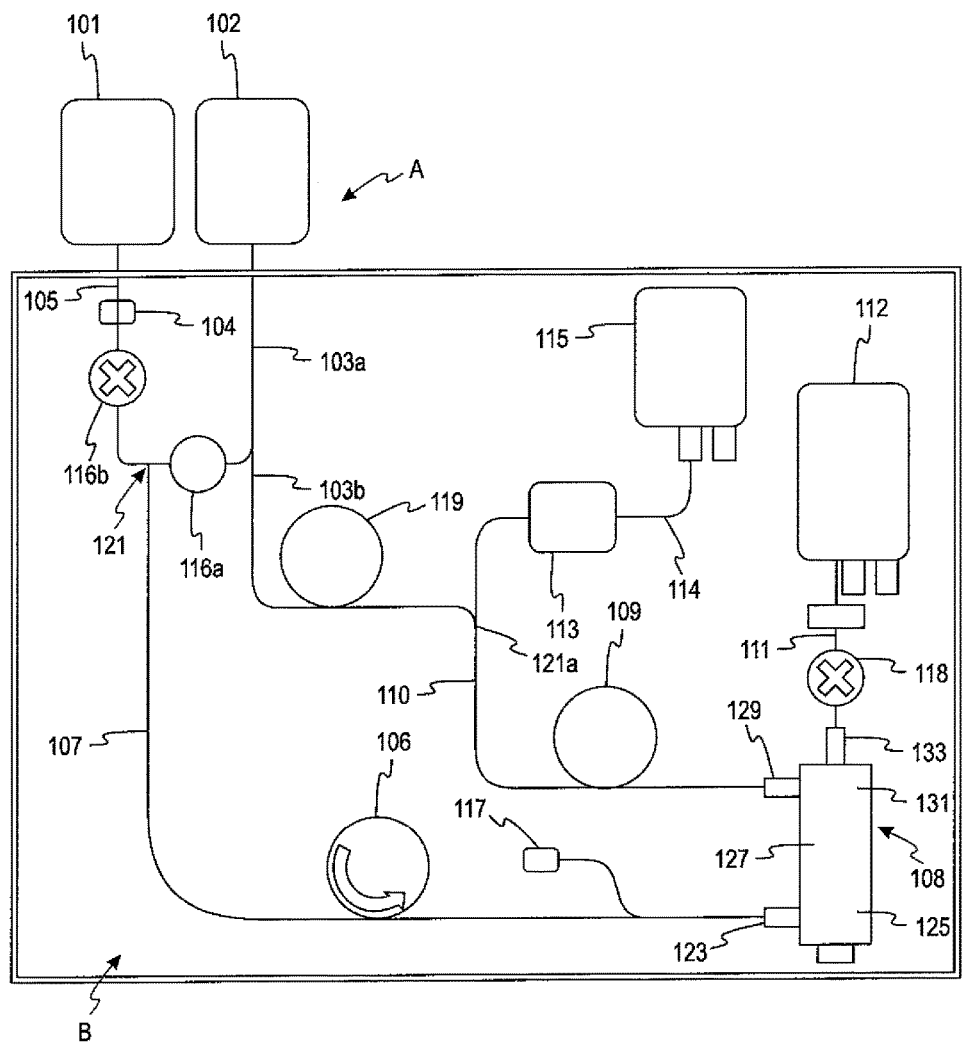
FIG. 15B is a schematic view of yet a further alternative three-pump system.
Figure 15C:
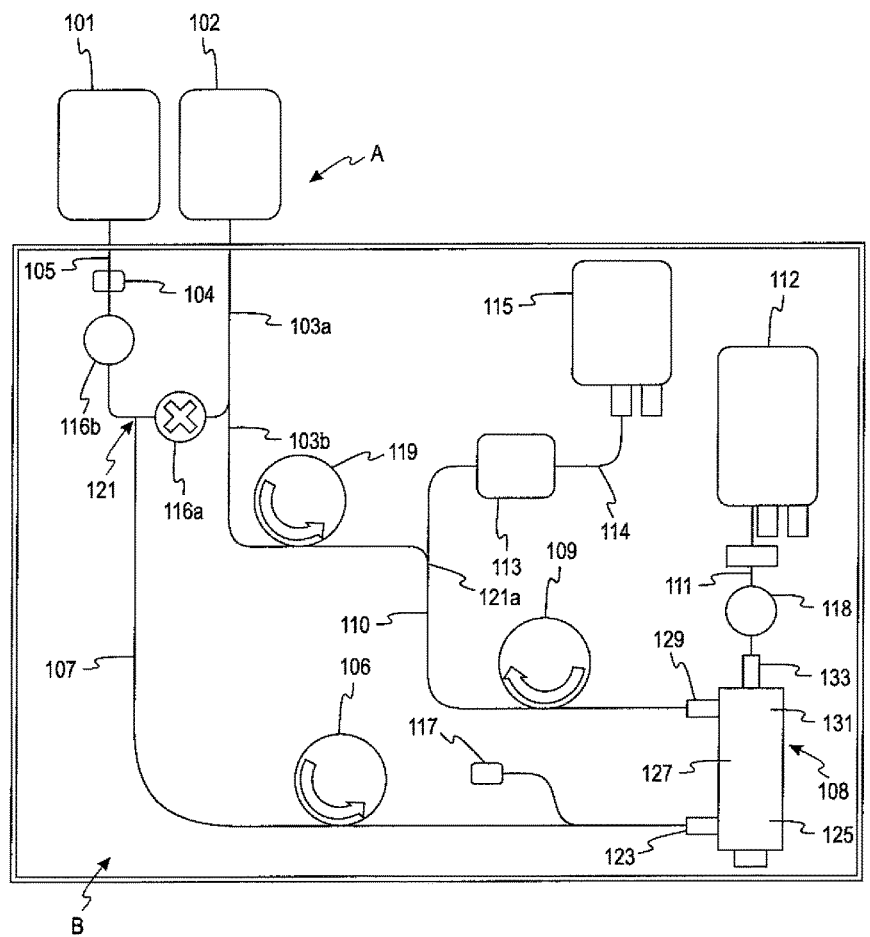
FIG. 15C is a schematic view of the system of FIG. 15B illustrating the system in the separation and collection phase.

FIGS. 15B and 15C show yet another alternative fluid processing circuit including a three-pump system. The disposable circuit A includes a whole blood container 101, an additive solution container 102 (such as a cell preservation solution container), a blood component separator 108 (shown in the operating position), plasma collection container 112, a leukoreduction filter 113, and red cell collection container 115.

A whole blood fluid flow path 105 is attached to the whole blood collection container 101 and provides a flow path between the whole blood container 101 and a junction 121 which also is connected to flow path 103a for additive solution. First flow path 103a for additive solution extends from additive solution container 102 to junction 121. From junction 121, whole blood flow path 105 extends through a flow path 107, which is a continuation of whole blood flow path 105, to an inlet port 123 located in a lower end region 125 of the housing 127 of separator 108.

Separator housing 127 has an outlet port 129 in the upper end region 131 thereof that communicates with the gap between the housing and rotor and with concentrated red blood cell flow path 110 for withdrawing concentrated red cells from the separator gap. In addition, separator 108 includes another outlet 133 also located in upper region 131 of housing 127 which communicates with the side of the membrane facing away from the gap (for example, the interior of the rotor) and communicates with plasma flow path 111.

For reducing the number of leukocytes that may be present in the separated red cells, the fluid circuit includes a leukocyte reduction filter 113 connected to red blood cell flow path 110 between outlet 129 and red blood cell collection container 115, i.e., downstream of separator 108 and upstream of container 115. The leukoreduction filter may be of any suitable well known construction for removing leukocytes from concentrated red cells without unduly causing hemolysis of red cells or reducing the number of red cells in the collected product. A second flow path for additive solution 103*b* connects additive solution container 102 to red blood cell flow path 110 at junction 121*a* which is upstream of leukoreduction filter 113. The concentrated red cells flow from outlet 129 through red blood cell flow path 110, where the red blood cells are combined with additive solution, to leukoreduction filter 113. The red blood cells then flow from the leukoreduction filter 113 through a continuation 114 of the concentrated red cell flow path 110 into storage container 115 which may be of any suitable plastic material compatible with red cell storage.

The fluid processing circuit also includes a whole blood inlet clamp 116*b* which is operated to control fluid from the whole blood container 101 and additive solution clamp 116*a* for controlling flow of additive solution from the solution container 102 to whole blood flow path 105. The fluid processing circuit preferably includes a hematocrit sensor 104 for detecting the hematocrit of the whole blood flowing from the whole blood container 101. The hematocrit detector may be of any suitable design described above. For controlling flow of whole blood and/or additive solution into the separator, the fluid processing circuit includes an inlet pump 106, which may be of any suitable construction, and may be, for example, a peristaltic type pump which operates by progressive compression or squeezing of the tubing forming the whole blood flow path into the separator, a flexible diaphragm pump or other suitable pump. Optionally, a pressure sensor 117 communicates with the whole blood flow path 107 between the pump 106 and the separator 108 to determine the inlet pumping pressure. The sensor may output to the control system to provide an alarm function in the event of an over-pressure condition or an under-pressure condition or both.

To control the flow rate of concentrated red cells from the separator 108, the reusable module B also includes an outlet pump 109 that is associated with the red blood cell outlet flow path 110, and functions in a manner similar to that described with respect to inlet pump 106. It also may be of any suitable construction such as a peristaltic pump, a flexible diaphragm or other suitable pumping structure. The reusable module B also includes a third pump 119 for selectively flowing additive solution through the second flow path 103*b* for additive solution and into the red blood cell flow path 110 where the additive solution is combine or mixed with the separated red blood cells prior to being passed or pumped through leukoreduction filter 113 and into red blood cell container 115. The addition of additive solution to the separated red blood cells in red blood cell flow path 110 dilutes the red blood cells to a lower hematocrit before passage through leukoreduction filter 113. Dilution of the separated red blood cells decreases filter pressure which reduces the risk of hemolysis of red blood cells.

Turning now to the processing of whole blood in the system illustrated in FIGS. 15B and 15C. Similar to FIG. 12A, the system of FIGS. 15B and 15C employs bottom to top priming of the separator 108, except that additive solution is used for the priming fluid instead of whole blood. Turning to FIG. 15B, during priming, clamp 116*b* is closed to prevent whole blood from flowing out of whole blood container 101 and into whole blood flow path 105. Clamp 116*a* is opened and additive solution is removed from additive solution container 102 by inlet pump 106 until additive solution flow path 103*a*, whole blood flow path 105/107 and the spinning membrane device of separator 108 are completely filled. To ensure proper priming, inlet pump 106 may move both clockwise and counterclockwise during the prime. During priming of the system, clamp 118 is closed and air from the disposable system A is pushed to the red blood cell container 102.

Referring to FIG. 15C after the system is substantially primed, clamp 116*a* is closed and clamp 116*b* is opened. Whole blood will then be pumped through the whole blood flow path 105 and whole blood continuation flow path 107 by the inlet pump 106 into separator 108. Inlet pump 106 flow rates can vary for example, from about 10 ml/min to 150 ml/min depending on desired product outcomes for a specific procedure. As the whole blood leaves the whole blood container 101 it will pass through the whole blood hematocrit detector 104 which will generate an estimation of the whole blood hematocrit through IR LED reflectance measurements.

After whole blood has filled the separator 108, the system will begin to draw plasma from the separator which separates the whole blood entering the spinning membrane device into a red cell concentrate and virtually cell free plasma. Packed red blood cells at approximately 80-85% hematocrit will flow out of outlet port 129 of separator 108 and be pumped through the red cell flow path 110. Additive solution is pumped by pump 119 into red blood cell flow path 110 where the additive solution mixes with and preferably dilutes the red blood cells in flow path 110. Outlet pump 109 and/or pump 119 force the packed red blood cells diluted to a lower hematocrit with the additive solution through the leukoreduction filter 113. The red cells and additive solution exit leukoreduction filter 113, flow through the red blood cell line 114 and into the red blood cell collection container 115.

Additionally, clamp 118 will be opened and throughout the procedure, plasma will flow through the plasma flow path 111 into the plasma bag 112 at a flow rate equal to the difference between the inlet pump 106 flow rate and outlet pump 109 flow rate as described above. The pressure across the membrane generated by the offset in flow rates is monitored by the pressure sensor 117. The pressure measurements are used to control the plasma flow rate as described above.

The system will continue to separate packed red blood cells and plasma until the whole blood bag 101 is empty as detected by air passing through the whole blood hematocrit detector 104. At this point the clamp 116*b* will be closed and the additive solution line will be opened by clamp 116*a* to start the solution rinse or flush. During the solution rinse, additive solution will be removed from additive solution container 102 and pumped into separator 108 by the inlet pump 106. The plasma flow path 111 is closed by the plasma clamp 118 during the solution rinse. The solution rinse is used to flush any red blood cells remaining in the separator into red blood cell flow path 110, through leukoreduction filter 113 and into red blood cell collection container 115.

Either simultaneous with the solution rinse or after the solution rinse, additive solution may be pumped by pump 119 through second flow path 103*b*, red blood cell flow path 110, and leukoreduction filter 113 to flush remaining red blood cells from filter 113. If the flushing process occurs after solution rinse, clamp 116*a* is closed to direct the additive solution only into flow path 103*b*. As the additive solution passes through leukoreduction filter 113, the additive solution flushes or rinses red bloods cells from the filter and into red blood cell collection container 115. Additive solution flow or flush rates may vary for example, from about 10 ml/min to 150 ml/min. Additionally, the flush rate may be constant during flushing or may be increased or decreased.

In the blood separation system illustrated in FIGS. 15B and 15C and other separation systems (including backroom and inline systems), red blood cells remain in the leukoreduction filter after the whole blood separation process and red blood cell collection processes are completed. As described above, in order to collect the remaining red blood cells, additive solution is passed through the leukoreduction filter to flush or rinse the remaining red blood cells from the leukoreduction filter. Such flushing with additive solution also may increase the additive solution volume in the collected red blood cell product, if such increase in additive solution is desired or required to meet product requirements.

If the flow or flush rate of the additive solution it too great during the flushing process, hemolysis of the red blood cells being flushed from the filter may occur. Filter hemolysis can occur anytime too high of a concentration of red blood cells is forced through the membrane of the filter at too fast of a rate. For example, after the separation and collection processes of red blood cells have been completed, the residual red blood cells remaining in the filter may be highly packed and have a hematocrit between about 70% and about 87%. If the flow rate or flush rate of the additive solution used to flush the filter is too high, pressure will build within the filter resulting in a high concentration of red blood cells being forced through the filter, resulting in hemolysis of the red blood cells. One way to help prevent hemolysis is to use an additive solution flush rate that is the same or similar (e.g., slightly lower or higher) to that of the red blood cells flow rate during separation and collection. In one embodiment, the red blood cell flow rate and the additive solution flush rate are kept constant at about 22 ml/min and the amount of additive solution used for flushing is between about 60 ml and about 80 ml. At a flush rate of about 22 ml/min it could take up to about 4 minutes or longer to complete the flushing process.

In an alternative embodiment, it has been found that the time it takes to flush the filter may be shortened by starting at an initial additive solution flow or flush rate and then continuously or gradually increasing the flush rate as the filter is being flushed. As additive solution pushes or flushes remaining red blood cells out of the filter, the hematocrit of the red blood cells within the filter decreases or decays. When the hematocrit of the red blood cells decreases within the filter, the flush rate of additive solution through the filter may be increased with little risk of increasing hemolysis. The increase of additive solution flush rate may be gradual (step-wise increases) or continuous. The timing and amount of flush rate increase may be based on one or more factors or measurements, including but not limited to, the hematocrit of the red blood cells in the filter, the amount of hemolysis at the various flush rates and/or the pressure within the filter. The factors may be employed as a predictor used to develop a pre-determine flush rate increase schedule/program or may be measured in real-time wherein the flush rate is increased based on real-time measurements. The pump used to pump the additive solution through the filter during flushing may be any suitable variable flow pump. Such pumps may include, but are not limited to, peristaltic or flexible diaphragm pumps.

In one exemplary embodiment, a desired flush rate increase is determined for a particular filter type or design from a correlation or relationship between hemolysis, hematocrit and flush rate of the additive solution through the filter. In this embodiment, a first correlation is made between selected flush rates and the amount of hemolysis that occurs at different hematocrit concentrations for each of the selected flush rates. Hemolysis may be measured by any suitable method and in one embodiment, for example, is measured by the concentration of plasma hemoglobin (PLH) of the supernatant of the red blood cell product exiting the filter. The first correlation can be used to predict if use of a selected flush rate would result in a tolerable amount of hemolysis at a given hematocrit concentration. More particularly, the correlation is used to determine the hematocrit to which the red blood cells within the filter would have to decrease to before the additive solution flush rate could be increased while maintaining an acceptable amount of hemolysis.

A second correlation is made between the selected flush rates and the decrease or decay of hematocrit concentration over time at the selected flush rates. This second correlation can be used to predict the time required to dilute the red blood cell concentration within the filter to a particular hematocrit for a given flush rate. As described in more detail in the example below, knowing that a particular hematocrit and flush rate results in an acceptable the amount of hemolysis and the time required at a particular flush rate to decrease the red blood cell concentration to that particular hematocrit, allows for the flush rate to be ramped up each time a particular hematocrit is reached.

EXAMPLE

The following non-limiting Example illustrates various features and characteristics of the present subject matter, which is not to be construed as limited thereto.

In this Example, tests were conducted to determine a first correlation or relationship between selected additive solution flush rates and the amount of hemolysis that occurs at different hematocrit concentrations for each of the flush rates, and to determine a second correlation between the selected flush rates and the decrease or decay of hematocrit concentration over time at each of the selected flush rates. As explained in more detail below, the first and second correlations were then used to determine flush rate increases during filter flushing.

Figure 15D:
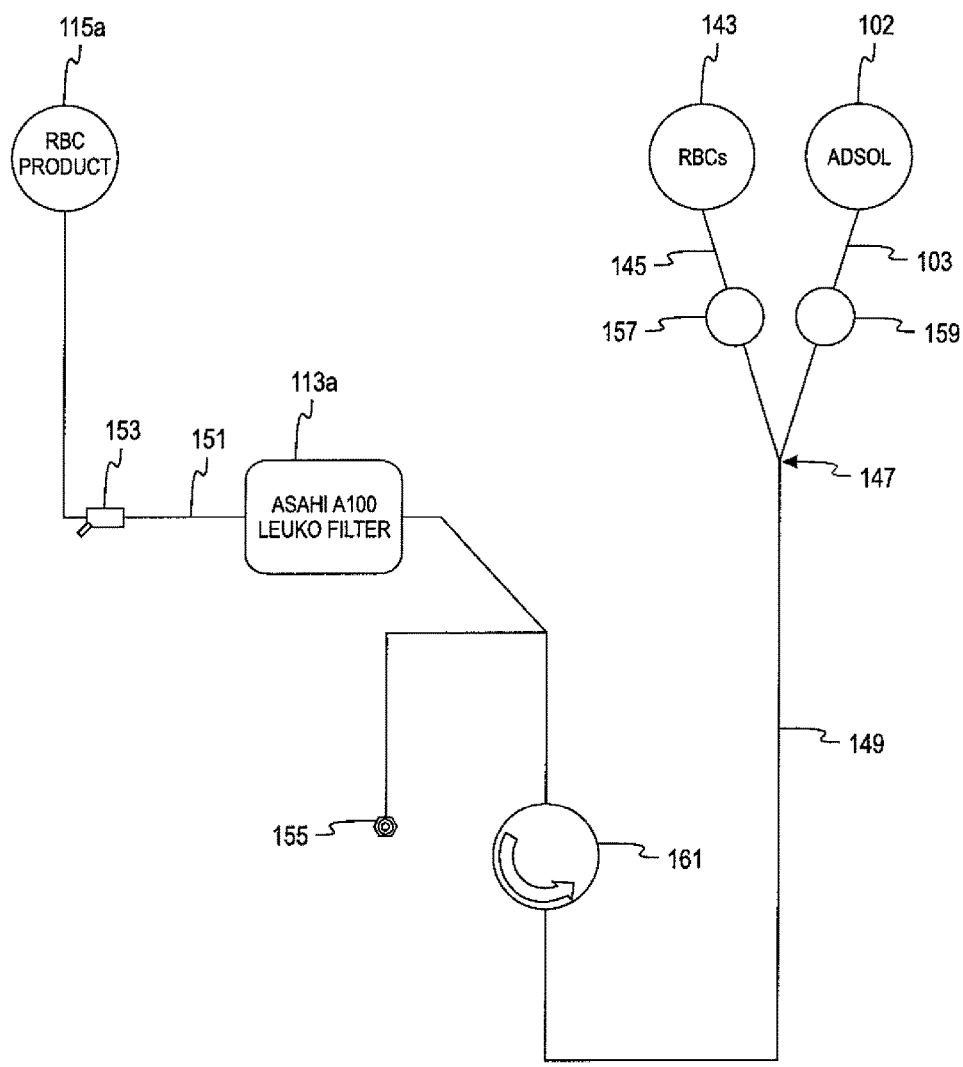
FIG. 15D is a schematic view of the testing system used in the Example.

The system schematically illustrated in FIG. 15D was used to conduct each of the tests of this Example. The system includes a red blood cell container 143 including a supply of red blood cells at an initial hematocrit of at least 85% for the tests run in this Example. The system also included an additive solution container 102, a leukoreduction filter 113a and a red blood cell collection container 115a. In each run, an Asahi Sepacell A-100 leukoreduction filter (supplied by Asahi Medical Co. of Japan) was used as the filter and Adsol (supplied by Baxter International of Illinois) was used as the additive solution.

A red blood cell flow path 145 was attached to the red blood cell supply container 143 and provided a flow path to junction 147 which was connected to an additive solution flow path 103. Red blood cell clamp 157 controlled the flow of red blood cells from red blood cell supply container 113. From junction 147, red blood cell flow path 145 extended through flow path 149 to leukoreduction filter 113a. Additive solution flow path 103 was attached to additive solution container 102 and provided a flow path to junction 147. Additive solution clamp 159 controlled the flow of additive solution from additive solution supply container 102. An M2 pump 161 pumped red blood cells and additive solution through flow path 149 and leukoreduction filter 113a. Flow path 151 connected leukoreduction filter 113a to red blood cell collection container 115a. An in-line sample site 153 was located in flow path 151 for taking samples during flushing of the leukoreduction filter 113a. A pressure sensor 155 was located upstream of the filter 113a for monitoring the pressure in the system.

During each run, red blood cell clamp 157 was opened and additive solution clamp 159 was closed so as to flow red blood cells through flow path 145 and 149. Pump 161 pumped the red blood cells through the leukoreduction filter 113a at a rate of 22 ml/min. Once the red blood cell supply container 143 was empty, red blood cell clamp 157 was closed and additive solution clamp 159 was opened to allow the additive solution to flow through flow path 103 wherein the pump rate was set at a selected flush rate for the particular run. After the additive solution started to be pumped through the leukoreduction filter 113a to flush the filter in-line samples of the red blood cell/additive solution mixture exiting the leukoreduction filter 113a were continuously taken in 5 ml test tubes at in-line sample site 153. The hematocrit and hemolysis of each sample were then measured. Hematocrit was measured by a spun-hematocrit test and hemolysis was measured by the concentration of plasma hemoglobin in the supernatant (mg/dl). The tables below list the results for each flush rate tested. In the test results, the normalized hematocrit was calculated by dividing the measured hematocrit of the sample by the initial hematocrit of the red blood cells supply and multiplying the result by 100.

TABLE 1

Adsol Flush Rate 22 ml/min
Initial Red Blood Cell Supply Hematocrit = 89.25

| Time (s) | HCT (%) | HCT (%) Norm | PLH (mg/dl) |
| --- | --- | --- | --- |
| 0 | 89.25 | 100 | 418.3 |
| 15.74 | 89.5 | 100.280112 | 399.7 |
| 25.74 | 65.5 | 73.38935574 | 120.9 |
| 33.64 | 45 | 50.42016807 | 64.3 |
| 42.84 | 39.25 | 43.97759104 | 46.6 |
| 55.04 | 33.5 | 37.53501401 | 35 |
| 66.74 | 31.75 | 35.57422969 | 20 |
| 79.44 | 22 | 24.64985994 | 20.3 |
| 94.84 | 18 | 20.16806723 | 15.2 |
| 117.24 | 14.15 | 15.85434174 | 12 |

TABLE 2

Adsol Flush Rate 30 ml/min
Initial Red Blood Cell Supply Hematocrit = 85

| Time (s) | HCT (%) | HCT (%) Norm | PLH (mg/dl) |
| --- | --- | --- | --- |
| 0 | 83.75 | 98.52941176 | 244.5 |
| 17.02 | 83.5 | 98.23529412 | 255.9 |
| 26.63 | 52.75 | 62.05882353 | 77.8 |
| 35.2 | 34.75 | 40.88235294 | 42.1 |
| 44.1 | 30.75 | 36.17647059 | 35.9 |
| 55.25 | 26.5 | 31.17647059 | 26 |
| 66.32 | 19.25 | 22.64705882 | 17.2 |
| 78.25 | 14.75 | 17.35294118 | 12.7 |
| 91.03 | 13.25 | 15.58823529 | 11.7 |
| 104.44 | 11.35 | 13.35294118 | 10.7 |

TABLE 3

Adsol Flush Rate 40 ml/min
Initial Red Blood Cell Supply Hematocrit = 85.5

| Time (s) | HCT (%) | HCT (%) Norm | PLH (mg/dl) |
| --- | --- | --- | --- |
| 0 | 83.5 | 97.66081871 | 426.1 |
| 13.98 | 83.25 | 97.36842105 | 402.4 |
| 22.89 | 54.5 | 63.74269006 | 143 |

TABLE 3-continued

Adsol Flush Rate 40 ml/min
Initial Red Blood Cell Supply Hematocrit = 85.5

| Time (s) | HCT (%) | HCT (%) Norm | PLH (mg/dl) |
| --- | --- | --- | --- |
| 29.72 | 35.25 | 41.22807018 | 64.5 |
| 37.8 | 27 | 31.57894737 | 46.7 |
| 46.36 | 24.5 | 28.65497076 | 41.3 |
| 55.31 | 21 | 24.56140351 | 28.7 |
| 64.2 | 15.65 | 18.30409357 | 19.7 |
| 74.22 | 10.65 | 12.45614035 | 13.4 |
| 84.13 | 7.9 | 9.239766082 | 9.7 |
| 95.2 | 6.15 | 7.192982456 | 7.5 |

TABLE 4

Adsol Flush Rate 50 ml/min
Initial Red Blood Cell Supply Hematocrit = 88.75

| Time (s) | HCT (%) | HCT (%) Norm | PLH (mg/dl) |
| --- | --- | --- | --- |
| 0 | 88.25 | 99.43661972 | 292.9 |
| 13.71 | 80.25 | 90.42253521 | 249.3 |
| 25.77 | 49 | 55.21126761 | 90.9 |
| 33.32 | 32.75 | 36.90140845 | 49.6 |
| 36.25 | 28.25 | 31.83098592 | 24.7 |
| 43.79 | 22.5 | 25.35211268 | 21 |
| 51.32 | 17.25 | 19.43661972 | 19.6 |
| 59.28 | 14.75 | 16.61971831 | 14.9 |
| 67.11 | 11.9 | 13.4084507 | 12.6 |
| 75.44 | 8.1 | 9.126760563 | 7.8 |

TABLE 5

Adsol Flush Rate 60 ml/min
Initial Red Blood Cell Supply Hematocrit = 86.5

| Time (s) | HCT (%) | HCT (%) Norm | PLH (mg/dl) |
| --- | --- | --- | --- |
| 0 | 85.5 | 98.84393064 | 320.7 |
| 13.78 | 74.75 | 86.41618497 | 290.7 |
| 19.66 | 38.25 | 44.21965318 | 56.8 |
| 23.84 | 31 | 35.83815029 | 40.7 |
| 29.74 | 28.5 | 32.94797688 | 37.9 |
| 36.88 | 24.75 | 28.61271676 | 28.1 |
| 44.03 | 16.1 | 18.61271676 | 16.9 |
| 50.69 | 12.2 | 14.10404624 | 11.3 |
| 58.19 | 9 | 10.40462428 | 8.9 |
| 66.21 | 7 | 8.092485549 | 7.2 |

TABLE 6

Adsol Flush Rate 70 ml/min
Initial Red Blood Cell Supply Hematocrit = 86.5

| Time (s) | HCT (%) | HCT (%) Norm | PLH (mg/dl) |
| --- | --- | --- | --- |
| 0 | 87.5 | 101.1560694 | 414.3 |
| 12.65 | 75.75 | 87.57225434 | 346.6 |
| 18.42 | 40.5 | 46.82080925 | 80.2 |
| 23.03 | 25 | 28.9017341 | 60.7 |
| 28.98 | 21.5 | 24.85549133 | 47 |
| 36.41 | 21.2 | 24.50867052 | 39.3 |
| 42.7 | 15.8 | 18.26589595 | 25.1 |
| 50.5 | 11.65 | 13.46820809 | 18.3 |
| 58.31 | 7.75 | 8.959537572 | 12 |
| 65.83 | 5.9 | 6.820809249 | 9.7 |

TABLE 7

Adsol Flush Rate 80 ml/min
Initial Red Blood Cell Supply Hematocrit = 88.75

| Time (s) | HCT (%) | HCT (%) Norm | PLH (mg/dl) |
|---|---|---|---|
| 0 | 90 | 101.4084507 | 692.8 |
| 11.21 | 71 | 80 | 399 |
| 16.18 | 36.5 | 41.12676056 | 116 |
| 21.19 | 23 | 25.91549296 | 55.8 |
| 26.56 | 19.75 | 22.25352113 | 47.4 |
| 33.58 | 20 | 22.53521127 | 41.6 |
| 41.06 | 13.25 | 14.92957746 | 23.5 |
| 46.9 | 10 | 11.26760563 | 16.6 |
| 53.54 | 6.65 | 7.492957746 | 11.5 |
| 61.11 | 4.45 | 5.014084507 | 9.2 |
| 68.06 | 4.4 | 4.957746479 | 8.3 |

TABLE 8

Adsol Flush Rate 90 ml/min
Initial Red Blood Cell Supply Hematocrit = 87.5

| Time (s) | HCT (%) | HCT (%) Norm | PLH (mg/dl) |
|---|---|---|---|
| 0 | 87.25 | 99.71428571 | 1224.6 |
| 9.53 | 80.5 | 92 | 1004.4 |
| 13.66 | 51.25 | 58.57142857 | 323.8 |
| 19.43 | 36 | 41.14285714 | 174.1 |
| 21.08 | 27 | 30.85714286 | 109.9 |
| 22.77 | 23 | 26.28571429 | 75.2 |
| 26.9 | 22.5 | 25.71428571 | 79.5 |
| 30.77 | 20.75 | 23.71428571 | 69.2 |
| 34.95 | 18 | 20.57142857 | 54.1 |
| 35.4 | 15 | 17.14285714 | 45.9 |
| 44.93 | 12.75 | 14.57142857 | 36 |

Figure 15E:
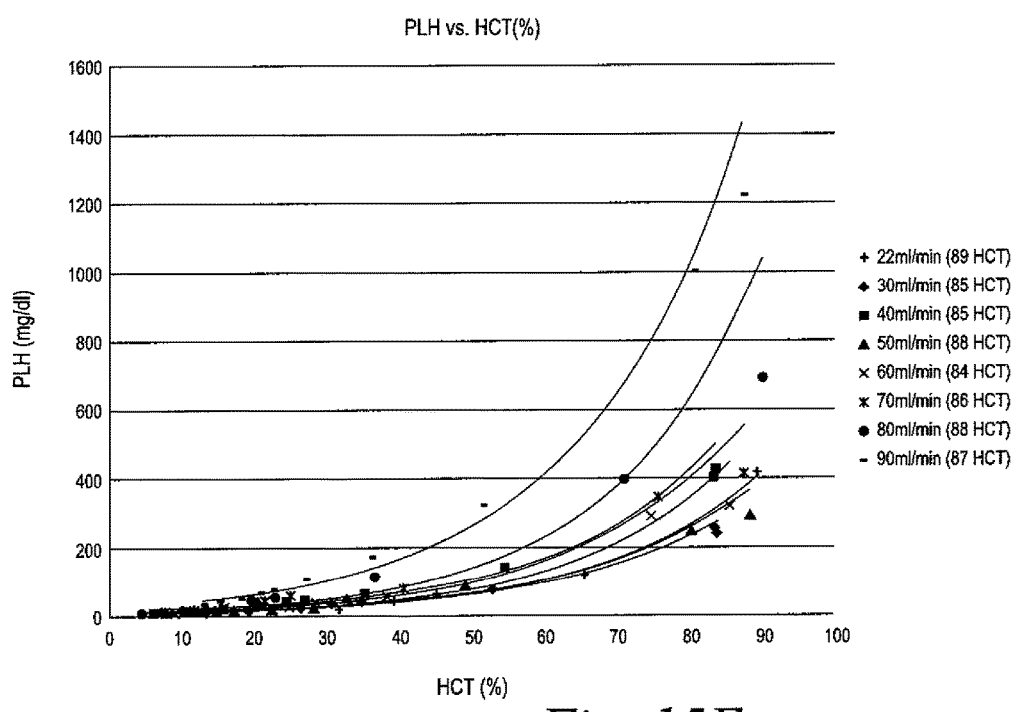
FIG. 15E is a graphical representation of the hemolysis vs. the hematocrit of the various tests of the Example.

The hemolysis (PLH) vs. hematocrit (HCT) for each test was plotted as shown in the graph entitled PLH vs. HCT of FIG. 15E. The data of each individual test for a selected flush rate was then fitted to a best fit curve. The equations of the best fit curve for each flush rate were determined and are listed below in Table 9. Given a desired amount of hemolysis, the equations below can be used to calculate the hematocrit that the red blood cells in the filter must be at before a particular flush rate may be used.

TABLE 9

| Flush Rate (ml/min) | HCT vs. PLH |
|---|---|
| 22 | HCT = ln(0.150*PLH)/0.0461 |
| 30 | HCT = ln(0.131*PLH)/0.0428 |
| 40 | HCT = ln(0.111*PLH)/0.0482 |
| 50 | HCT = ln(0.071*PLH)/0.0433 |
| 60 | HCT = ln(0.138*PLH)/0.0483 |
| 70 | HCT = ln(0.081*PLH)/0.0435 |
| 80 | HCT = ln(0.089*PLH)/0.0504 |
| 90 | HCT = ln(0.131*PLH)/0.038 |

For example, using the above equation for a flush rate of 30 ml/min, if the desired hemolysis (PLH) is 50 mg/dl, the hematocrit should be 44% or less to use a flush rate of 30 ml/min and keep the blood product exiting the filter within the desired amount of hemolysis of 50 mg/dl.

$$HCT = \ln(0.131 * PLH)/0.0428 \quad (1)$$

$$HCT = \ln(0.131 * 50)/0.0428 \quad (2)$$

$$HCT = 44\% \quad (3)$$

Figure 15F:
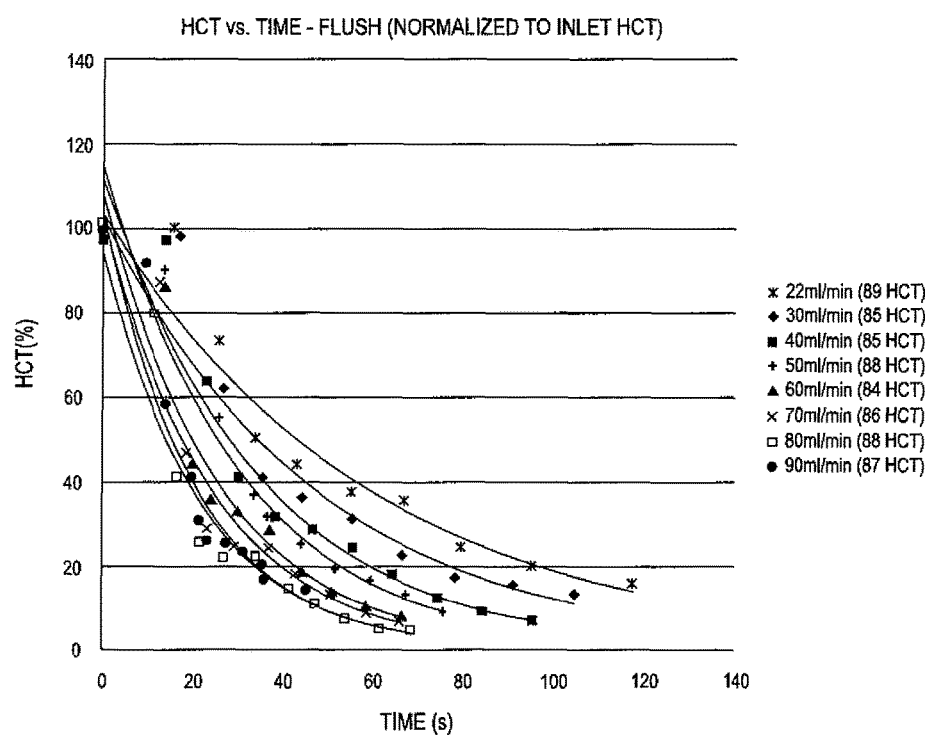
FIG. 15F is a graphical representation of the normalized hematocrit vs. flush time of the various tests of the Example.

Next, the normalized hematocrit (HCT) vs. flush time for each test was plotted, as shown in the Graph entitled HCT vs. Time-Flush (Normalized to Inlet HCT) of FIG. 15F. The data of each test was then fitted to a best fit curve, the equations of which for each flush rate are listed below in Table 10. The equations below can be used to determine the time required to decrease the hematocrit of the red blood cells in the filter for each flush rate.

TABLE 10

| Flush Rate (ml/min) | Time vs. HCT |
|---|---|
| 22 | Time = ln(.0096*HCT)/−0.017 |
| 30 | Time = ln(.0097*HCT)/−0.021 |
| 40 | Time = ln(.0089*HCT)/−0.029 |
| 50 | Time = ln(.0086*HCT)/−0.033 |
| 60 | Time = ln(.0092*HCT)/−0.040 |
| 70 | Time = ln(.0097*HCT)/−0.042 |
| 80 | Time = ln(.0105*HCT)/−0.046 |
| 90 | Time = ln(.0110*HCT)/−0.048 |

For example, when the flush rate is 30 ml/min, it will take about 11 seconds for the red blood cells within the filter to decrease from a hematocrit of 50% to a hematocrit of 40%.

$$Time_d = (\ln(0.0097 * HCT_1)/-0.021) - (\ln(0.0097 * HCT_2)/-0.021) \quad (1)$$

$$Time_d = (\ln(0.0097 * 50)/-0.021) - (\ln(0.0097 * 40)/-0.021) \quad (2)$$

$$Time_d = 11 \text{ sec} \quad (3)$$

Figure 15G:
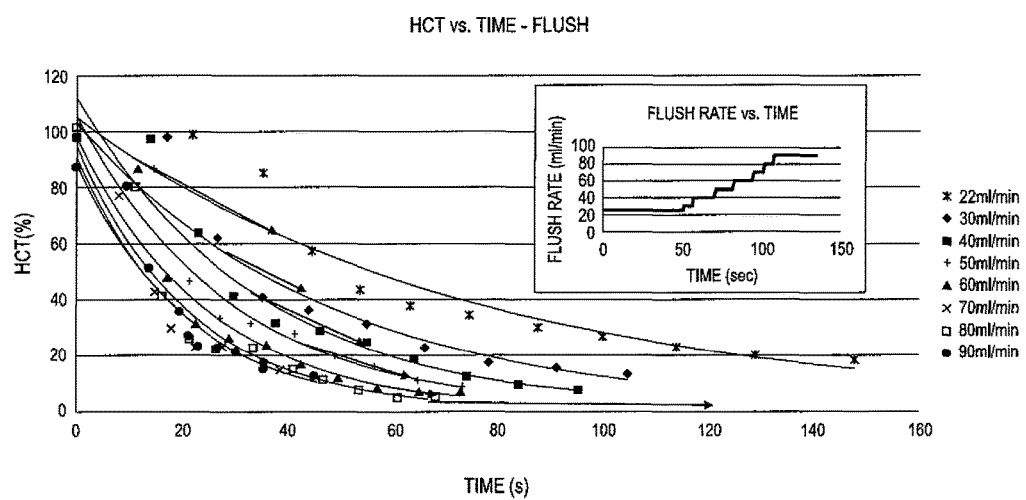
FIG. 15G is a graphical representation of flow rate increases based on the first and second correlations of the Example.

Wherein:
$HCT_1$ is the initial hematocrit
$HCT_2$ is the second lower hematocrit
$Time_d$ is the time it takes to decrease from $HCT_1$ to $HCT_2$ As described in more detail below and graphically shown in FIG. 15G, the above correlations may be combined to determine the increases in additive solution flush rate during filter flushing.

Figure 15H:
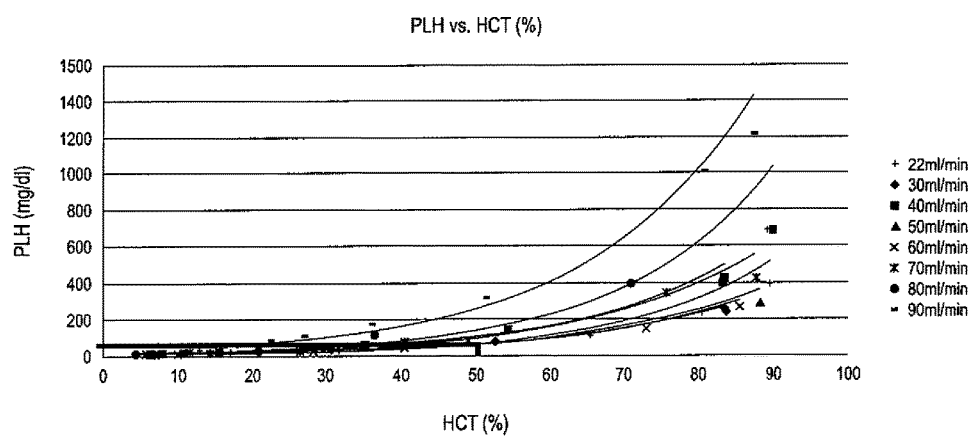
FIG. 15H is a graphical representation illustrating the determination of which flow rate to use when the hematocrit reaches or decays to 50%.

FIGS. 15H-15K graphically illustrate one example of how the correlations may be combined to produce an increasing flush rate during flushing. In this example the selected hemolysis is below about 50 mg/dl. Turning first to FIG. 15H, the graph shown therein is similar to that of FIG. 15E except that lines have been added to indicate the intersection of 50 mg/dl and 50% hematocrit. When filter flushing begins, the filter has a high hematocrit between, for example, 70% and 88%. As indicated by the graph, the filter should be flushed with additive solution at 22 ml/min until the red blood cells within the filter have a hematocrit that is below 50%. If the flush rate is increased to higher than 22 ml/min with a greater than 50% hematocrit, according to this graph, hemolysis would undesirably increase and be much greater than 50 mg/dl.

Figure 15I:
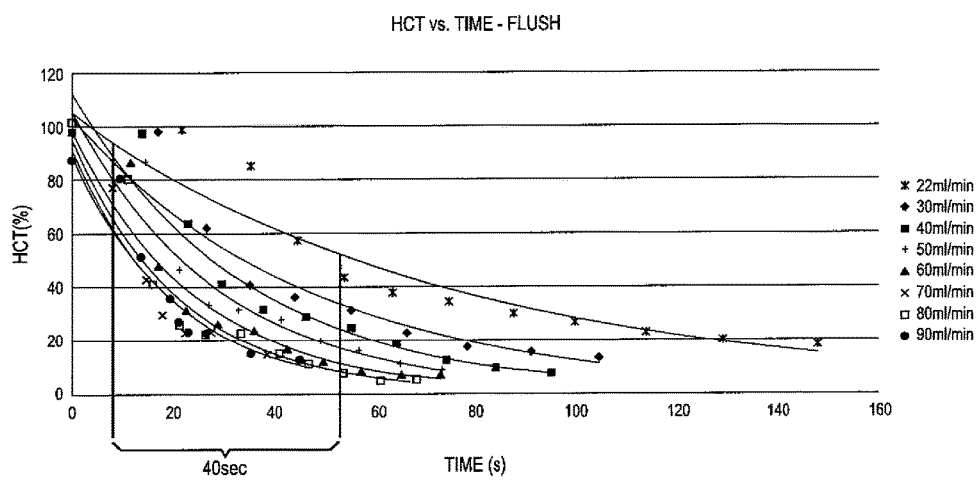
FIG. 15I is a graphical representation illustrating the determination of the time it takes for the hematocrit to decay from 88% to 50% at a flush rate of 22 ml/min.

Turning now to FIG. 15I, at a flush rate of 22 ml/min the graph indicates that it will take about 40 seconds for the hematocrit of the red blood cells within the filter to decrease from 88% to 50%. Accordingly, the initial flush rate of the additive solution in this example would be 22 ml/min for 40 seconds. After 40 seconds has passed, the additive solution flush rate is increased to 30 ml/min.

Figure 15J:
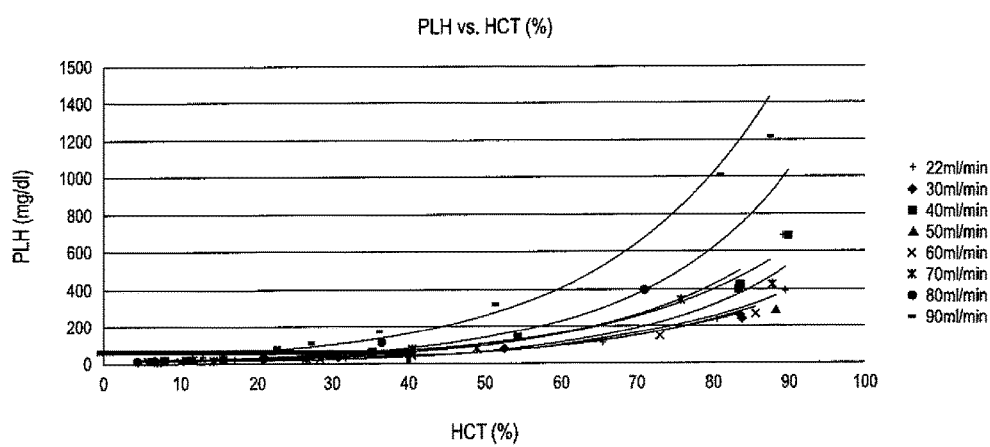
FIG. 15J is a graphical representation illustrating the determination of which flow rate to use when the hematocrit reaches or decays to 40%.
Figure 15K:
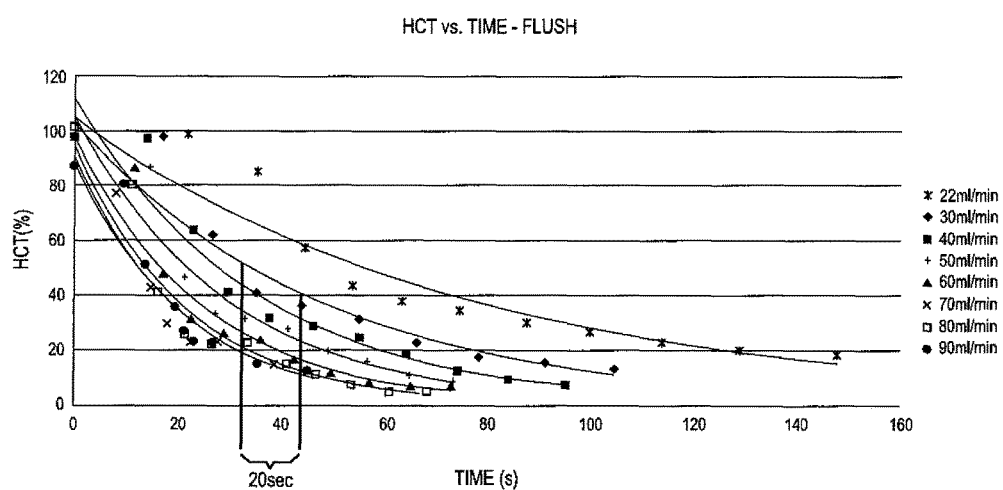
FIG. 15K is a graphical representation illustrating the determination of the time it takes for the hematocrit to decay from 50% to 40% at a flush rate of 30 ml/min.

FIG. 15J is similar to FIG. 15H except that it includes lines showing the intersection of 50 mg/dl and 40% hematocrit. As indicated by this graph, to keep the hemolysis at or below 50 mg/dl, the additive solution flush rate should remain at 30 ml/min until the hematocrit of the red blood cells within the filter is at 40%. As graphically shown in FIG. 15K, at an additive solution flush rate of 30 ml/min, it will take about 12 seconds for the hematocrit of the red blood cells to decrease from 50% to 40%. Therefore, the flush rate will remain at 30 ml/min for 12 seconds. After 12 seconds have passed, the additive solution flush rate is increased to 40 ml/min until the hematocrit of the red blood cells within the filter is below 30%.

The above process is repeated to determine the rest of this increasing step pattern until the flush rate reaches 90 ml/min and the flush rate remains at 90 ml/min until the flush is complete. The same or similar process for determining the ramping up of flush rates illustrated in this example may be used to determine flush rates of different filters, additive solutions and/or blood products. Additionally, the variables (i.e. hemolysis, hematocrit and flow rates) also may be varied, depending on the application and desired outcome.

IV. Data Management Systems and Methods

The system described herein can also incorporate data management solutions. Weight scales and the addition label printing devices to the system would allow users to obtain product weight labels directly from the separation system at the completion of the procedure. This eliminates manual weighing and recording of data used in current processing methods. The module B may include a suitable user interface, such as a touch screen, keypad or keyboard, as well as a scanner, to allow users to input information such as user donor identification number, blood bank identification, fluid circuit kit numbers, lot numbers, etc., which could also improve data management efficiency in blood manufacturing centers.

Figure 29:
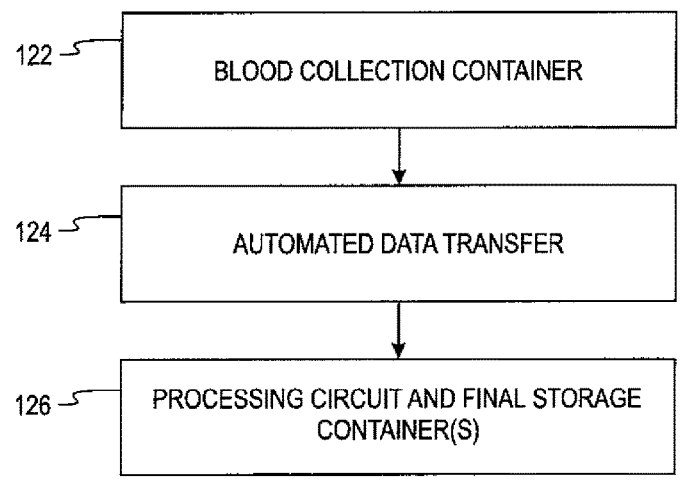
FIG. 29 is a flow chart illustrating a data management method in accordance the present disclosure.

More specifically, and in accordance with another aspect of the present disclosure, a method is provided for automating the transfer of data associated with the whole blood collection container, as well as other pertinent information, to the processing circuit used for the subsequent separation of the whole blood and the final storage container or containers for such separated blood component or components. This method is illustrated schematically in the flow chart of FIG. 29, where a source container is provided (step 122), which typically contains a unit of previously-collected whole blood, although the source container may contain a previously-processed blood product. The source container typically has data associated with it relating to the identification of the donor and the collection time, place, etc., such data preferably being in a machine-readable format, such as a bar code or a RFID tag. This data is then retrieved and transferred (step 124), and then associated with the processing circuit and final storage containers (step 126).

Figure 30:
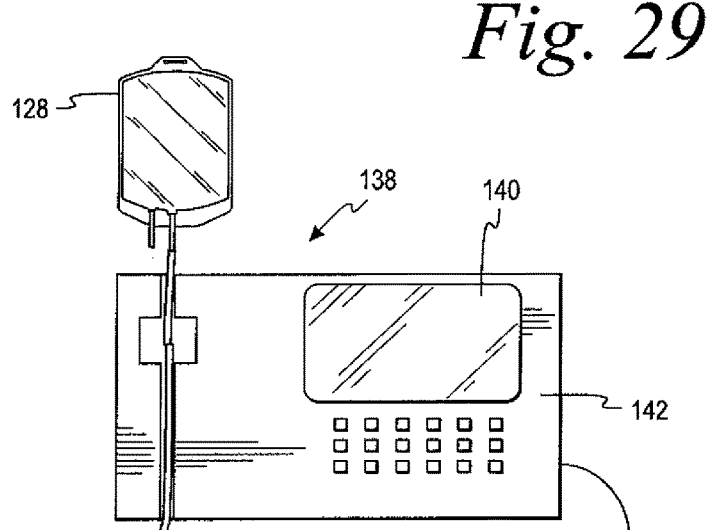
FIG. 30 is a schematic drawing of a data management system according to the present disclosure in combination with a collection container and a processing kit.
Figure 30:
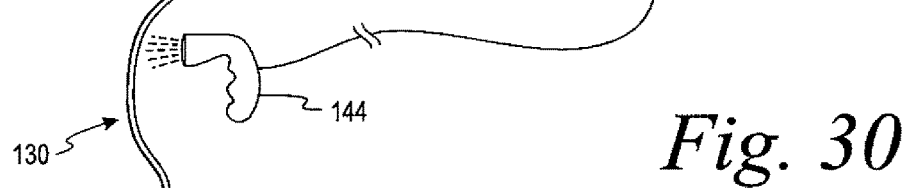
Figure 30:
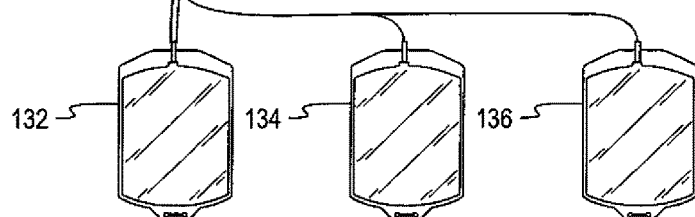

Turning to FIG. 30, one possible system for the use of a data management system in accordance with the present disclosure is shown. A blood collection container 128 and a separate processing circuit 130 having three final storage containers 132, 134 and 136, are provided. During the collection of the whole blood, donor identification information is encoded and associated with the container for the collected whole blood. This may be done by manually placing a bar code label for the donor id onto the container label, container pin, or tubing. It may also be done by utilizing an RFID writer at the point of collection, transferring the donor ID from a collection scale or hand-held device onto an RFID tag attached to the collection container. The use of RFID permits a greater amount of information to be managed, including such data as container-type, expiration date, collection time, collection volume, nurse identification, collection site, and the like.

The automated data transfer between the collection container 128 and the processing kit 130/storage containers 132, 134, 136 may occur in the context of the sterile connection of the collection container 128 to the processing kit 130. For example, an electromechanical system that accomplishes the sterile connection of the whole blood collection container to the processing kit may be used. Such a system is disclosed in U.S. Provisional Patent Application Ser. Nos. 61/578,690 and 61/585,467 filed on Dec. 21, 2011 and Jan. 11, 2012, respectively, which are incorporated herein by reference. The sterile connect device may be free standing, as shown in the above referenced provisional applications, or integrated with the reusable module B described above. Alternatively, the data management system may be simply associated with the reusable module B, without a sterile connect device associated therewith. In any event, the sterile connection device or reusable module includes a programmable controller configured to automatically perform, or prompt the user to perform, the various steps of the data management method, as described in greater detail below.

Figure 31:
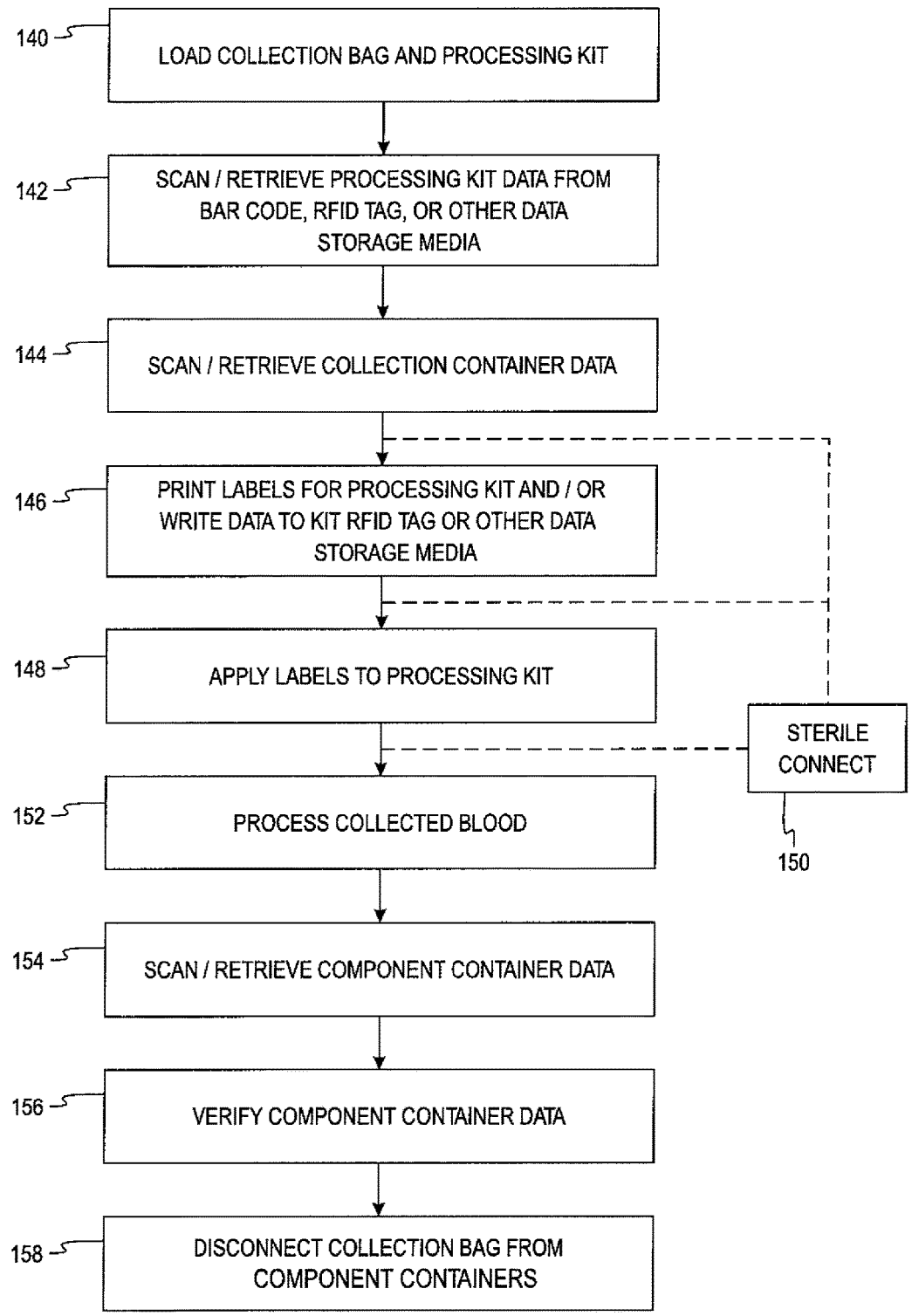
FIG. 31 is a flow chart illustrating the various steps comprising a method for data management in accordance with the present disclosure.

The data management system 138 incorporates a processing unit, a screen 140 for providing information to the user (such as prompts and confirmations), a touch pad 142 to permit the user to input information, and a scanner/reader 144 for retrieving and transferring information between the collection container 128 and the processing kit 130. The system 138 also provides for the printing of bar code labels or transfer of data to one or more RFID tags associated with the processing kit. Turning now to FIG. 31, a flow chart generally illustrating the data management method is shown. The method includes loading the collection bag and processing kit onto the reusable module and/or sterile connect device (step 140). The data associated with the processing kit and the data associated with the collection container is retrieved (steps 142 and 144). As can be appreciated, the order in which these steps are performed is not critical. As noted above, this data may take the form of a bar code, an RFID tag or other form, the processing kit and its associated collection containers have the pertinent data from the collection container associated therewith. This may either take the form of printing bar code labels or writing data to an RFID tag (steps 146 and 148). The collection container and processing kit are connected, preferably in a sterile connect procedure (step 150), such connection occurring at a time during the sequence of the performance of the above-described steps.

The blood in the collection container is then processed (step 152). The processing kit/storage container information is then retrieved and verified against the collection container data (steps 154 and 156). After such verification, the storage containers may be disconnected from the collection container (step 158).

The system of the present disclosure assists the user in performing the steps described above in that it provides prompts and confirmations for the various steps. For example, if the identifying information is in the form of a bar code, the system prompts the user to scan the bar code ID of the processing kit and the donor ID of the collection container. The system will then print replicate bar code labels on a printer that is either integral to the system or attached to it, with the type and quantity of the labels being determined by the type of processing kit loaded. The system then prompts the user to apply the bar code labels to the final storage containers. After the system processes the blood into its components, the system prompts the user to scan the final component container bar code IDs so that the system may verify correct bar code information prior to detaching the storage containers from the collection container and processing kit.

If the identifying information is associated with an RFID tag, the system automatically scans the RFID tag on the collection container and then automatically reads the information on the RFID included on the processing kit. The system then automatically replicates the collection container information to the RFID tag or tags associated with the processing kit storage containers. After the system processes the blood into the components, according to the type of processing kit detected by the instrument, the system will read the RFID tag on the final component containers to permit verification of the identifying information prior to detaching the blood storage containers from the processing kit and collection container.

It is contemplated that the system may employ both bar code and RFID as redundant systems, and include some or all of the steps described above, as applicable. While the bar code scanner/RFID reader is described as being associated with the reusable module B, it could be a dedicated station physically separate from the processing machine itself, though linked through the data management software.

While this data management method has been described in connection with the collection of the whole blood in a container separate from the processing kit and storage containers, it may equally well be used in connection with a system or kit in which the collection container is integral with the processing kit and its storage containers. Further, the method may be used in connection with the processing of whole blood drawn directly from a donor, as described below, with the donor identification data being provided by the donor, and not a collection container, or in a cell washing procedure, with the identification data being associated with the source container.

V. Systems and Methods for Processing Whole Blood from a Donor

In accordance with another aspect of the present disclosure, the spinning membrane separator described above may be advantageously used in the single step or "chairside" collection and separation of whole blood into blood components. As described below, an automated whole blood collection system is provided that separates whole blood into a single unit of red blood cells and plasma simultaneously with the collection of whole blood from a donor. The system is intended to be a single pass collection system, without reinfusion back to the donor of blood components. The system preferably comprises a disposable fluid flow circuit and a durable reusable controller that interfaces with the circuit and controls fluid flow therethrough. The flow circuit is preferably a single use pre-sterilized disposable fluid flow circuit that preferably comprises red blood cell and plasma collection containers, anti-coagulant and red cell additive solutions, a separator and a fistula for providing a passageway for whole blood from the donor into the fluid circuit. The durable controller preferably comprises a microprocessor-controlled, electromechanical device with valving, pumping, and sensing mechanisms configured to control flow through the circuit, as well as safety systems and alarm functions, appropriate for a whole blood collection procedure.

The method of blood collection utilizing the system comprises performing a venipuncture on a donor and the withdrawing whole blood from the donor into the disposable circuit where it is manipulated by the instrument and the components of the fluid circuit to result in the whole blood being separated into the desired red blood cell and plasma components. The donor remains connected to the system throughout the procedure, and all fluids remain in the fluid path of the single-use kit until the procedure is completed. As a "single pass" system, whole blood preferably passes through the flow circuit one time only, and no blood component is returned to the donor. In a further alternative, the collection procedure is performed in two steps to permit the collection of an increased volume of red blood cells from the donor. In a first step, whole blood is withdrawn from a donor from which a first quantity of red blood cells and a first quantity of plasma are separated. At the end of the first step, the first quantity of separated plasma is returned to the donor, after which collection and separation of whole blood is resumed and a second quantity of red blood cells and a second quantity of plasma are collected. The second quantity of separated plasma is then returned to the donor.

The red blood cells resulting from the collection may not necessarily be process leukoreduced. However, leukoreduction by filtration may be achieved with a leukoreduction filter preferably integrated to the single use circuit or by the use of a separate processing circuit that is sterile-connected to the red blood cell collection container.

The instrument preferably includes an operator interface for inputting information and/or displaying information such as a touch screen, keypad, mouse, keyboard, etc. A message display allows the operator to control the procedure, gather information on its status, and address any error conditions as they may arise.

Turning to the drawings, there is seen in FIGS. 16-19 a schematic representation of a whole blood automated collection system, generally designated 210, in accordance with the present disclosure, in different stages or phases of operation. The system preferably includes a reusable hardware component 212 that preferably comprises pumps, clamps and pressure sensors to control fluid flow, and a single-use pre-assembled sterile disposable fluid circuit component 214 that may be mountable to the hardware component and includes various containers/pouches, a donor access device or fistula, and a blood separation chamber, all interconnected by a sterile fluid pathway, such as flexible plastic tubing. The containers/pouches are typically collapsible, and made of a suitable plastic material, as is well known in the art. The material of the containers may differ depending on usage, and may include plasticizer-free materials such as DEHP-free polymers, particularly, but not exclusively, for red cell storage.

More specifically, the illustrated fluid circuit component or module 214 comprises a donor access device 216 that includes a first length of tubing 218 as the draw line through which whole blood is withdrawn from a donor and introduced into the fluid circuit 214. The donor access device 216 preferably comprises a needle, and particularly a small gauge needle (18-21 gauge) for enhanced donor comfort with a needle guard if desired for prevention of inadvertent needle sticks. The tubing 218 communicates with a blood separation device, generally designated 220 and, as described above, to introduce whole blood into the separator.

A second length of tubing 222 provides for fluid communication between the separator 220 and a first container/pouch 224 for receipt of the separated concentrated red blood cells, while a third length of tubing 226 provides for fluid communication between the separator 220 and a second container/pouch 228 for the receipt of plasma.

The fluid circuit 214 also comprises a source of anticoagulant (e.g., CPD), which is contained in a third container 230 that communicates with the first length of tubing 218 by means of a fourth length of tubing 232 that is joined to tubing 218 by, e.g., a Y-connector. The fluid circuit 214 may also include a source of preservative solution for the red blood cells that are to be delivered to the container/pouch 224. The preservative solution may be contained in a separate pouch that is communication with the container 224.

Alternatively, the container 224 may be pre-filled with an amount of preservative solution adequate for the amount of red blood cells to be received therein during the collection procedure.

The fluid circuit 214 also includes an integral sampling system 234 for the aseptic collection of blood samples prior to and during the donation process. The sampling system 234 comprises a pouch that communicates with the first length of tubing 218 of the donor access device through a fifth length of tubing 236 upstream of the connection between tubing 218 and tubing 232, through which the anticoagulant is introduced. Tubing 236 preferably communicates with tubing 218 through a Y-connector or similar device.

Figure 16:
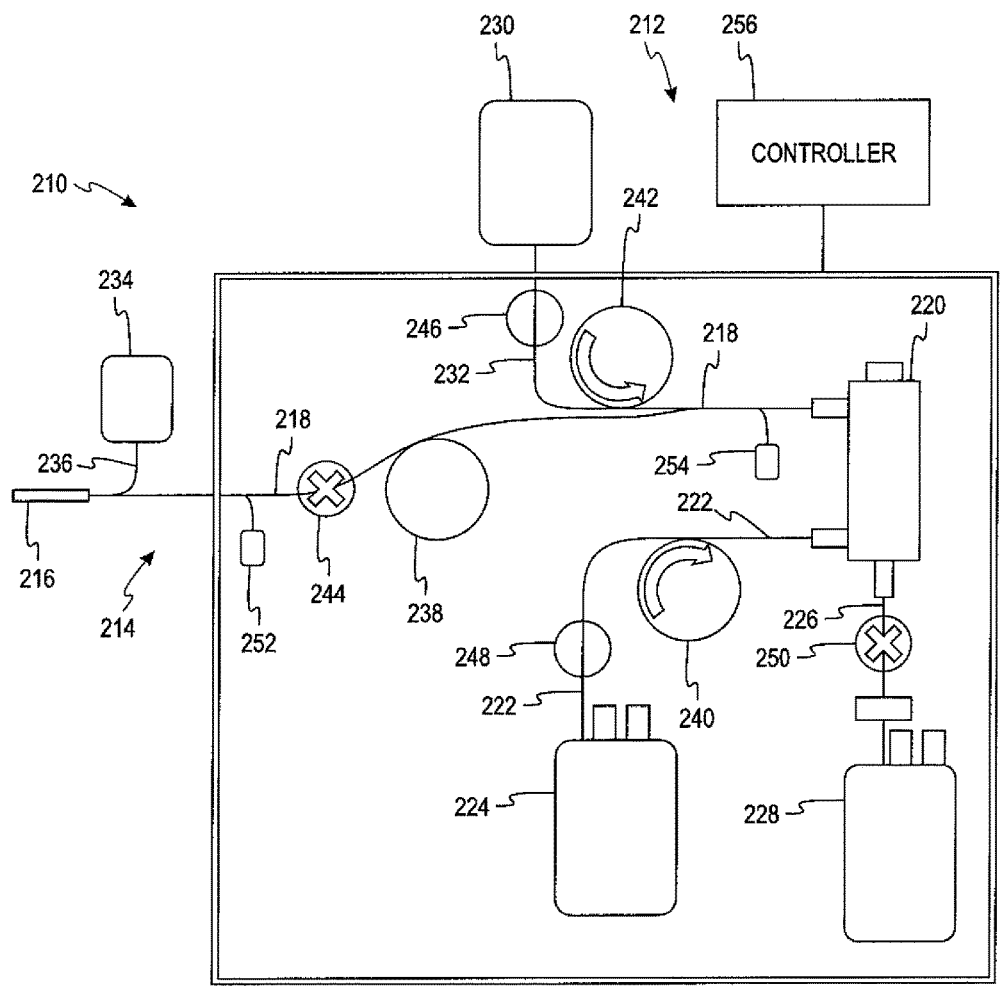
FIG. 16 is a schematic view of an automated whole blood collection system according to the present disclosure showing the configuration of the system for automated chairside collection and processing of whole blood from a donor in the priming mode.
Figure 16A:
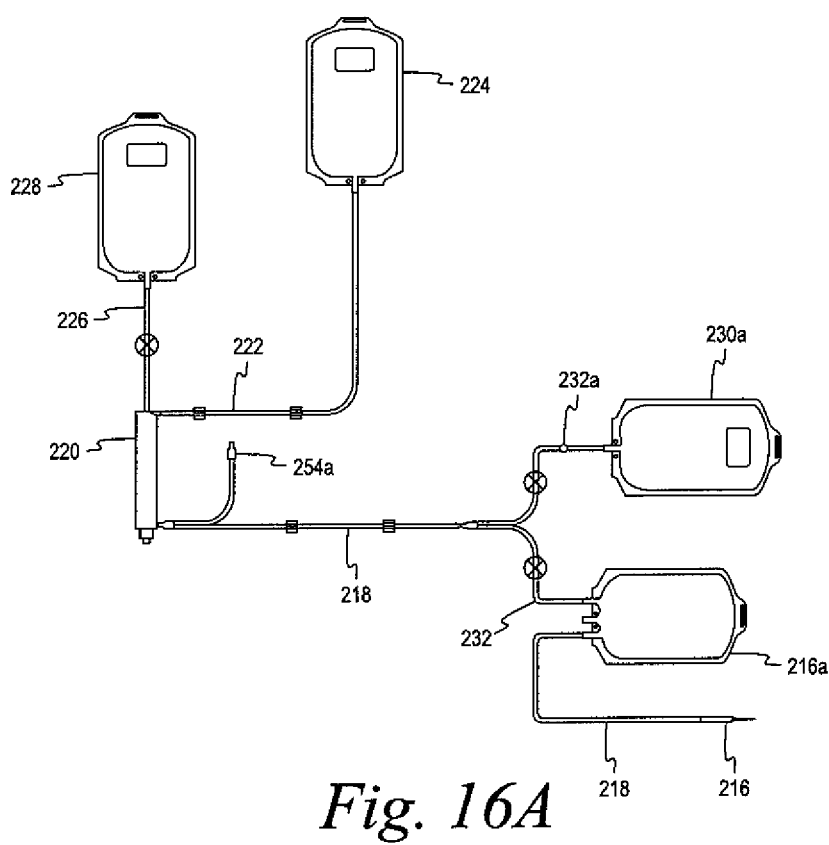
FIGS. 16A-16D show various alternative disposable fluid circuits in accordance with the present disclosure.
Figure 16B:
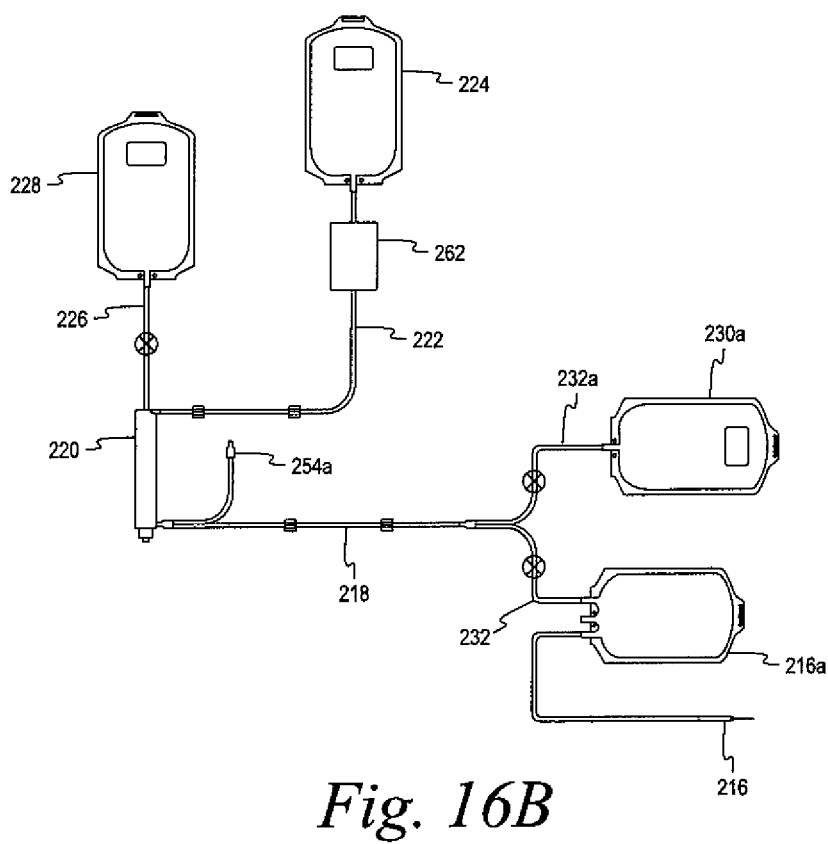
Figure 16C:
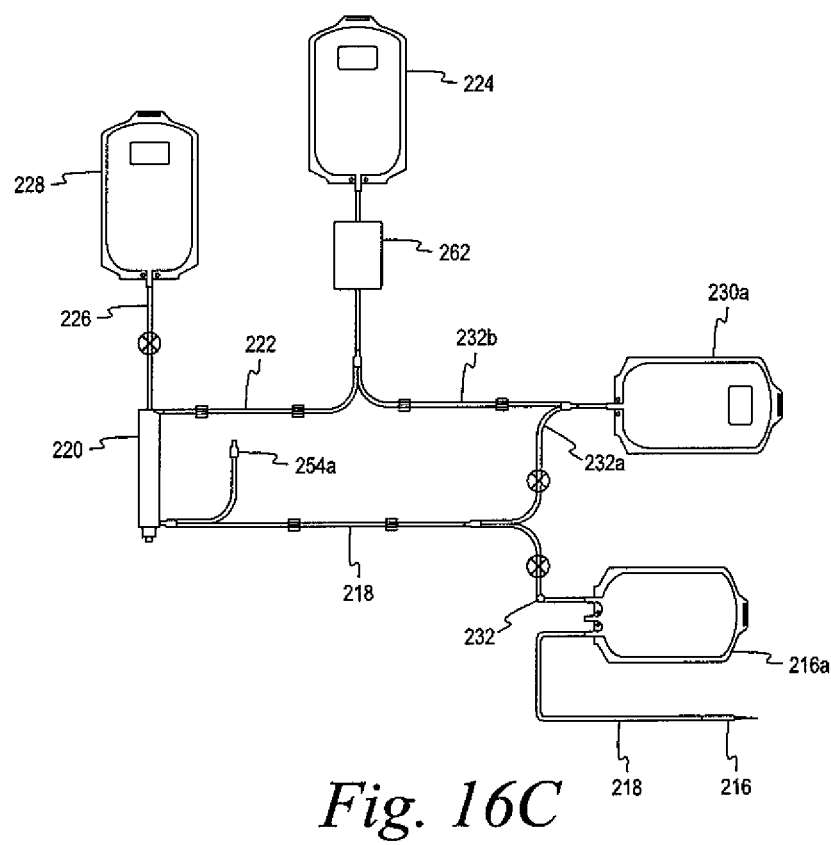
Figure 16D:
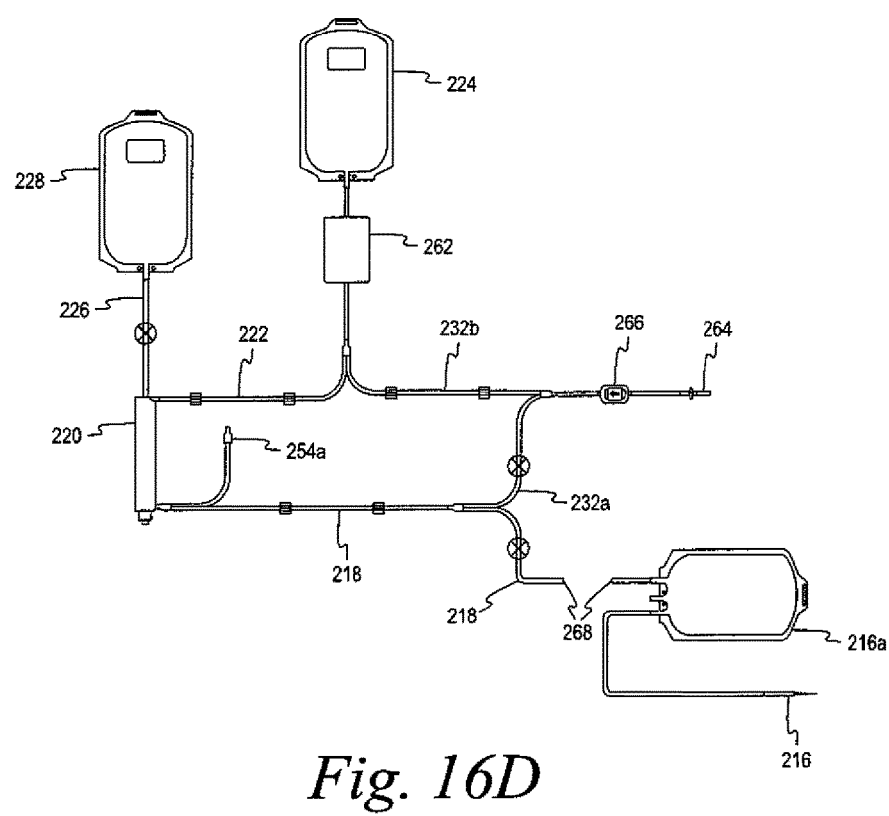

Alternative disposable fluid circuits that may be used during an automated whole blood separation procedure are seen in FIGS. 16A-16D. Each contains a core set of components which includes an inverted spinning membrane separation device 220 (with the inlet located proximate to the bottom of the separator and the outlets located proximate to the top), a plasma product container or bag 228, a red blood cell product container or bag 224, a whole blood collection container or bag 216a connected to a donor access device 216 (such as a needle), a red cell additive solution container or bag 230a, a pressure transducer connector 254a, and a plurality of pump tubing keepers. The whole blood collection bag 216a and additive solution bag 230a may be pre-attached to the kit during manufacturing (as seen in FIGS. 16A-16C), or may be separate from the rest of the core components and attached to the remainder of the fluid circuit at the time of the processing (as seen in FIG. 16D). (It is understood that any required anticoagulant has been added to whole blood in the collection bag at or about the time it is withdrawn from the donor. Otherwise, the fluid circuits of FIGS. 16A-16D may also incorporate a source of anticoagulant solution.) Additional components such as a leukofilter 236 (FIGS. 15B-15D), an additive solution spike 264 (FIG. 16D), an additive solution filter 266 (FIG. 16D), and sterile dock connectors 268 (FIG. 16D) can be added to the core components.

FIGS. 16A and 16B depict fluid circuits compatible with the 2-pump configuration of the automated separation device, such as that illustrated in FIGS. 9 and 11-13, described above. FIGS. 16C and 16D depict fluid circuits compatible with the 3-pump configuration of the automated separation device, with the fluid circuit of FIG. 16C having the whole blood collection bag 216a and the additive solution bag 230a integrally attached, while whole blood collection bag 216a and the additive solution bag 230a for the fluid circuit of FIG. 16D are separate from the remainder of the fluid circuit and attached at the time of processing.

More specifically, the fluid circuit of FIG. 16A is used in a 2-pump durable device configuration to produce a plasma product and a non-leukoreduced red blood cell product. The red cell additive solution bag 230a and whole blood collection bag 216a are pre-attached to the fluid circuit. The fluid circuit of FIG. 16B is also used in a 2-pump device configuration to produce a plasma product and a leukoreduced red blood cell product. As such, this fluid circuit contains a leukofilter 262 integrated into the tubing 222 through which the separated red blood cells flow. This allows the red blood cells to be leukoreduced immediately upon exiting the spinner. The red cell additive solution bag 230a and the whole blood collection bag 216a are pre-attached.

The fluid circuit of FIG. 16C is used in a 3-pump durable device configuration to produce a plasma product and a leukoreduced red blood cell product. A second solution dilution line 232b connects the additive solution bag 230a to tubing 222 for the separated red blood cells. The line 232a is passed through a pump (such as pump 240) to continuously pump additive solution into the separated red blood cells after exiting the spinning membrane 220 and prior to entering the filter 262 to dilute the concentrated red blood cells. This decreases the hematocrit of the blood passing through the filter, thus improving red blood cell product quality. As with the embodiments of FIGS. 16A and 16B, the red cell additive solution bag 230a and the whole blood collection bag 216a are pre-attached to the fluid circuit.

The fluid circuit of FIG. 16D is also configured to be used with a 3-pump durable device configuration kit and includes means such as spike 264 and sterile docks 268 for attaching the additive solution bag 230a and whole blood collection bag 216a to the circuit at the time of processing. In this case, the fluid circuit must also include a sterile filter 266 through which the additive solution is passed to ensure sterility. The sterile-connection may be made with current common sterile connection devices (such as the Terumo® Sterile Tubing Welder) or with the sterile dock device 120 described above.

The means for attaching the various fluid containers at the point of processing can be incorporated in any combination into the fluid circuits of FIGS. 16A-16C. For example, the fluid circuit of FIG. 16A can have both the additive solution bag 230a and the whole blood bag 216a pre-attached (as shown), can have only the whole blood bag 216a pre-attached and the additive solution spike 264 for later attachment of the additive solution bag 230a, can have only the additive solution bag 230a pre-attached and the sterile dock sites 268 for connecting the whole blood collection bag 216a, or can have neither the additive solution bag 230a nor the whole blood collection bag 216a pre-attached (as shown in FIG. 16D).

Fluid circuits to which the whole blood collection bag 216a is pre-attached are intended to be used at the point of collection. In contrast, fluid circuits that include a sterile dock site for attaching the whole blood collection bag 216a will not travel to the point of collection, and only the separate whole blood collection bag 216a will be present at the point of collection. This may be beneficial to the user, decreasing the amount of supplies that must travel to mobile collection sites, as the fluid circuits that include a sterile dock site for attaching the whole blood collection bag 216a do not need to travel to the point of collection.

The durable hardware component 212 preferably comprises a first pump 238 that cooperates with tubing 218 for pumping whole blood to the separation device 220 and a second pump 240 that cooperates with the tubing 222 for transporting substantially concentrated red blood cells from the separation chamber 220 to the first collection container 224. The pumps 238, 240 are preferably peristaltic or roller pumps that include a rotor with one or more rollers for compressing the tubing to force the fluid to be moved therethrough, although other suitable pump designs, such as flexible diaphragm pumps, may also be used. The hardware component also preferably includes a third pump 242 that cooperates with tubing 232 for transporting anticoagulant to the draw line tubing 218 through which whole blood is transported to the separator 220. The third pump 242 provides for metering the flow of anticoagulant, and also facilitates the priming and rinsing of the system, as will be described below. However, the third pump 242 is optional, and anticoagulant may be metered to the whole blood draw line 218 by gravity flow, with the tubing 232 being dimensioned to provide a suitable flow rate over the duration of the collection procedure.

The hardware component 212 also preferably comprises clamps 244, 246, 248 and 250 for selectively occluding and opening the tubing segments 218, 232, 222, and 226, respectively. The term "clamps" is used broadly herein, and includes any mechanism that cooperates with the flow paths, e.g., tubing segments, of the fluid circuit to selectively permit or preclude fluid flow therethrough. The hardware component 212 also preferably comprises pressure sensors 252, 254 in the draw line tubing 218 proximate or adjacent the needle (pressure sensor 252) and proximate or adjacent the inlet to the separator 220 (pressure sensor 254) to monitor the inlet pressure, such as to detect a vein collapse. A weigh scale (not shown) is also preferably provided for at least the first container 224 to provide feedback on the red blood cell volume collected.

In keeping with another aspect of the disclosure, the reusable hardware component preferably comprises a programmable controller 256 for actuating the pumps and clamps and monitoring the pressure sensors and weigh scales so that the whole blood collection procedure may be substantially automated. The controller 256 comprises a programmable microprocessor, and preferably includes an operator interface, such as touch screen and message display to allow the operator to enter and view data and control the procedure, gather information on its status, and address any "error" conditions that may arise.

To perform an automated collection and separation procedure with the automated blood collection system 210 thus far disclosed, the disposable fluid circuit 214 is loaded into operating position on the reusable hardware component 212 as shown in FIG. 16 of the accompanying drawings. In the phase or stage shown in FIG. 16, the system is primed with fluid to substantially remove air and wet the filter membrane. In the primary stage, the first clamp 244 is closed so as to prevent fluid communication between the donor access device 216 and the blood separation chamber 220, and anticoagulant is pumped via pumps 240 and 242 through the tubing 218, separator 212, and tubing 222 to prime the system. A venipuncture is then performed on the donor with the needle of the donor access device to admit whole blood into the tubing 218. At this point, the whole blood may be sampled by means of the sampling pouch 234.

Figure 17:
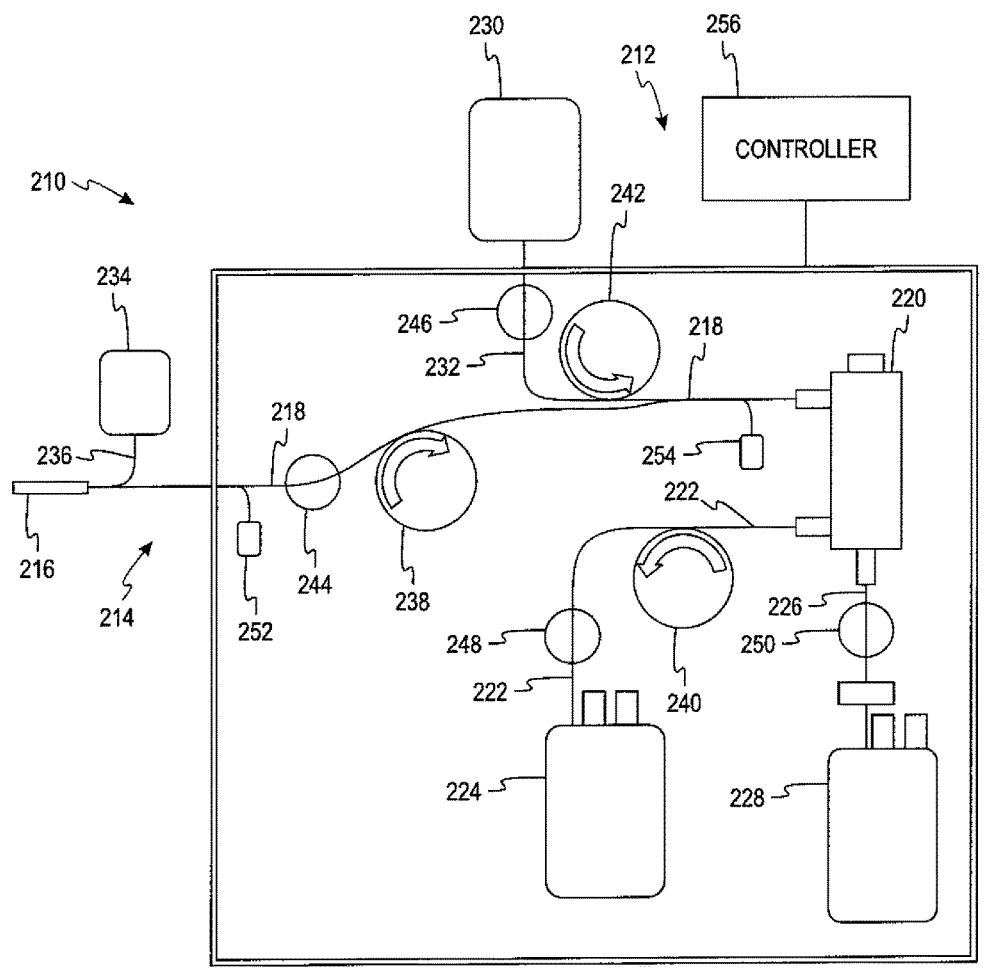
FIG. 17 is a schematic view of the system of FIG. 16 showing the configuration of the system for collecting and separating whole blood into red blood cells and plasma.

Turning to FIG. 17, after priming, the first clamp 244 is opened to flow whole blood through the tubing 218 to the blood separator 220, via pump 238, to commence the collection/separation phase of the collection procedure. The anticoagulant continues to be metered into the draw line tubing segment 218 through tubing segment 232 by means of the third pump 242. Red blood cells exit the separator 220 through tubing 222. The fourth clamp 250 is opened so as to permit plasma to exit the separator 220 and to travel through the tube 226 to the second collection container 228. The first pump 238 presents the whole blood flow to the separator 220, with the inlet pressure being monitored by sensor 254, while the red blood cells are pumped from the separation chamber 220 by the second pump 240. The flow differential between the first pump 238 and the second pump 240 forces the separated plasma to exit the separator 220 into the second collection container 228.

Figure 18:
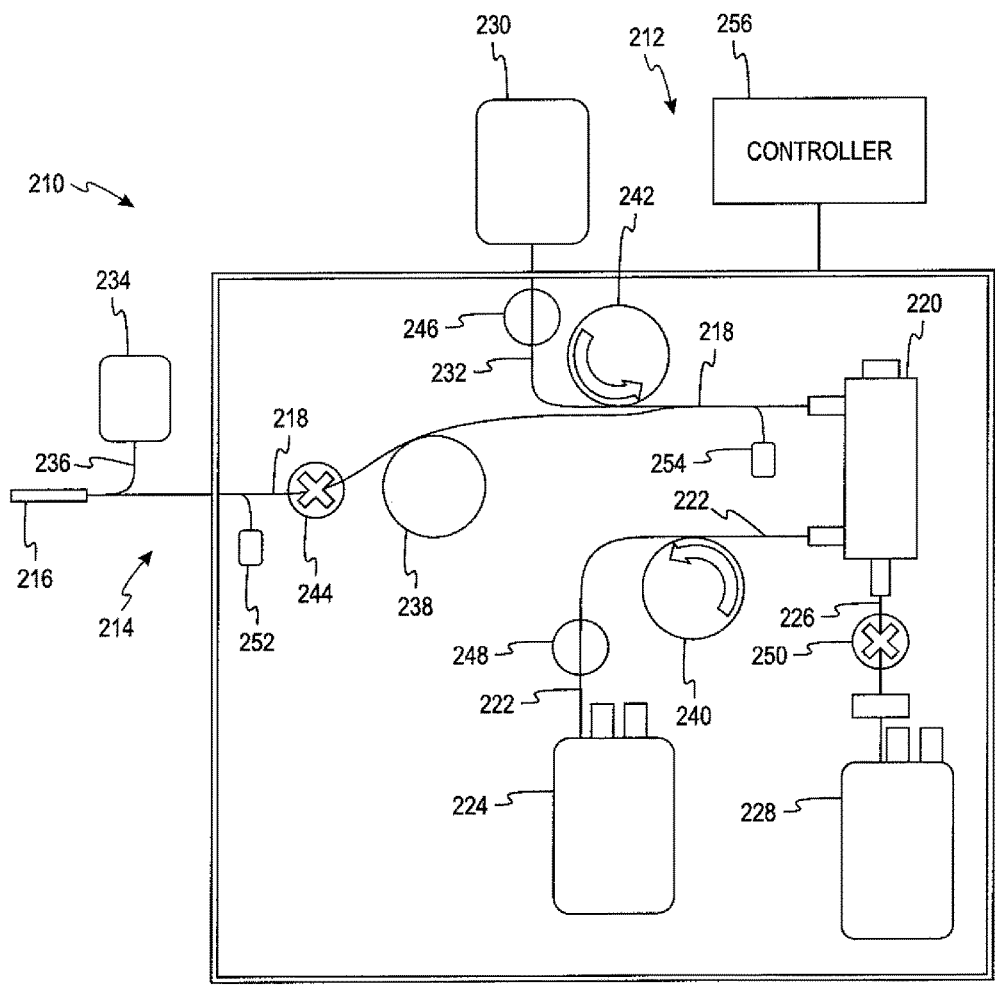
FIG. 18 is a schematic view of the system of FIG. 16 showing the configuration of the system for rinsing the system with anticoagulant after the completion of blood collection from the donor.

With reference to FIG. 18, when the volume of the red blood cells in the first collection container 224 reaches a predetermined volume (as measured by the weight of the first collection container 224 as detected by the weigh scale), the weigh scale will provide the controller 256 with a signal that prompts the controller to terminate the collection procedure by closing the first clamp 244, thus occluding the draw line 218. The donor access device 216 may be withdrawn from the donor at this time. If the system is to be rinsed, the fourth clamp 250 is closed to occlude the flow line 226 to the second collection container 228 for the plasma. The first pump 238 is deactivated while the third pump 242 continues to deliver anticoagulant to the separator 220 with the anticoagulant being exhausted to the first collection container 224 through the tubing segment 222.

Figure 19:
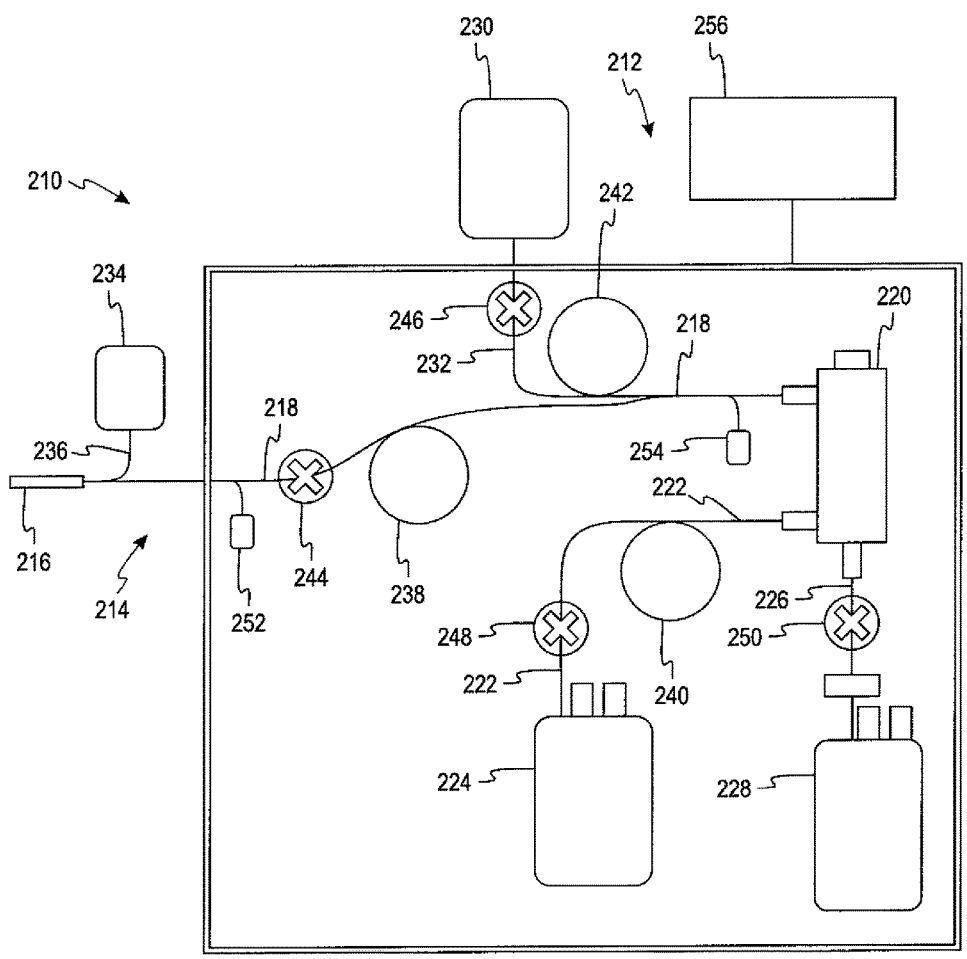
FIG. 19 is a schematic view of the system of FIG. 16 showing the configuration of the system at the end of the blood collection procedure.

Turning to FIG. 19, at the conclusion of the rinse cycle, the second clamp 246 and third clamp 248 are closed, and the second pump 240 and third pump 242 deactivated.

Figure 20:
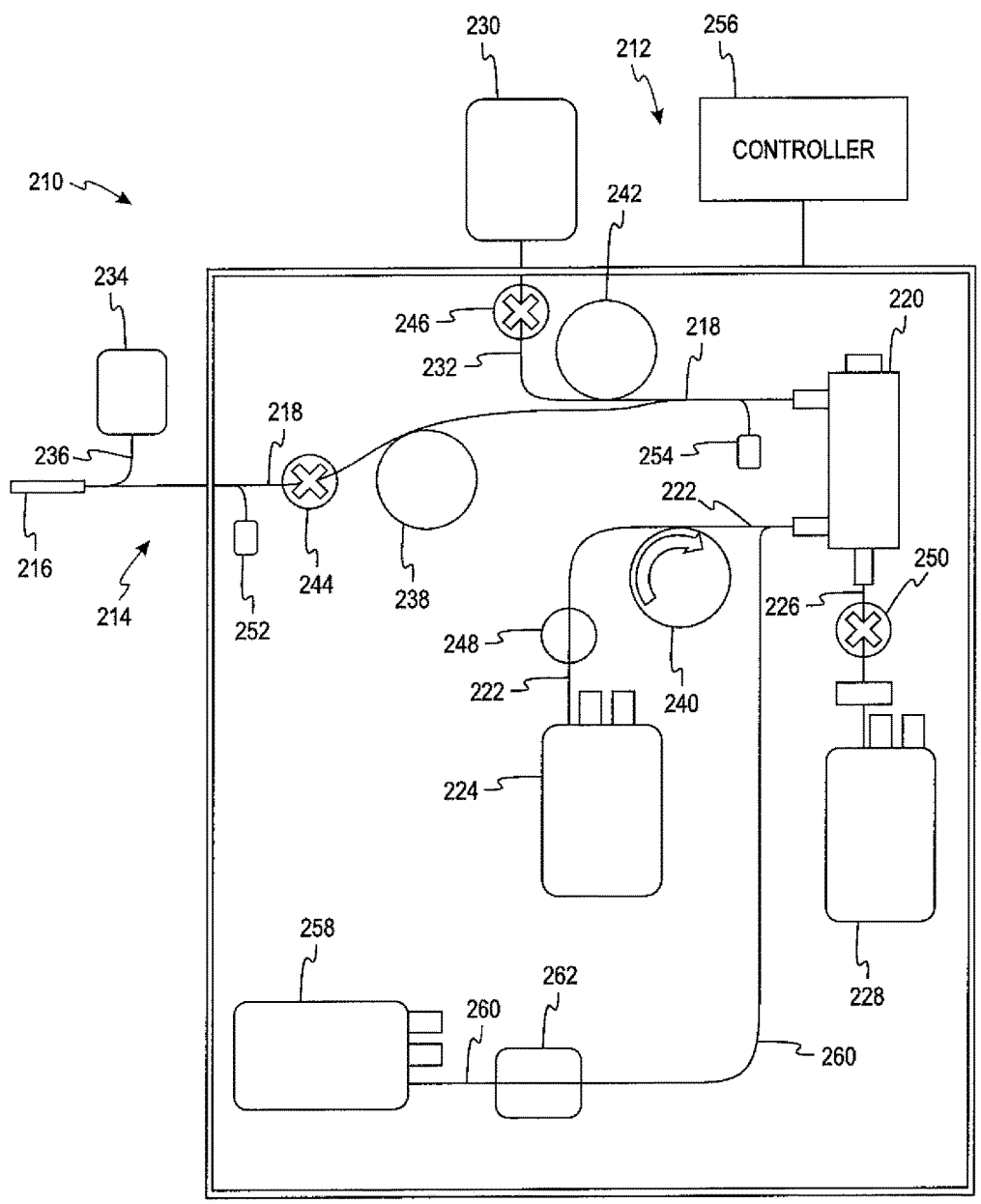
FIG. 20 is a schematic view of the system of FIG. 16 showing the configuration of the system in the optional arrangement for filtering the collected red blood cells through a leukocyte filter.

At this point, the first collection container 224 containing the substantially concentrated red blood cells may be separated from the disposable fluid circuit 214 for storage or to facilitate leukofiltration. This may be done by simply hanging the collection container 224 and allowing gravity filtration of the red blood cells through a leukoreduction filter into a final storage container. However, in accordance with another aspect of the disclosure, and as shown in FIG. 20, a third collection container 258 may be provided that is in fluid communication with the second collection container 224 through a tubing segment 260, with the tubing segment 260 being in fluid communication with tubing segment 222 through a Y connector located on tubing segment 222 between the outlet of the separator 220 and the second pump 240. The third clamp 248 may then be opened to permit the flow of concentrated red blood cells out of the collection container 224, with the second pump 240 activated and pumping in the reverse direction to force the flow of concentrated red blood cells through the leukocyte reduction filter 262 and into the collection container 258. The pressure generated by pump 240 expedites the filtration process significantly as compared to gravity-fed leukofiltration of red cells.

Figure 21:
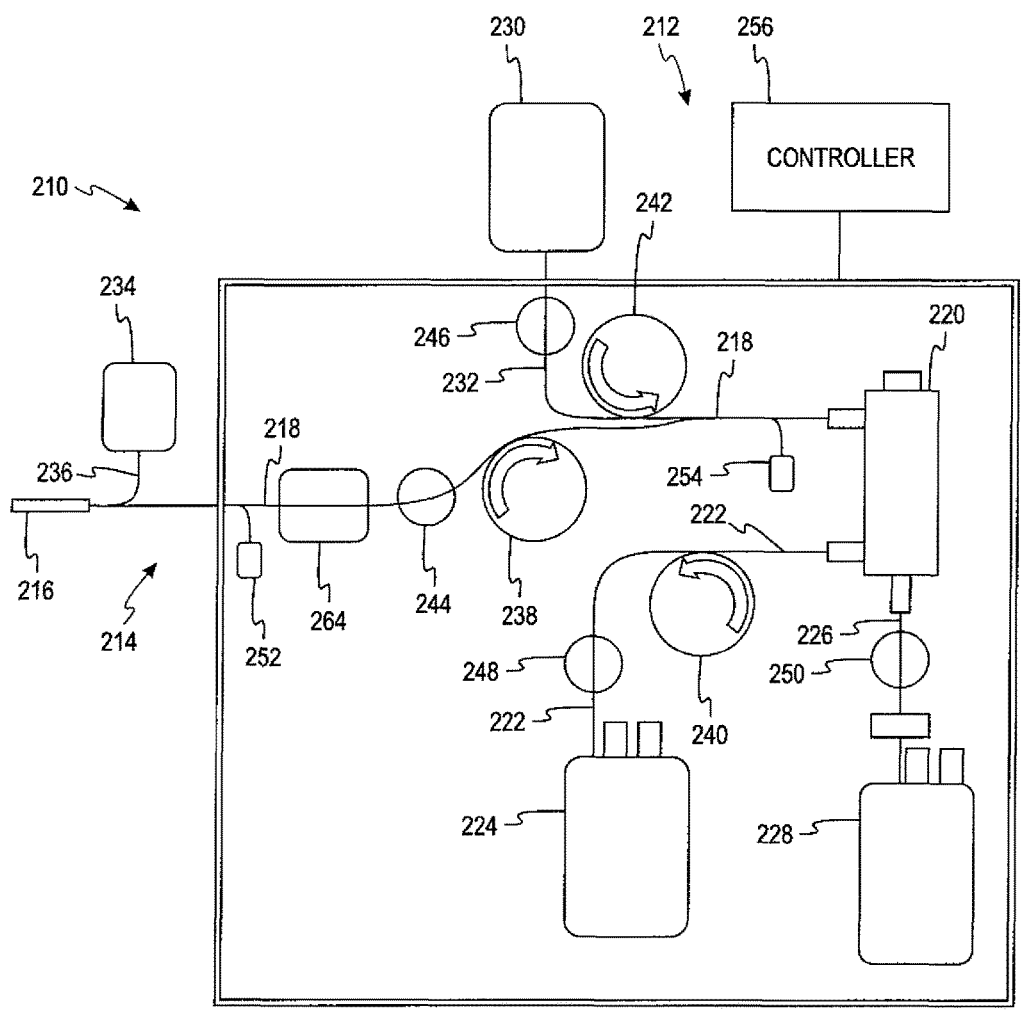
FIG. 21 is a schematic view of an alternate embodiment of an automated whole blood collection system to that of FIGS. 16-20 in which the single-use disposable fluid circuit component comprises an integral leukoreduction filter as part of the draw line of the donor access device.
Figure 21:
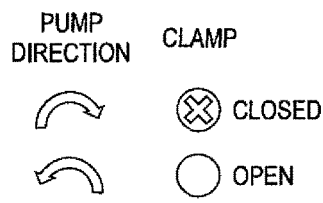
Figure 22:
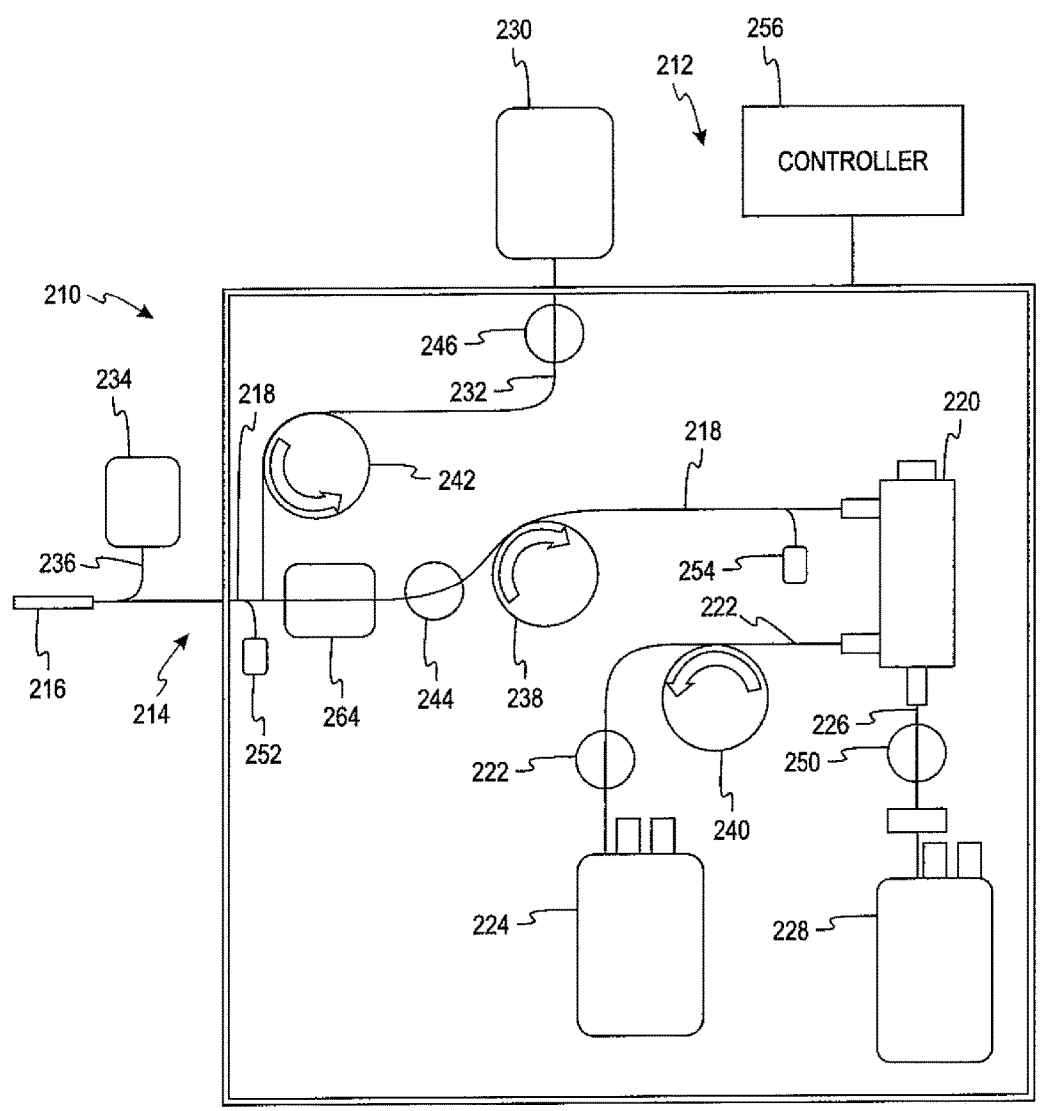
FIG. 22 is a schematic view of an alternative embodiment of the single-use disposable fluid circuit of FIG. 21 in which the leukoreduction filter is positioned in the draw line downstream from the entry point where anticoagulant is introduced into the whole blood.

As a further alternative, leukoreduction may be performed with respect to the whole blood during the draw phase of the operation. Turning to FIGS. 21 and 22, the draw line tubing 218 may include a leukocyte reduction filter 264 that is in line with the tubing 218. The filter 264 is located upstream of the first pump 238 so that the pump will exert a sufficient draw force on the blood to draw it through the filter 264 during collection. The leukofilter 264 may be located on the tubing segment 218 either upstream of where the anticoagulant is introduced into the system (as shown in FIG. 21) or downstream of where the anticoagulant is introduced into the draw line 218 (as shown in FIG. 22). Placement downstream of the anticoagulant junction allows the use of anticoagulant to flush any remaining whole blood from the filter 264 after the draw from the donor is completed. Also, placement of a leukoreduction filter in the draw line tubing 218 eliminates the need for a separate downstream leukoreduction filtration step, thus further streamlining the blood collection process.

The collection and separation method discussed above is a "single-pass" method, i.e., whole blood is withdrawn from the donor, and no separated blood components or other replacement fluid is returned. In keeping with another aspect of the disclosure, a method of simultaneously collecting whole blood from a donor and separating out the red blood cells using a spinning membrane separator is provided in which at least a portion of separated plasma is returned to the donor so that an increased quantity of red blood cells may be harvested from the donor.

Figure 22A:
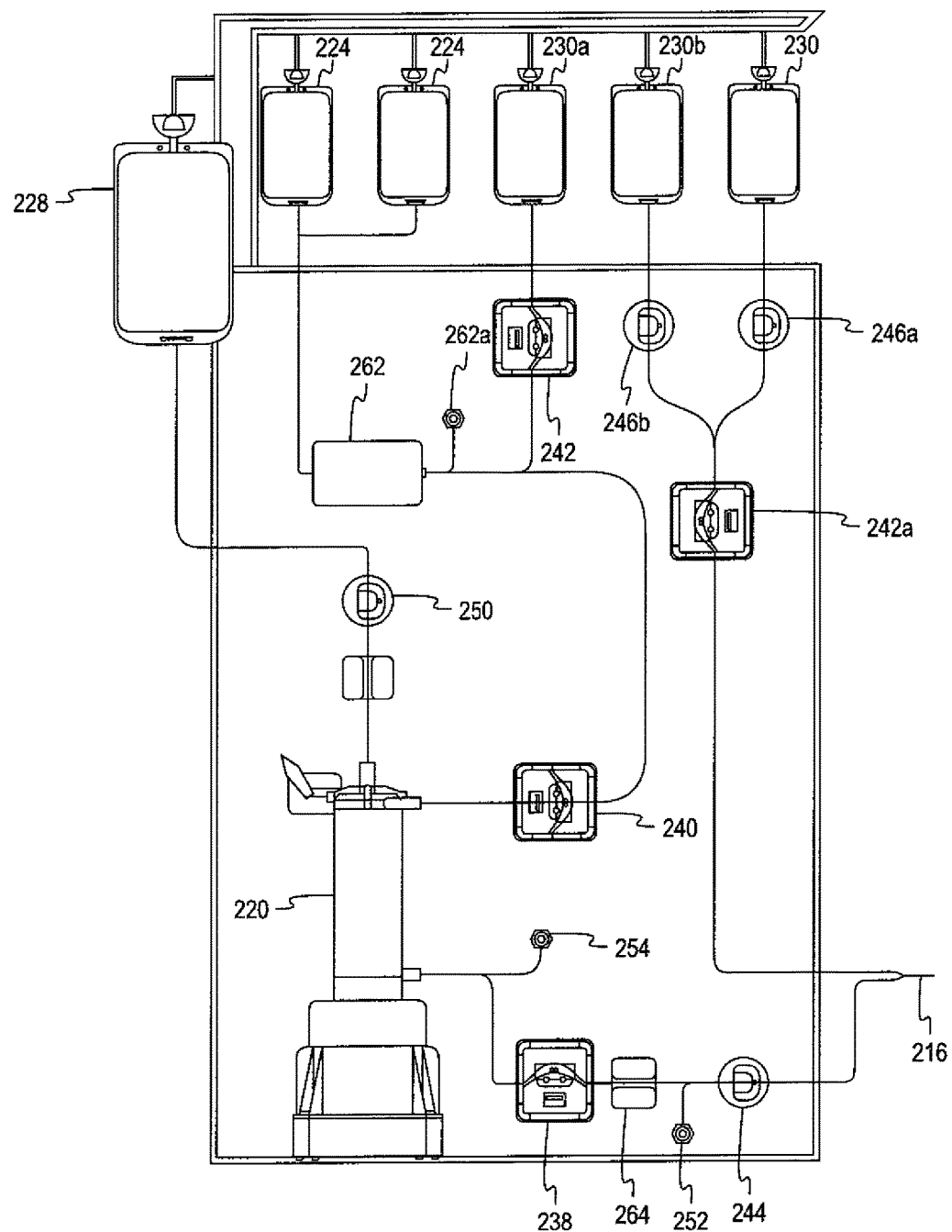
FIGS. 22A and 22B are schematic views of a further alternate embodiment of an automated whole blood collection system configured to be utilized for the collection of an increased volume of red blood cells.
Figure 22B:
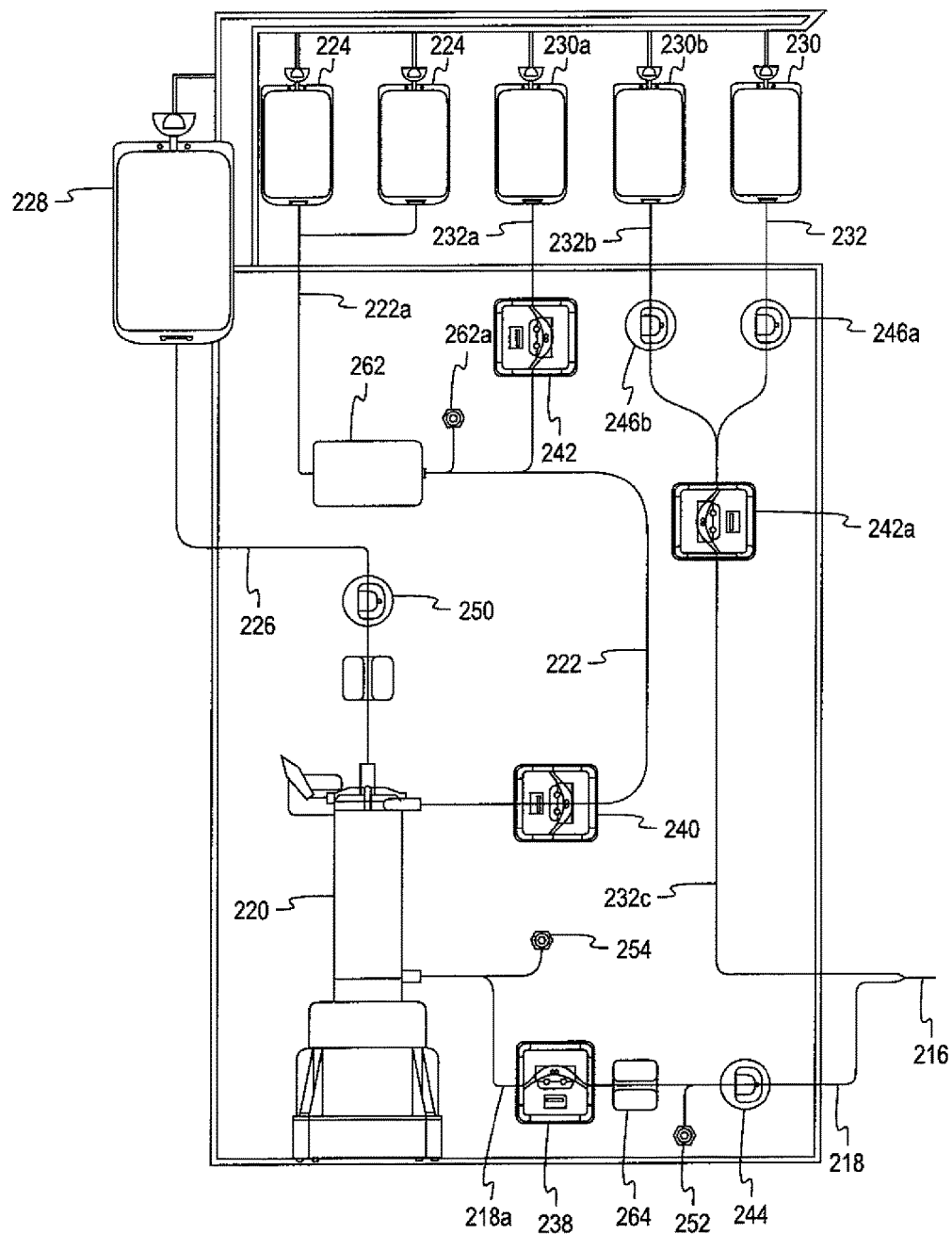

Specifically, the illustrated system and method utilize an invented spinning membrane separator as described above to produce up to two leukoreduced red blood cell products during an apheresis procedure. A schematic of one potential system layout is shown in FIG. 22A (in which primarily the durable hardware components are identified) and FIG. 22B (in which the disposable flow circuit components are identified). FIG. 22L depicts the disposable flow circuit or kit separately from the durable hardware component. FIGS. 22C-22H depict the cycles and flow paths of a double collection procedure utilizing the flow circuit illustrated in FIG. 22L. These figures represent one of many potential layouts, and various other component configurations are possible, as would be apparent to one skilled in the art.

As illustrated in FIGS. 22A-22I, the system comprises four pumps (inlet pump 238, outlet pump 240, additive solution pump 242, and saline/anticoagulant pump 242a), four clamps (donor clamp 244, anticoagulant clamp 246a, saline clamp 246b, and plasma clamp 250), three pressure sensors (donor pressure sensor 252, spinner pressure sensor 254 and filter pressure sensor 262a—the donor and spinner pressure sensors are generally considered to be required, while the filter pressure sensor is optional if filter clogging/plugging detection is desired), a leukofilter 262, and a spinning membrane separator 220. As illustrated, the spinning membrane separator 220 is in the "upside down" configuration, with the whole blood inlet located at the lower end of the separator and the plasma and red blood cell outlets located at the upper end, as described above. The system also optionally includes a hematocrit sensor 264, in the event that the operator is not able to input into the controller the donor hematocrit. Otherwise, a hematocrit sensor is not required.

The double red blood cell collection procedure includes a priming cycle and a first draw/separation cycle, generally as described above in connection with FIGS. 16-22. However, after the draw/separation cycle, the separated plasma is returned to the donor, and a second draw/separation cycle is performed, after which the separated plasma is again returned to the donor.

Figure 22C:
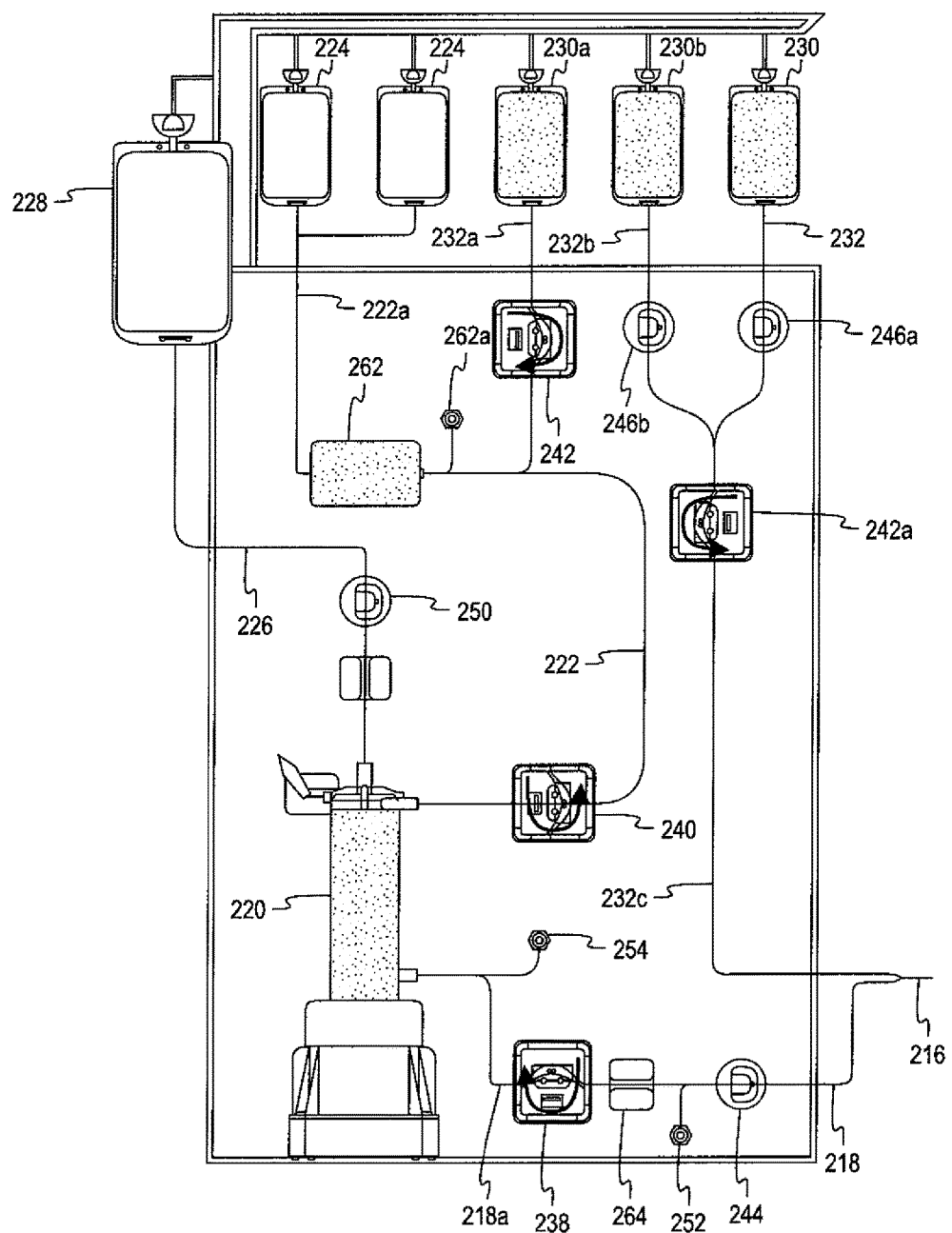
FIGS. 22C-22I illustrate the system of FIGS. 22A and 22B in various stages of operation.

Referring to FIG. 22C, the priming cycle is illustrated by which air is removed from the tubing of the kit and the membrane of the separator is wetted. Red blood cell additive solution is pumped out of the solution bag 230a and into the solution line 232a through the leukofilter 262 and into the red blood cell lines 222a by pump 242 (with the direction of rotation of the pump being indicated by the arrow associated therewith). Anticoagulant is pumped out of the anticoagulant bag 230 into the anticoagulant line 232 and saline is pumped out of the saline bag 230b into the saline line 232b by the pump 242a, with the saline/anticoagulant then being pumped through the saline/anticoagulant line 232c, the donor line 218, the inlet line 218a, the spinning membrane 220, the plasma line 226, and the outlet line 222 by means of pumps 238 and 240. Saline, rather than anticoagulant, is preferred for priming of the spinning membrane separator 220. If anticoagulant is used to prime the spinning membrane separator membrane, the citrate infusion rate during the first return to the donor of separated plasma would be higher than desirable.

After the priming cycle is completed, the first draw and separation cycle is performed, during which whole blood is drawn from the donor and separated into plasma and a leukoreduced red blood cell product. This cycle generates the first two red blood cell products that are to be collected. (If only a single red blood cell product is desired, the procedure is complete after this draw and separation cycle.)

Figure 22D:
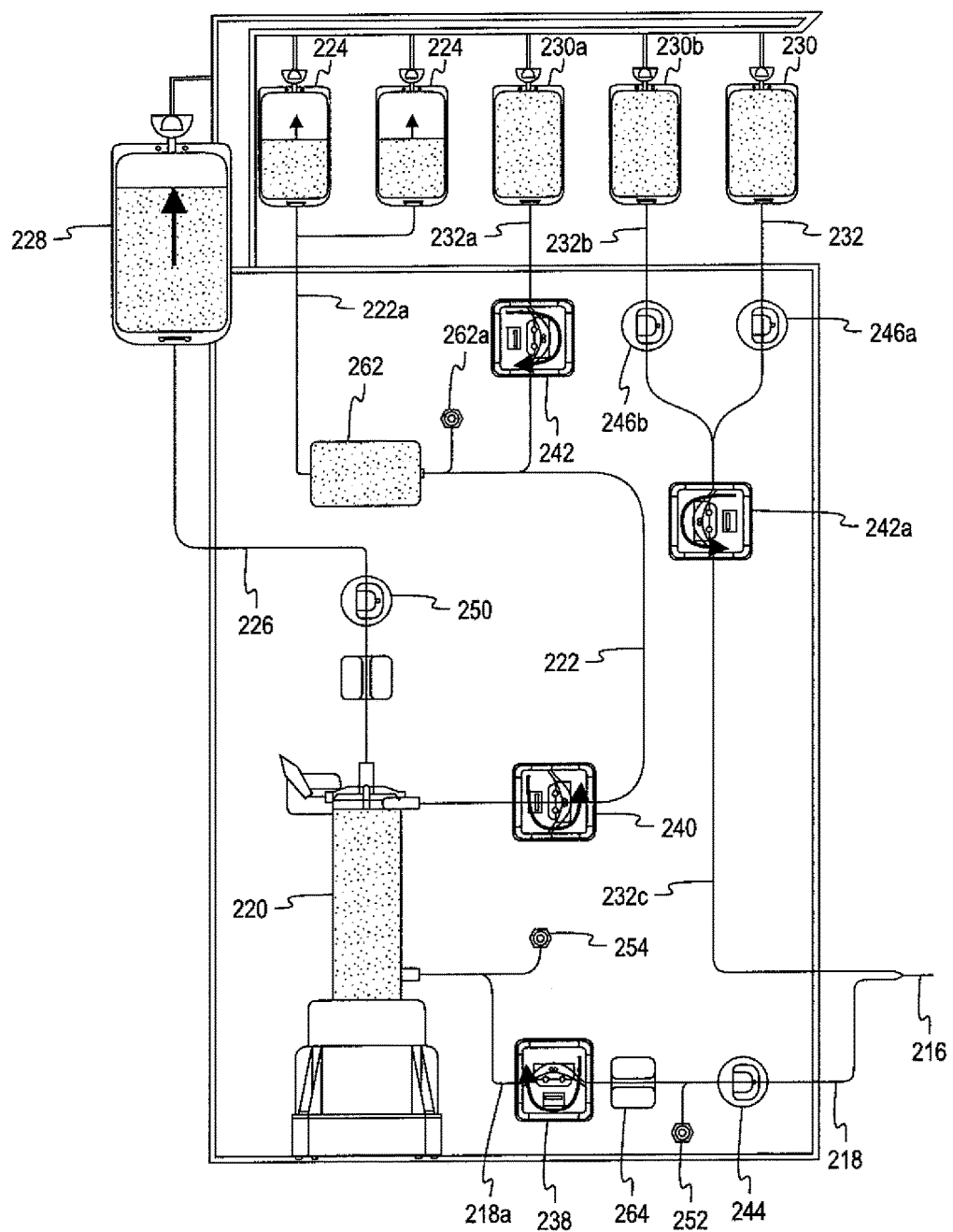

Referring to FIG. 22D, whole blood is drawn out of the donor and pumped into the spinning membrane device 220 by the inlet pump 238. The whole blood is separated into plasma and packed red blood cells (typically having a hematocrit of greater than 80%) by the spinning membrane 220. The red blood cells are passed through the leukofilter 262 as they exit the spinner 220 prior to entering the red blood cell product bags 224. The kit is configured to allow even distribution of the red blood cells into the two product bags 224. Leukoreduction during separation is preferred. However, the separated red blood cells could be flowed directly from the spinning membrane separator 220 into the product bags 224, and then leukofiltered at a later time after the donor is disconnected. During draw/separation cycle, the additive solution pump 242 is continuously pumping additive solution into the packed red blood cells as they exit the spinner 220 prior to entering the leukofilter 262. Adding additive solution to the packed red blood cells decreases the hematocrit of the blood within the filter, which decreases the possibility of hemolysis and microparticle generation within the filter 262. The saline/anticoagulant pump 242a is continuously pumping anticoagulant into the whole blood as it exits the donor to prevent clotting of the blood. This flow pattern is continued until a first red blood cell product has been collected.

The spinner pressure sensor 262 monitors the transmembrane pressure of the spinning membrane 220 and controls plasma flow through the membrane preferably according to the control algorithm disclosed in U.S. patent application Ser. No. 13/095,633, incorporated by reference above. The donor pressure sensor 252 monitors the vein pressure of the donor to detect vein occlusions. The filter pressure sensor 262a monitors the pressure across the leukofilter 262 to detect filter occlusions.

After the first draw/separation cycle is completed, a first plasma return cycle is performed, during which the plasma collected during the first draw/separation cycle is flowed back to the donor. (If only a single red blood cell product is desired, the separated plasma can be kept as a product, instead of being returned to the donor, as is the case in the procedures illustrated in FIGS. 16-22.)

Figure 22E:
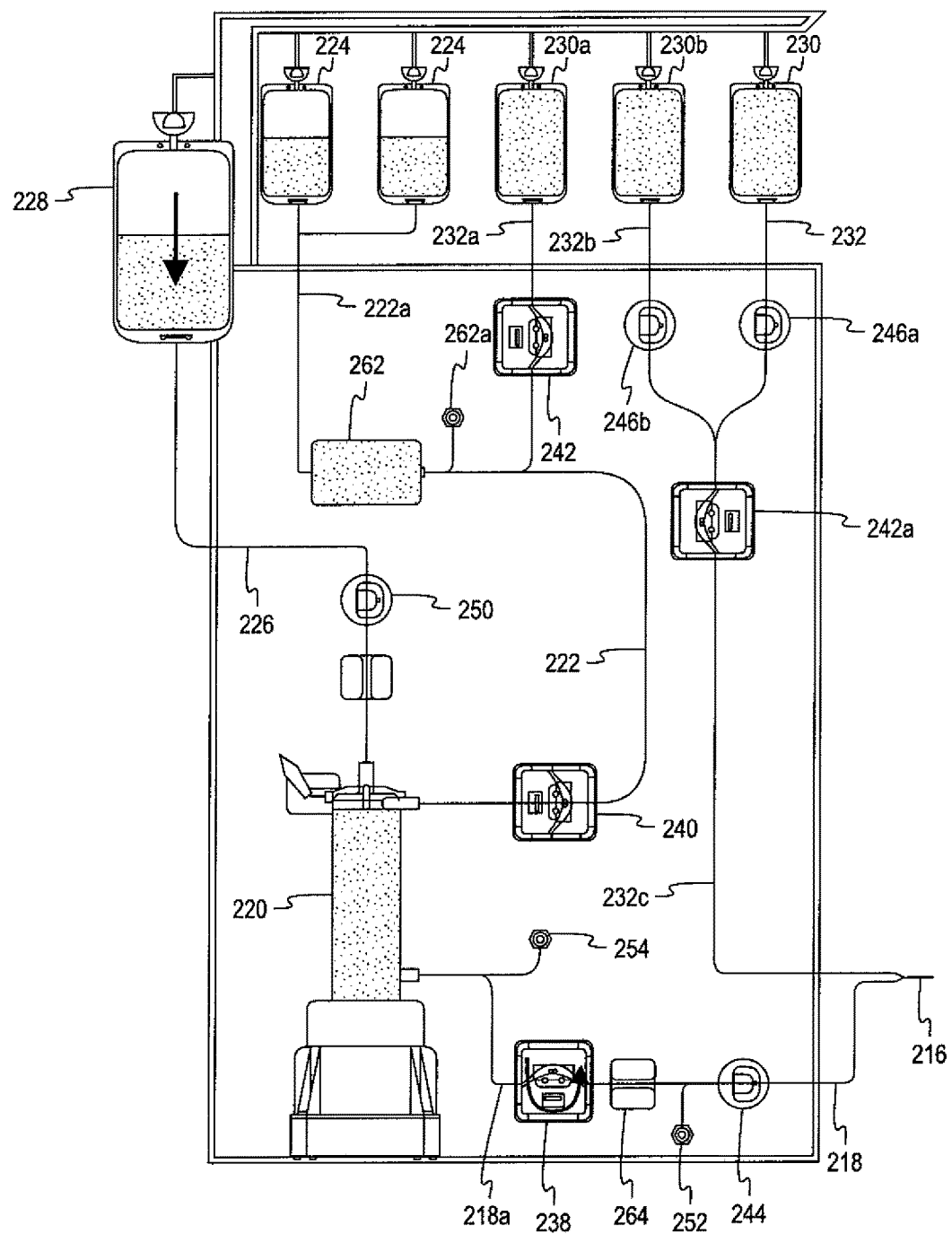

Turning to FIG. 22E, plasma is pulled out of the plasma bag 228 by the inlet pump 238. Plasma then flows back across the membrane in the separator 220 (reverse of the normal direction) through the inlet line 218a, the donor line 218, and back into the donor. The donor pressure sensor 252 monitors the donor's vein pressure. The plasma is returned to the donor until the plasma bag 228 is emptied. Once the first quantity of separated plasma is returned, the first cycle is complete, with one red blood cell product having been collected.

Figure 22F:
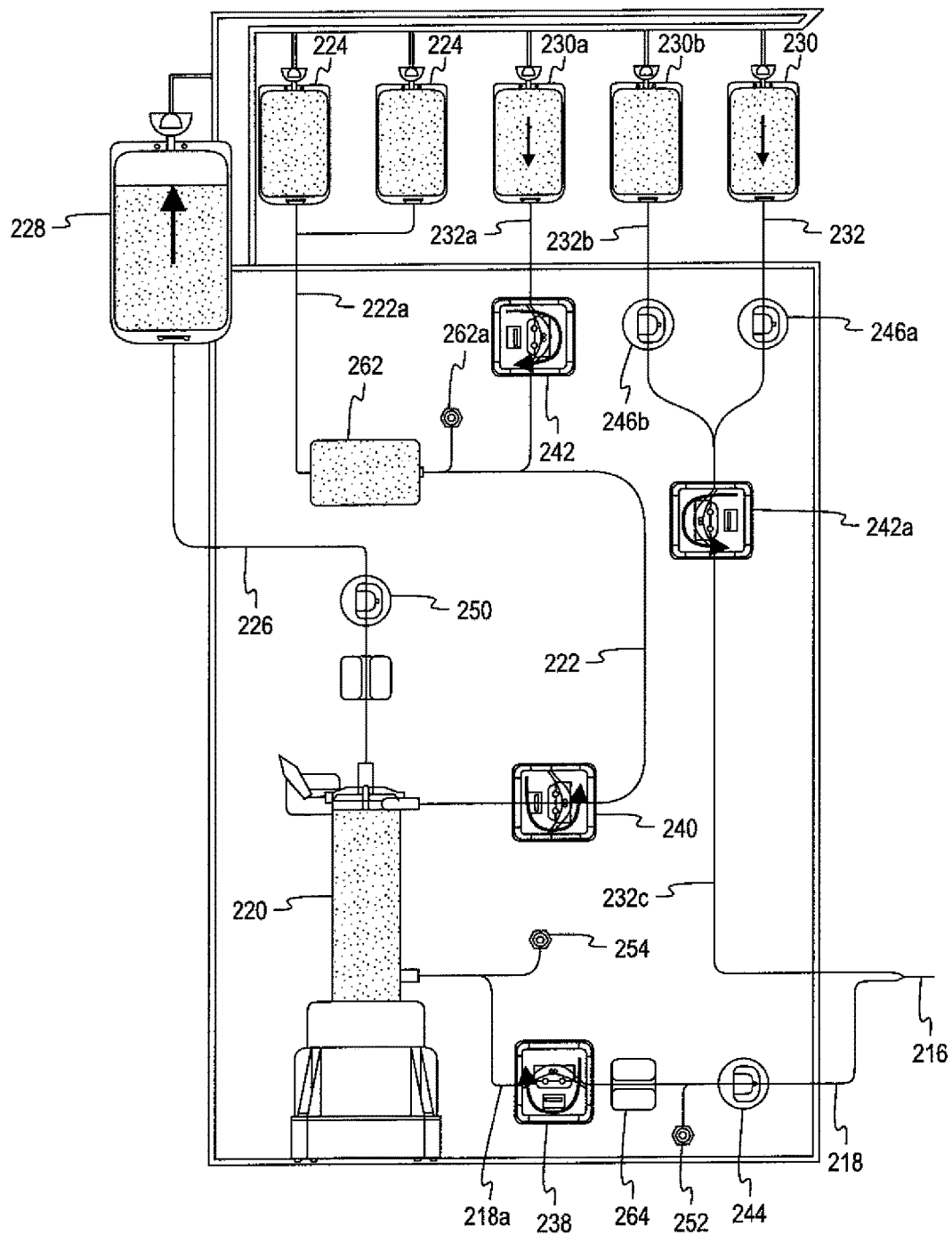
Figure 22G:
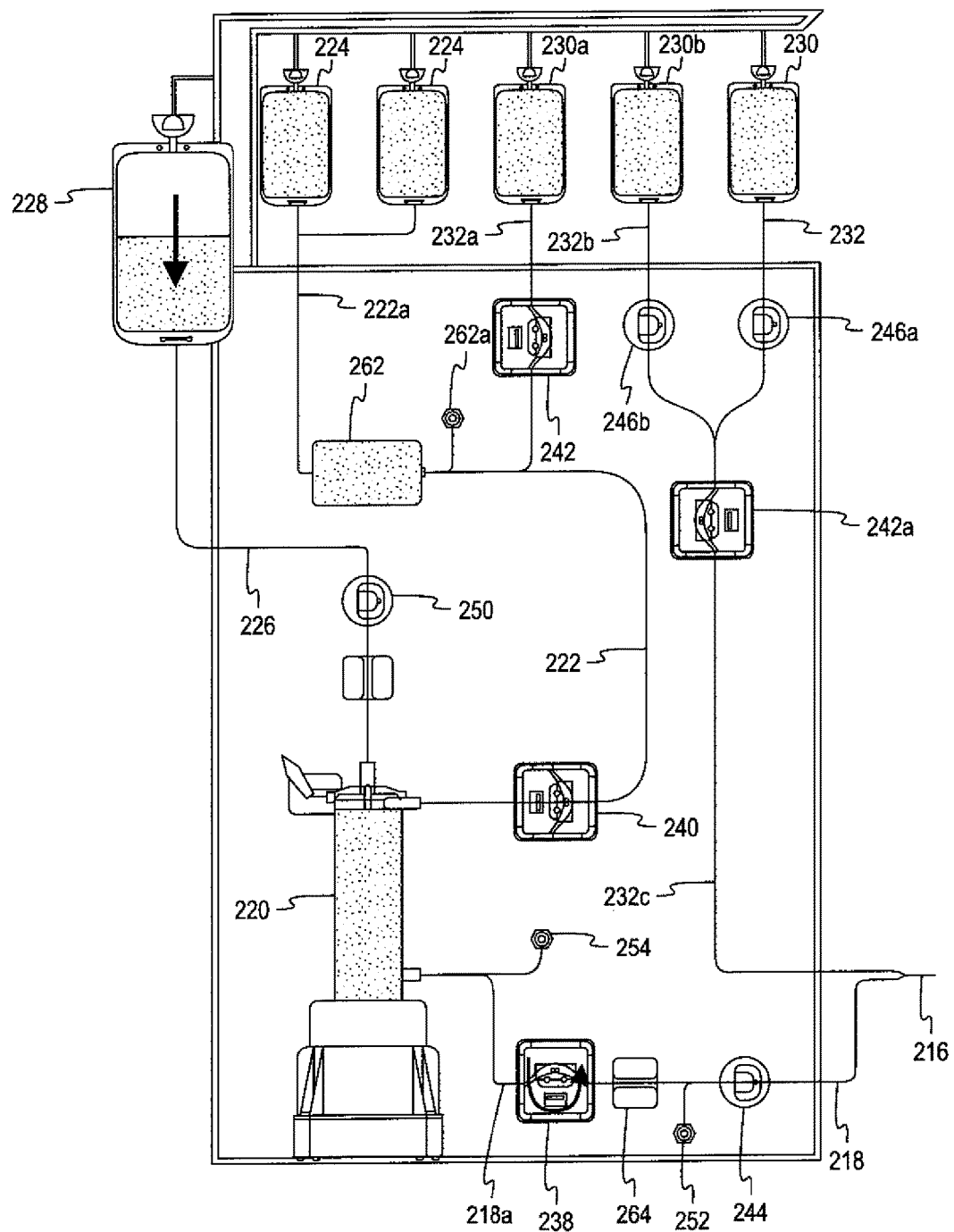

Upon completion of the first cycle, a second cycle is commenced that includes the draw/separation and plasma return steps substantially as discussed above with reference to FIGS. 22D and 22E to collect the second of the two red blood cell products. The second draw/separation step is shown in FIG. 22F, with the red blood cell collection bags 224 being filled upon completion, and the flow paths are the same as described in connection with FIG. 22E. A second plasma return cycle is performed to return the plasma collected during the second draw/separation cycle back to donor, as shown in FIG. 22G, with the flow paths being the same as described in connection with FIG. 22E.

After the second quantity of plasma is returned to the donor, saline may be flowed to the donor. After the total desired volume of red blood cells is collected, the leukofilter 262 may be flushed with storage/additive solution to recover red blood cells and increase product volume to meet requirements.

Figure 22H:
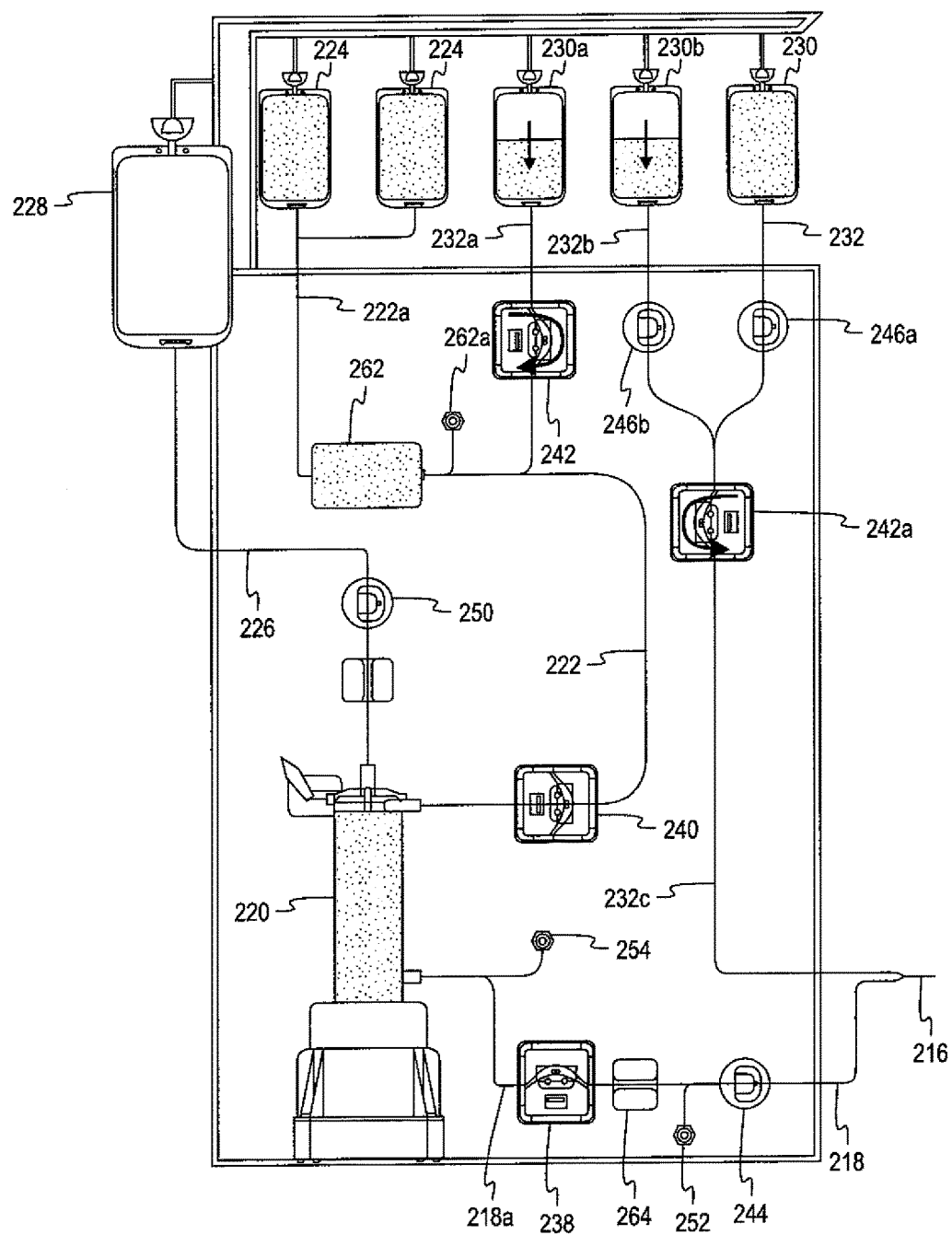

With reference to FIG. 22H, the saline return and filter flush can occur simultaneously. Saline is pumped out of the saline bag 230b by the saline/anticoagulant pump 242a directly into the donor. Saline can also be used to rinse residual plasma out of the spinning membrane 220, the inlet line 218*a*, and the donor line 218 if it is necessary to recover this plasma. Additive solution is pumped out of the solution bag 230*a* by the solution pump 242 through the leukofilter 262 and into the red blood cell product bags 224. Once these steps are completed the procedure is complete.

Figure 22I:
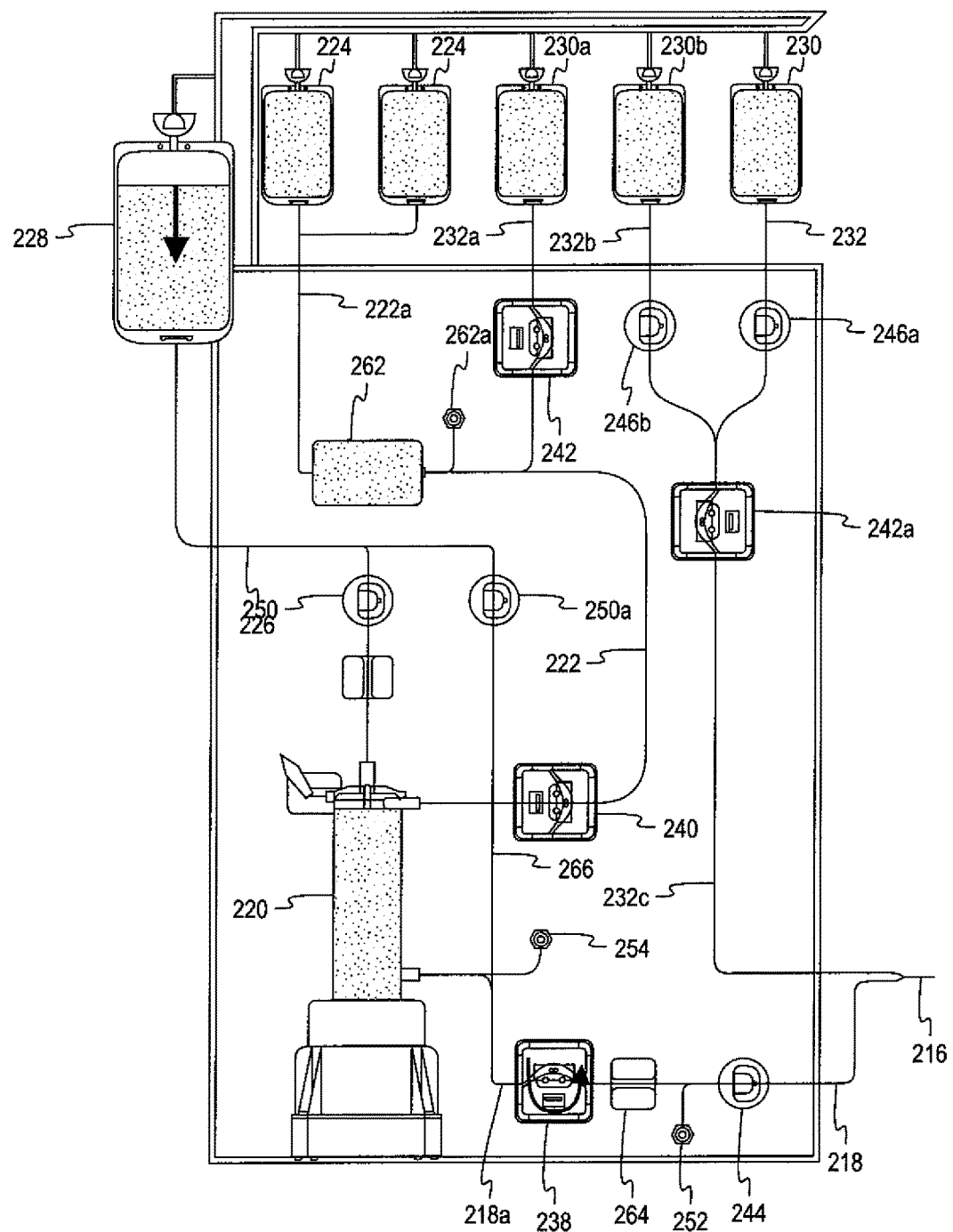

As described above, the return flow path for the plasma passes through the membrane of the separator 220 as it is returned to the donor. This is the preferred route as it is the most direct. However, a separate plasma return flow path may be provided that bypasses the separator, as shown in FIGS. 22I and 22K. This requires a line 266 that bypasses the spinning membrane separator and an additional plasma clamp 250*a*.

The procedure for the collection of a double red blood cell product described above is a batch process in which the whole blood is separated and components collected only during the draw cycles. Unwanted components, such as plasma, are returned to the donor during return cycles, during which separation of blood is postponed. Continuous batch processing, in which whole blood is continuously separated during both the draw and return cycles, is preferable, as the return rate of separated plasma, which varies from donor to donor, will not affect procedure times. Further, slower separation rates may be used, which improves separation efficiency.

Figure 22J:
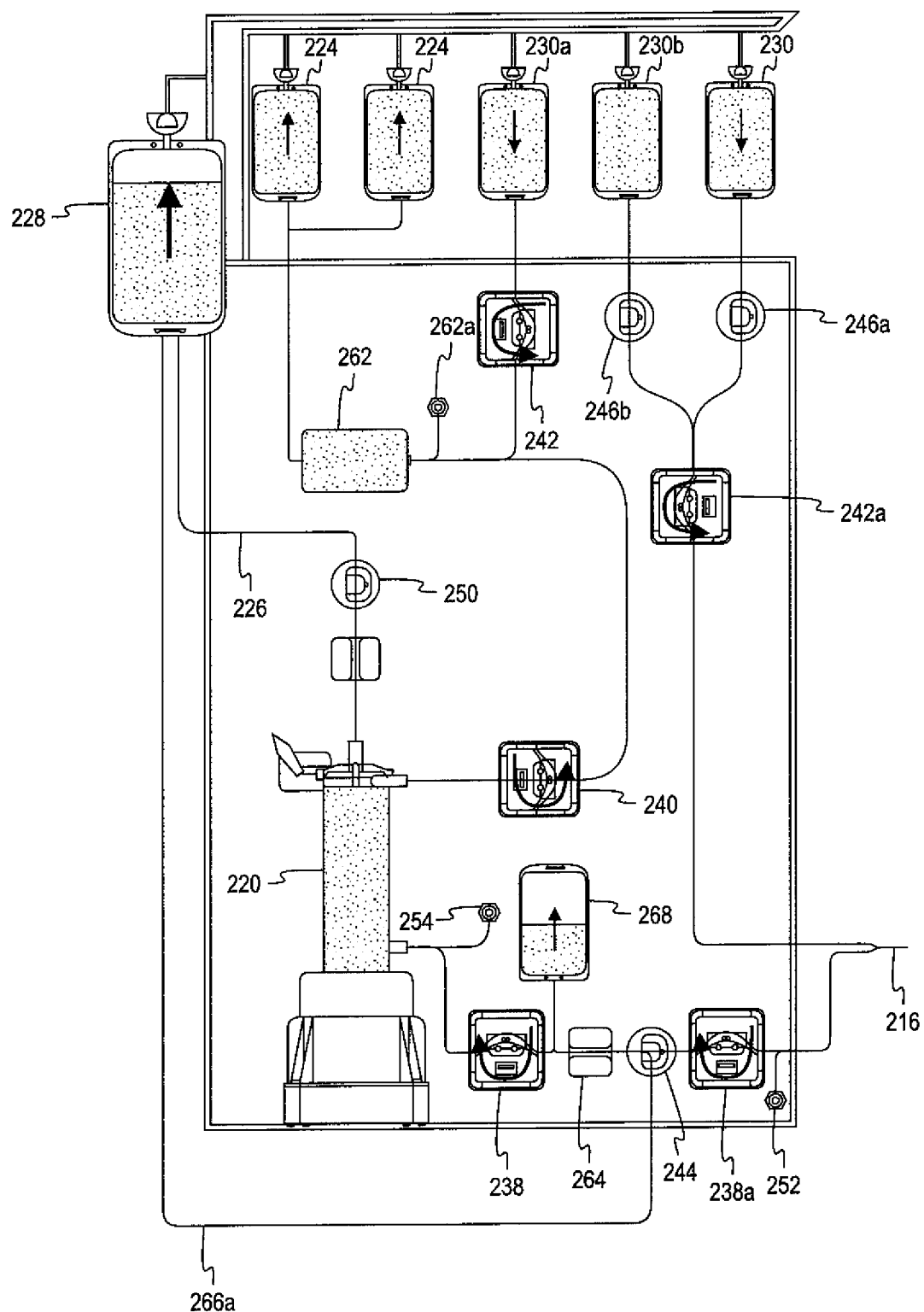
FIGS. 22J and 22K and are schematic views of an embodiment of an automated whole blood collection system for the collection of an increased volume of red blood cells that allows for the simultaneous separation of whole blood and the return of plasma to the donor.
Figure 22K:
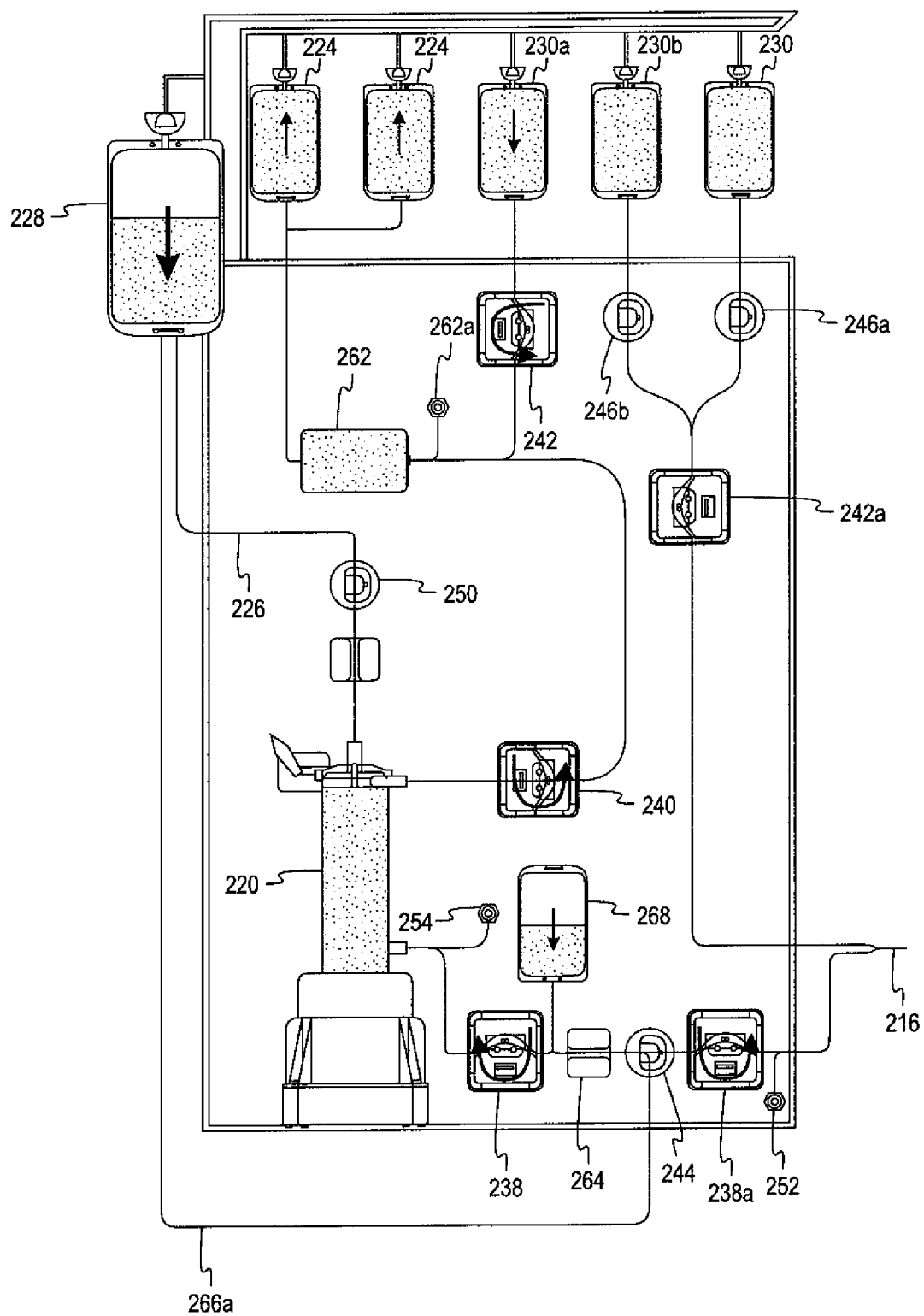
Figure 22L:
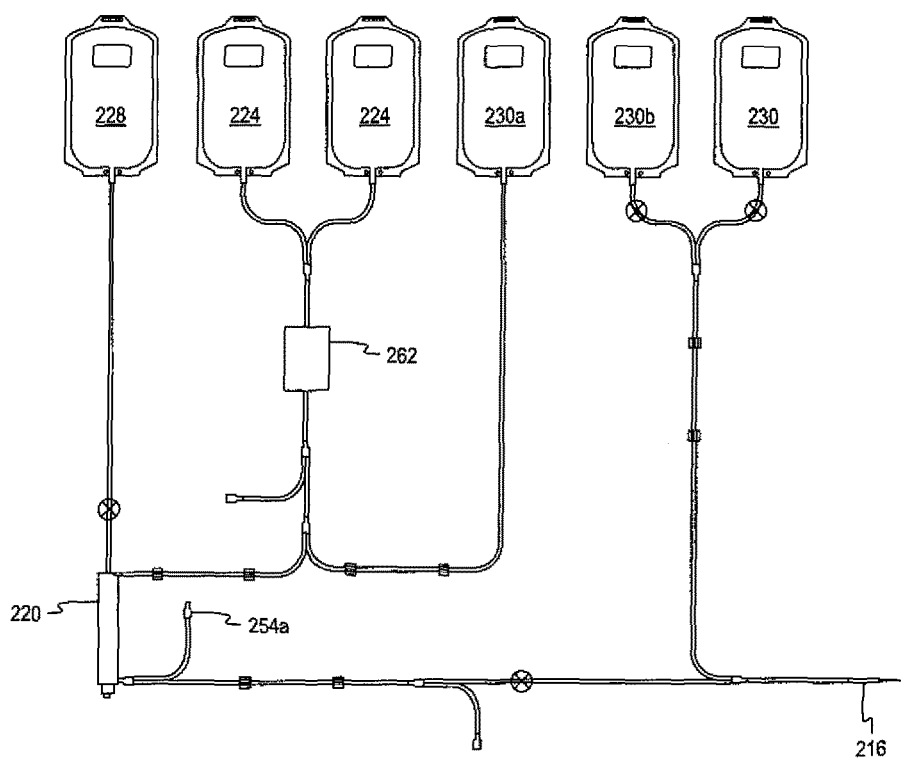
FIGS. 22L, 22M, and 22N illustrate embodiments of disposable fluid circuits for use in the systems of FIGS. 22A, 22I, and 22J, respectively.
Figure 22M:
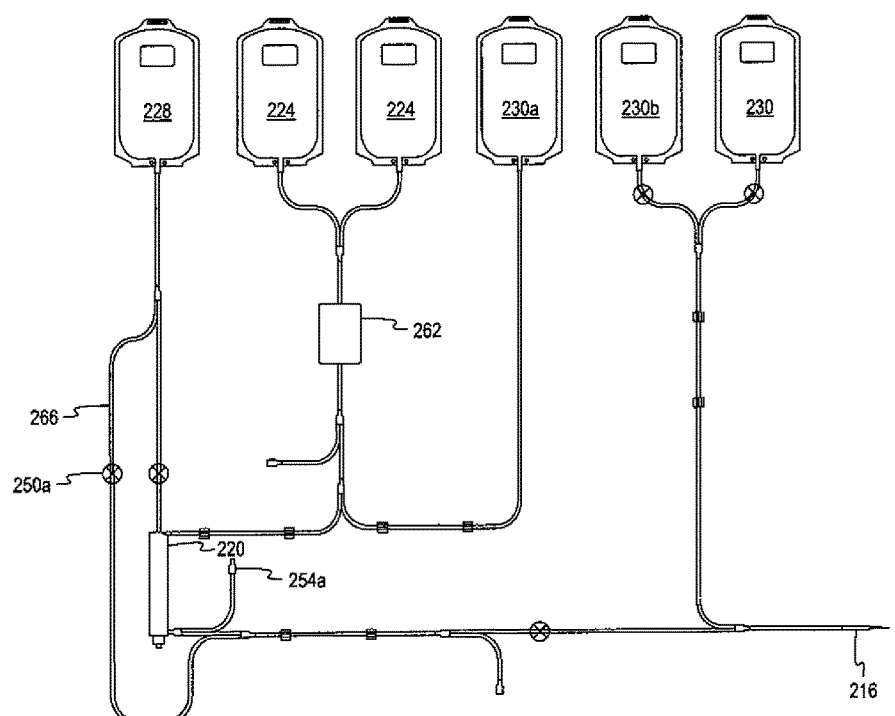
Figure 22N:
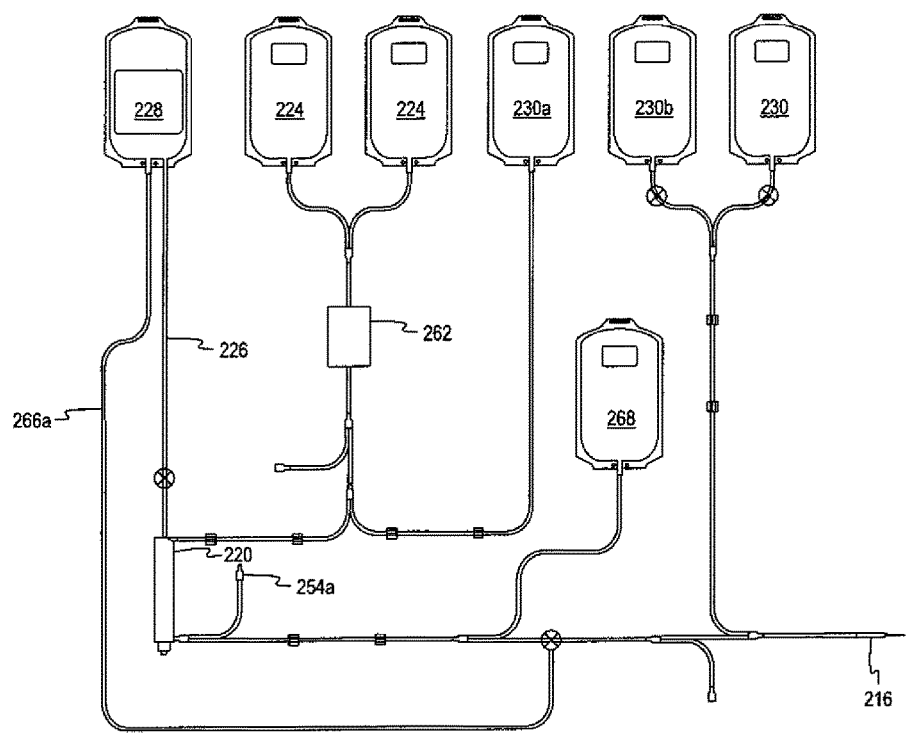

With reference to FIGS. 22J, 22K, and 22N, continuous batch processing may be accomplished by adding to the disposable fluid circuit described in connection with FIGS. 22A and 22B an in-process reservoir 268 upstream of the separator 220 and a separate plasma return line 266*a* connecting the plasma bag 228 to the donor line 216, and adding to the hardware device an additional inlet pump 238*a* that engages the donor line upstream of the in-process reservoir 268. Other aspects of the hardware device and processing kit of FIGS. 22A and 22B are unchanged.

With reference to FIG. 22J, the draw cycle of a continuous batch process is shown. In general, whole blood is withdrawn from the donor through the donor line 216 by the draw/return pump 238*a* and then flowed into the in-process reservoir or bag 268. Whole blood is then pumped from the in-process bag 268 by the inlet pump 238 and into the spinning membrane separator 220, where plasma is separated from the cellular components and flowed through tubing 226 into the plasma bag 228.

Preferably, the draw/return pump 238*a* draws whole blood from the donor into the in-process bag 268 at a flow rate greater than the flow rate at which the inlet pump 238 flows whole blood out of the in-process bag 268 and into the spinning membrane separator 220. The difference between the rate of the draw/return pump 238*a* and the rate of the inlet pump 238 is the rate at which the in-process bag 268 will fill with whole blood during the draw cycle. Preferably, the in-process bag 268 is filled with whole blood during the initial draw cycle to have whole blood available for separation during the subsequent return cycle, described below. The draw cycle preferably continues until the plasma bag 228 is substantially filled.

With reference to FIG. 22K, the return cycle is shown. During the return cycle, whole blood continues to be pumped from the in-process bag 268 into the spinning membrane separator by the inlet pump 238, and the plasma that is separated from the cellular components is flowed into the plasma bag 228 through tubing 226. Simultaneously, plasma collected during the previous draw cycle is flowed out of the plasma bag 228 through the plasma return line by the draw/return pump 238*a* and returned to the donor.

Preferably, the rate at which plasma is returned to the donor is greater than the rate at which plasma is being separated from the cellular components by the spinning membrane separator 220, thus allowing the plasma bag 228 to empty. Whole blood continues to be separated and plasma returned to the donor until the plasma bag 228 empties. If the in-process bag 268 empties before the plasma bag 228 empties, separation stops until the commencement of the next draw cycle. The draw/return cycles will continue until the desired amount of red blood cells has been collected.

As described above, the return flow path for the plasma passes through the membrane of the separator 220 as it is returned to the donor. This is the preferred route as it is the most direct. However, a separate plasma return flow path may be provided that bypasses the separator, as shown in FIGS. 22I and 22M. This requires a line 266 that bypasses the spinning membrane separator and an additional plasma clamp 250*a*.

The automated whole blood collection system and method described herein are expected to improve blood collection center efficiency, and decrease the operational costs, by accomplishing the separation of whole blood into red blood cell and plasma components without the need for subsequent manual operations. Further, the use of smaller-gauge needles in the donor access devices used with the system should enhance donor comfort, while the use of a draw pump allows the system to achieve donation times similar to typical whole blood collection. Additionally, by having the whole blood collection controlled by microprocessor, greater opportunities for data management are provided that are not typically found in current manual whole blood collection methods, including the use of integrated bar code readers and/or RFID technology, as described above.

In accordance with another aspect of the disclosure, methods, systems, and devices useful in the washing of biological cells, such as blood cells or other blood or biological components, are described below.

VI. Systems and Methods for Cell Washing

Biological cell washing may serve several purposes. For example, cell washing may be used to replace the liquid medium in which biological cells are suspended. In this case, a second liquid medium is added to replace and/or dilute the original liquid medium. Portions of the original liquid medium and the replacement liquid medium are separated from the cells. Additional replacement liquid media may be added until the concentration of the original liquid medium is below a certain percentage. Thereafter, the cells may be suspended in, for example, the replacement medium.

Cell washing may also be used to concentrate or further concentrate cells in a liquid medium. The cells suspended in a liquid medium are washed, such that a portion of the liquid medium is separated and removed from the cells.

Furthermore, cell washing may be used to remove undesired particulates, such as gross particulates or unwanted cellular material from a cell suspension of a particular size or "purify" a desired cell suspension or other liquid.

The method, systems, and apparatus described below may be employed to wash cells for any of the above-described reasons. More particularly, but without limitation, the methods, systems and apparatus described below may be used to wash blood cells such as red blood cells or white blood cells (leukocytes), or platelets.

In one particular embodiment, a suspension including white blood cells in a liquid culture medium may be washed to replace the liquid culture medium with another medium, such as saline, prior to use or further processing. The cell suspension including white blood cells in a liquid culture medium is delivered and introduced into a separator, such as a spinning membrane separator. The spinning membrane separator has a membrane filter with a pore size smaller than the white blood cells. In one embodiment, a liquid wash medium including the replacement liquid medium, such as saline, is also added to the separator to dilute the liquid culture medium. The separator is operated such that the liquids pass through the pores of the membrane and are extracted as waste. In this embodiment, as the liquid is extracted, the wash medium is added, such that the resulting cell suspension includes white blood cells suspended in the replacement liquid medium (e.g., the saline).

In another embodiment, the cell suspension may be concentrated (by removing supernatant) and collecting the concentrated cell suspension in a container of the processing set. Replacement fluid may be introduced into the separator, combined with the concentrated cells in the container and the cells then resuspended with the replacement fluid. If necessary, the resuspended cells/replacement fluid may be introduced into the separator to further concentrate the cells, remove supernatant, and resuspend the concentrated cells with additional replacement fluid. This cycle may be repeated, as necessary.

Similar processes may be used to wash red blood cells suspended in a liquid storage medium. The cell suspension including red blood cells suspended in a liquid storage medium may be washed to replace the liquid storage medium with another medium, such as saline, prior to use or further processing. The cell suspension is delivered and introduced into a separator, such as a spinning membrane separator. The spinning membrane separator has a membrane filter with a pore size smaller than the red blood cells. In one embodiment, a wash medium, i.e., replacement liquid medium, such as saline, may also be added to the separator to dilute the liquid storage medium. The separator is operated such that the liquid passes through the pores of the membrane and is extracted as waste. As the liquid is extracted, the wash medium is added, such that the resulting cell suspension includes red blood cells suspended in the replacement liquid medium (i.e., the saline). The wash and/or replacement liquid may also be a storage medium that includes nutrients and other components that allow for the long-term storage of the cells. Alternatively, in another embodiment, the red blood cells may first be concentrated and removed to a container, as generally described above. Replacement fluid may then be combined with the red blood cells in the container. The replacement fluid may be directly introduced into the container, or introduced into and through the separator and then into the container.

The systems, methods, and apparatus for cell washing described herein utilize a disposable set that includes a separator, such as a spinning membrane separator. The disposable set with the spinning membrane separator is mounted onto the hardware component of the system, i.e., separation device. The separation device includes clamps, pumps, motors, air detecting sensors, pressure transducer sensors, Hb detectors, weight scales, and a control logic/microprocessor included in a microprocessor. The control logic/microprocessor receives input data and signals from the operator and/or the various sensors, and controls the operation of the clamps, pumps and motors.

The cell suspension to be washed, i.e., cells suspended in a medium, may be provided in a sterile, disposable source container, which is connected, in sterile fashion, to the disposable set. A wash medium, such as saline or other suitable liquid, is also connected in sterile fashion or pre-attached to the disposable set. The control logic of the device operates the clamps and pumps to circulate the cell suspension through the tubing of the disposable set to the (spinning membrane) separator. The separation device, through its control system, also directs the wash solution through the tubing of the disposable set to the spinning membrane separator. The cell suspension and the wash solution may be mixed within the spinning membrane separator, may be mixed prior to entering the spinning membrane separator, or may be combined in a container after the cell suspension has been concentrated. Within the spinning membrane separator, the suspension medium is separated from the cells suspended therein. The suspension medium and remaining wash medium (if the suspension medium and wash medium have been combined) exits through a waste port, while the cells pass through a separate exit port.

If further washing and dilution is necessary, the washed cells may be re-circulated through the separator with an additional volume of the wash solution. In one embodiment, the cells that are to be "re-washed" may be transferred to one or more in-process containers, as will be described below. The control logic of the device operates clamps and pumps to circulate the cell suspension from the in-process container through tubing to an inlet of the spinning membrane separator or to an inlet of a second spinning membrane separator. Further wash medium is added, and the process repeats until an acceptable amount or concentration of the cells is achieved. The final cell suspension containing the cells is preferably collected in a final product container.

Figure 23:
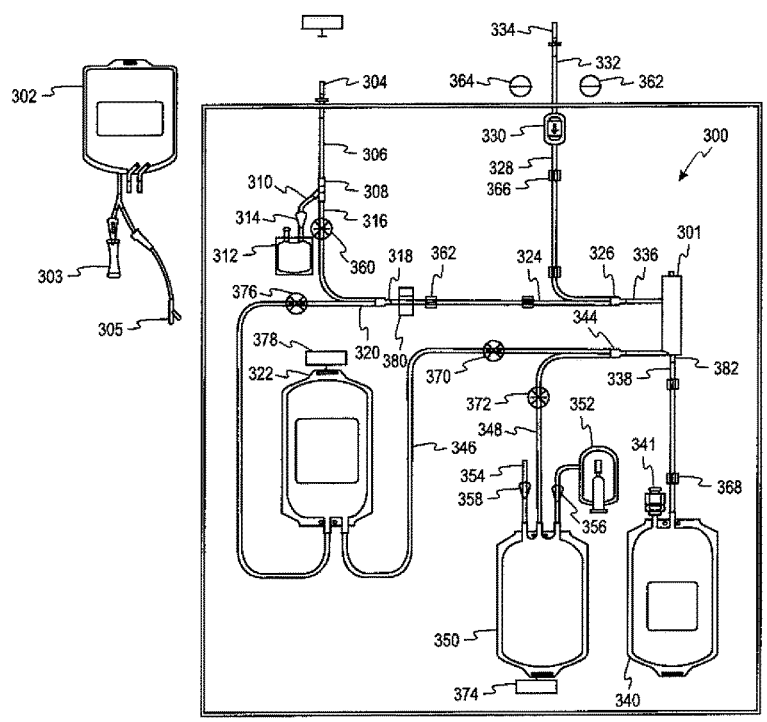
FIG. 23 shows a disposable set useful in the washing of cells in accordance with the method disclosed herein.
Figure 24:
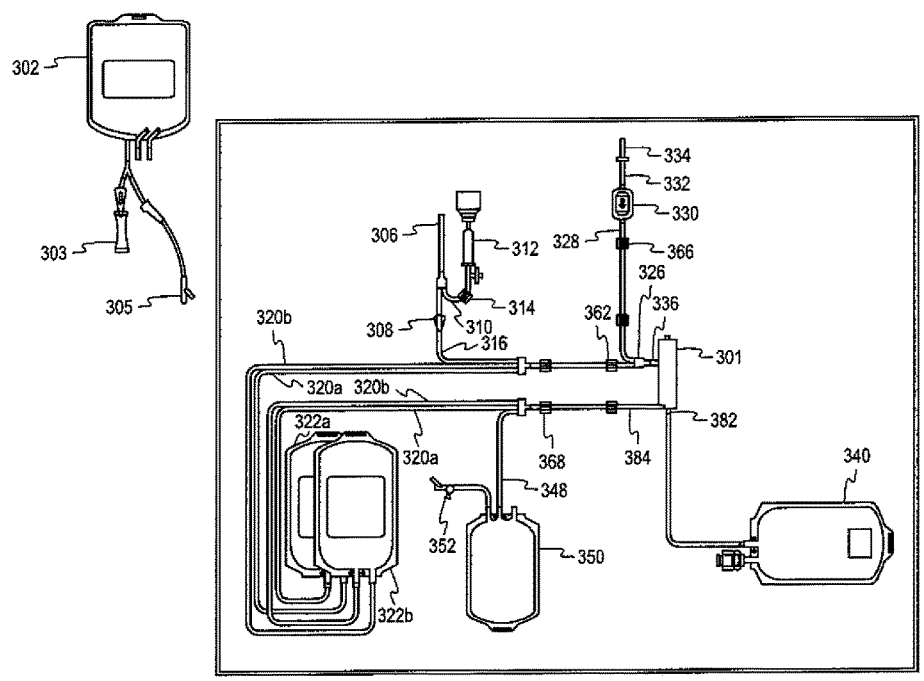
FIG. 24 shows another embodiment of a disposable set useful in the washing of cells in accordance with an alternative method disclosed herein.
Figure 25:
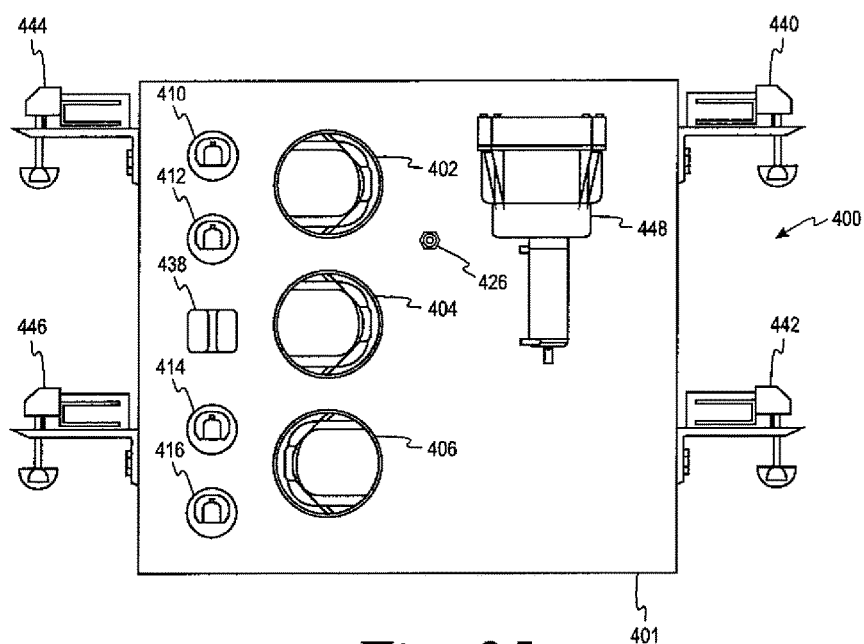
FIG. 25 shows an embodiment of the control panel of a device useful in the washing of cells in accordance with the method disclosed herein.

In accordance with the present disclosure, FIGS. 23-25 show exemplary systems useful in the washing of biological cells, such as, but not limited to, red blood cells and white blood cells. As noted above, the specific embodiments disclosed are intended to be exemplary and non-limiting. Thus, in one embodiment, the system described herein includes a disposable set 300 (FIG. 23 or 24) and hardware component or device 400 (FIG. 25). It will be appreciated that the disposable processing sets 300 shown in both FIGS. 23 and 24 are, in many respects, identical and common reference numerals are used in both FIGS. 23 and 24 to identify identical or similar elements of the disposable processing sets. To the extent that disposable processing sets differ in structure or in their use, such differences are discussed below. Disposable set 300 is mounted onto device 400 (FIG. 25), which is described in greater detail below.

As shown in FIGS. 23-24, separator 301 is integrated into the exemplary disposable set 300. Additionally, as will be described in greater detail below, disposable set 300 includes tubing, Y-connectors, in-process bag(s), sample pouch(es), final product bag(s), waste bag(s), and sterile filter(s).

The cell suspension to be washed is typically provided in a source container 302, shown in FIGS. 23 and 24 as disconnected from the disposable set. As noted above, source container 302 may be attached (in sterile fashion) at the time of use. Source container 302 has one or more receiving ports 303, 305, one of which may be adapted to receive spike connector 304 (FIG. 23) of disposable set 300. More particularly, source container 302 is connected to the disposable set 300 via the spike connector 304, which is connectable to access port 303. More preferably, however, source containers (and the fluid therein) may be free of a spike connector (as shown in FIG. 24) and accessed in a sterile manner by employing sterile docking devices, such as the BioWelder, available from Sartorius AG, or the SCD IIB Tubing Welder, available from Terumo Medical Corporation. A second access port 305 may also be provided for extracting fluid from the source bag 302.

As further shown in FIGS. 23-24, tubing segment 306 may optionally include a sampling sub-unit at branched-connector 308. One branch of branched-connector 308 may include a flow path 310 leading to sample pouch or site 312. Sample pouch or site 312 allows for the collection of a sample of the incoming source fluid. Flow to the sample pouch or site 312 is typically controlled by clamp 314. The other branch of branched-connector 308 is connected to tubing 316. Tubing 316 is connected to further downstream branched-connector 318. Branched-connector 318 communicates with tubing 316 and tubing 320, which provides a fluid flow path from in-process bag 322, described in greater detail below. Tubing segment 324 extends from one of the ports of branched-connector 318 and is joined to a port of further downstream branched-connector 326. A separate flow path defined by tubing 328 is also connected to a port of branched-connector 326. Tubing 328 may include an in-line sterile barrier filter 330 for filtering any particulate from a fluid before it enters the flow path leading to second branched-connector 326 and, ultimately separator 301.

In accordance with the system disclosed herein, a wash solution may be attached (or pre-attached) to set 300. As shown in FIGS. 23 and 24, tubing 332 (defining a flow path) preferably includes spike connector 334 at its end. Spike connector 334 is provided to establish flow communication with a container of a wash fluid, such as a disposable bag containing saline or other solution (not shown). The wash medium or fluid flows from the wash fluid source, through the second spike connector 334, through tubing segment 332, where it is filtered by the sterile barrier filter 330 described above, and then passes through tubing 328 to the input of the branched-connector 326 described above.

Tubing segment 336 defines a flow path connected at one end to a port of branched-connector 326 and to an inlet port of the separator 301. Preferably, in accordance with the present disclosure, separator 301 is a spinning membrane separator of the type described above.

As shown in FIGS. 23, 24 and 25, the spinning membrane separator 301 has at least two outlet ports. Outlet 646 of separator 301 receives the waste from the wash (i.e., the diluted suspension medium) and is connected to tubing 338, which defines a flow path to waste product container 340. The waste product container includes a further connection port 341 for sampling or withdrawing the waste from within the product container.

Separator 301 preferably includes a second outlet 648 that is connected to tubing segment 342. The other end of tubing segment 342 is connected to branched-connector 344, which branches into and defines a flow path to one or more in-process containers 322 and a flow path to a final product container 350. The final product container 350 may also include a sample pouch 352 (see FIG. 23) and an access port or luer connector 354. Sample pouch 352, shown with a pre-attached tube holder 352 in FIG. 23, allows for sample collection of the final product. Flow control to the sample pouch 352 is preferably controlled by clamp 356. The flow path through the access port 354 is controlled by clamp 358.

Turning now to the method of washing using the kit 300 of FIGS. 23 and 24, the disposable set 300 is first mounted onto panel 401 of the separation device (i.e., hardware) 400, shown in FIG. 25. Device 400 includes peristaltic pumps, clamps, and sensors, which control the flow through the disposable set. More specifically, control of the pumps, clamps and the like is provided by a software-driven microprocessor/controller of device 400. Tubing segments 362, 366 and 368 (shown in FIG. 23) are selectively mated with peristaltic pumps 402, 404, or 406 (shown in FIG. 25). (Waste line pump segment 368 may be relocated to separator outlet line 342, if desired.) Once the disposable set 300 is mounted onto the control panel 401 of device 400, the cell suspension in product bag 302 is attached, as previously described, by spike connector 304 or by sterile connection. A wash medium provided in a container (not shown) is likewise attached. In accordance with the operation of device 400, clamp 360 is opened and allows the cell suspension to flow from the product container 302.

Flow of the cell suspension is advanced by the action of peristaltic pump through the tubing 324 designated by the pump segment 362 and into the spinning membrane separator 301. Similarly, wash medium is advanced by the action of peristaltic pumps through the length of tubing 328 designated by the pump segment 366 with valves 362 and 364 in an open position. The wash medium flows through tubing 332, the sterile barrier filter 330, tubing 328, Y-connector 326, and into the spinning membrane separator 301. The wash medium and the cell suspension may be sequentially introduced into spinning membrane separator 301, allowing for mixing of the suspension and wash solution to occur within the chamber (gap) of separator 301 or in in-process container 322, as described below. Alternatively, the wash medium and cell suspension may be combined prior to introduction into separator 301 at (for example) the second branched-connector 326.

In yet a further alternative, cell suspension may first be introduced from source container 302 into separator 301, as generally described above. Cell suspension is concentrated within separator 301, allowing supernatant to pass through membrane, through outlet port 382, to waste product container 340. Concentrated cells exit separator 301 through port 384 and are directed to in-process container 322.

Once separation of concentrated cells from supernatant of the cell suspension is completed, replacement fluid is introduced from a replacement fluid container (not shown) into separator 301 (to flush out any residual cells) and is likewise directed through port 384 to in-process container 322. The concentrated cells are resuspended in the replacement fluid within in-process container 322, as shown in FIG. 23. If additional washing is desired or required, the system may be pre-programmed or otherwise controlled to (re)introduce the resuspended cells/replacement fluid into separator 301, wherein the separation of concentrated cells from supernatant is repeated. The final cell product is collected in final product container 350, where it may be resuspended with additional replacement fluid.

Regardless of the sequence of cell suspension/wash solution introduction or the disposable set used, the spinning action of the device causes cells to separate from the remainder of the fluid in which it was suspended and/or from the wash solution. Preferably, the supernatant and the wash solution pass through the membrane while the desired cells are concentrated within the chamber of the separator. The waste resulting from the separation, which includes wash medium and supernatant medium, exits port 382 and flows through tubing 338 to waste product container 340. The flow of waste is controlled by peristaltic pump through a portion of tubing 338 designated by the pump segment 368 to the waste product bag 340.

As described above, the concentrated and separated cell suspension exits the second outlet 384 of the spinning membrane separator 301. If no further washing is required, the control system closes clamp 370 and opens clamp 372. The closing of clamp 370 prevents the washed cell suspension from flowing through the tubing 346 and directs it through tubing 348 to the final product bag 350. The final product container 350 has an input for receiving the separated and washed cell suspension. The final product container 354 is connected to a weight sensor 374. The separation device measures the weight 374 of the container to determine whether the volume of the collected cells in final product container 350 is in the acceptable range and, therefore, whether the washing cycle is complete.

If further washing of the separated cell suspension is desired or required, the control system of separation device closes clamp 372 and clamp 376 and opens clamp 370. The closing of clamp 372 prevents the cell suspension from flowing through the tubing 348 and directs it through tubing 346 to the in-process bag 322. The in-process bag 322 has an inlet for receiving the separated cell suspension. The in-process bag 322 is connected to a weight sensor 378. The control system of the separation device determines the weight as sensed by weight sensor to determine whether enough of separated cell suspension is present in the in-process bag 322 to conduct another wash cycle. If it is determined that enough of the suspension is present, and further washing is desired, the control system of the separator device opens clamp 376 to open and directs the diluted and separated cell suspension through the output of the in-process bag 322, through tubing 320, into branched-connector 318, and through an air detector sensor 380. The air detector sensor 380 detects air in the cell suspension which passes through tubing 324. The control and operation device measures the readings from air detector sensor 380 and determines the further processes to be taken.

The separated cell suspension which includes cells suspended in diluted suspension medium is then passed through the washing process again, as described above. The wash process may be repeated as many times as desired and preferably until the diluted and separated cell suspension has an acceptable remaining concentration of suspension medium. The final diluted and separated cell suspension is collected in the final product bag 350.

Alternatively, rather than repeatedly processing the fluid through a single in-process container, a "batch-type" processing procedure may be followed by using two or more in-process containers 322 (in combination with final product container 350).

The disposable processing set 300 of FIG. 24 is particularly well suited for such "batch-type" processing. In accordance with a cell washing procedure using disposable set 300 of FIG. 24, cells initially separated from the original suspension medium are removed from separator 301 and introduced into one of the in-process containers 322a. Replacement fluid is introduced into container 322a and the cells resuspended. Resuspended cells in container 322a may then be introduced into separator 301 wherein they are separated from the supernatant. Concentrated cells exit through outlet 648 in separator 301 and are introduced into a fresh (second) in-process container 322b. Additional replacement fluid may be introduced into in-process container 322b, and the process repeated, if necessary, with a further fresh (third) in-process container (not shown). The final cell product is then collected in final product container 350, as described above.

In accordance with the "batch-type" cell washing method described above, tubing segments 370a, 370b and 320a, 320b may be associated with clamps (not shown) to control flow to and from multiple in-process containers 322a and 322b. Thus, for example, a clamp on line 370a would be open, while a clamp on line 370b would be closed so that cells exiting separator 301 are directed to (first) in-process container 322a.

For additional washing, cells resuspended in the fresh replacement fluid from container 322a are introduced into separator 301 where the cells are separated from the supernatant, as previously described. The control system of device 400 closes the clamp (not shown in FIG. 24) on tubing segment 370a and opens the clamp (not shown in FIG. 24) on tubing segment 370b to allow cells to flow into fresh (second) in-process container 322b. After the final wash, clamps (not shown) on segments 370a, 370b, etc., are closed and clamp 372 (as shown, for example, in FIG. 23) is opened to allow collection of the final product in container 350.

FIG. 24 shows the front panel 401 of separation device 400; i.e., the hardware, which includes peristaltic pumps 402, 404 and 406. As described above, pump segments 362, 364 and 368 from the disposable set are selectively associated with peristaltic pumps 402, 404, and 406. The peristaltic pumps articulate with the fluid set of FIG. 23 at the pump segments 362, 364 and 368 and advance the cell suspension within the disposable set, as will be understood by those of skill in the art. The control and operation device 400 also includes clamps 410, 412, 414. Clamps 410, 412, 414, and 416 are used to control the flow of the cell suspension through different segments of the disposable set, as described above.

Device 400 also includes several sensors to measure various conditions. The output of the sensors is utilized by device 400 to operate the wash cycle. One or more pressure transducer sensor(s) 426 may be provided on device 400 and may be associated with disposable set 300 at certain points to monitor the pressure during a procedure. Pressure transducer 426 may be integrated into an in-line pressure monitoring site (at, for example, tubing segment 336), to monitor pressure inside separator 301. Air detector 438 sensor may also be associated with the disposable set 300, as necessary. Air detector 438 is optional and may be provided to detect the location of fluid/air interfaces.

Device 400 includes weight scales 440, 442, 444, and 446 from which the final bag, in-process bag, cell suspension bag, and any additional bag, respectively, may depend and be weighed. The weights of the bags are monitored by weight sensors and recorded during a washing procedure. From measurements of the weight sensors, the device determines whether each bag is empty, partially full, or full and controls the components of the control and operation device 200, such as the peristaltic pumps and clamps 410, 412, 414, 416, 418, 420, 422, and 424.

Device 400 includes at least one drive unit or "spinner" 448, which causes the indirect driving of the spinning membrane separator 301. Spinner 448 may consist of a drive motor connected and operated by device 400, coupled to turn an annular magnetic drive member including at least a pair of permanent magnets. As the annular drive member is rotated, magnetic attraction between corresponding magnets within the housing of the spinning membrane separator cause the spinner within the housing of the spinning membrane separator to rotate.

Figure 26:
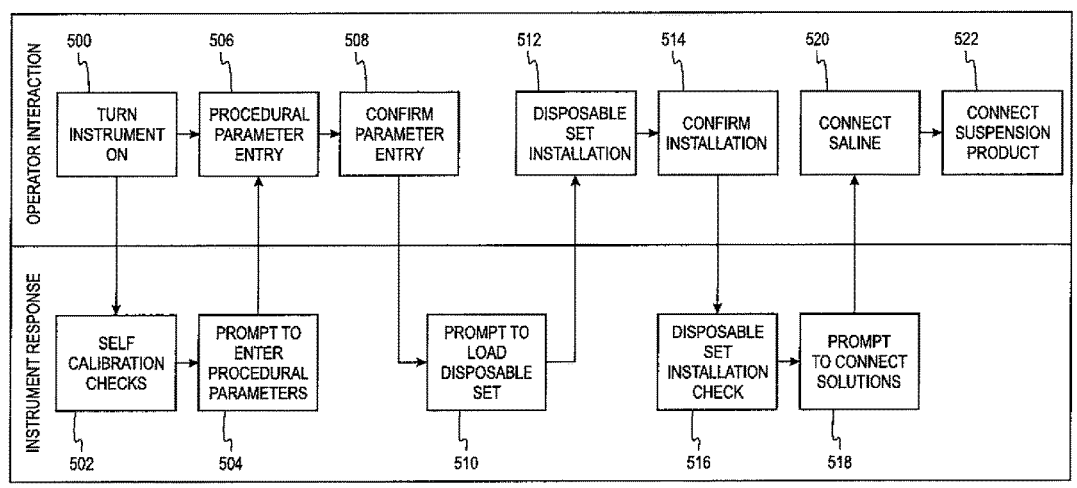
FIGS. 26-28 are flowcharts of the steps in the method cell washing disclosed herein.
Figure 27:
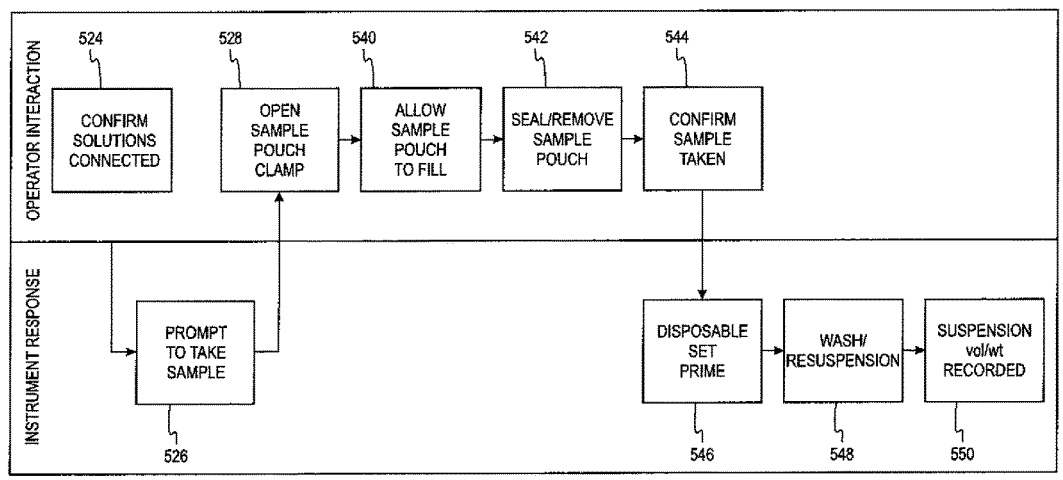
Figure 28:
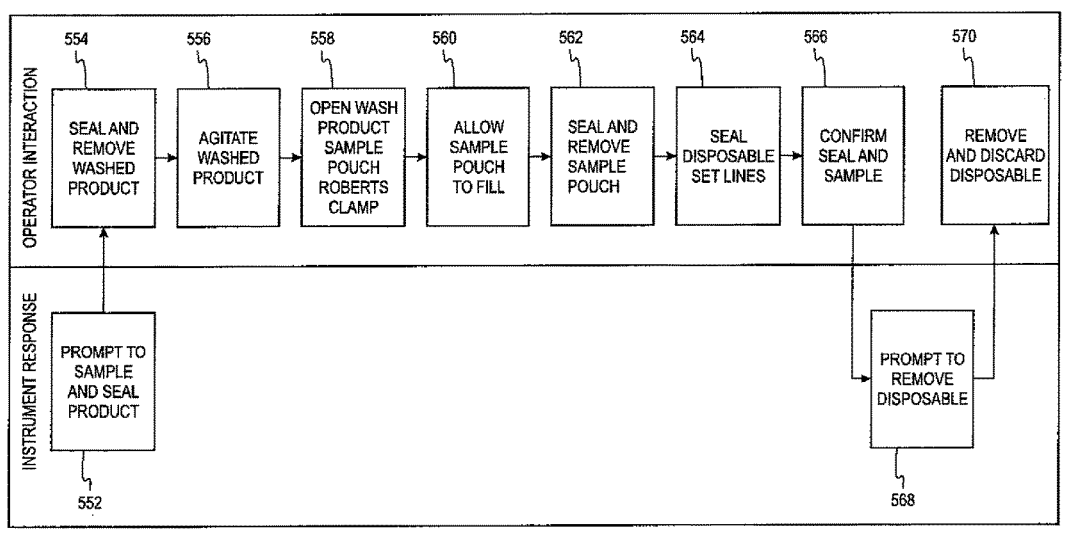

FIGS. 26-28 diagrammatically set forth the method of cell washing as disclosed herein. The steps described below are performed by the software driven microprocessing unit of device 400 with certain steps performed by the operator, as noted. Turning first to FIG. 26, the device is switched on at step 500. The device conducts self-calibration checks 502, including the checking of the peristaltic pumps, clamps, and sensors. Device 400 then prompts the user to enter selected procedural parameters (step 504), such as the washing procedure to be performed, the amount of cell suspension to be washed, the number of washings to take place, etc. The operator may then select and enter the procedural parameters for the wash procedure (step 506).

The device (through the controller) confirms the parameter entry 506 and then prompts the operator to load (step 510) the disposable set. The operator then loads the disposable set (step 512) onto the panel of device 400. After installation of the disposable set, the device confirms installation as shown in (step 514).

After the disposable set is mounted, the device automatically checks to determine whether the disposable set is properly installed (step 516). After the device determines that the disposable set is properly installed, the controller prompts the operator to connect the cell suspension and wash medium (step 518). The operator then connects the wash medium (such as, but not limited to saline) (step 520) to the disposable set via a spike connector, as previously described. The operator then connects the cell suspension within a product bag (step 522) to the disposable set via a spike connector.

As shown in FIG. 27, after the cell suspension and wash medium are connected to the disposable set, the operator confirms that the solutions are connected (step 524). The device prompts the operator to take a cell suspension sample (step 526). The operator or the device then opens sample pouch clamp 528 to introduce fluid into the sample pouch (step 546). Once the sample pouch is filled, it is then sealed and removed (542) from the disposable set. The operator confirms (step 544) that a sample has been taken. Following the removal of the sample pouch, the disposable set is primed (step 546) for the wash process.

The controller of separation device then commences the wash process. The cell suspension to be washed is transferred from its container (e.g., 302 of FIG. 23) through the disposable set to the spinning membrane separator 301. Likewise, the wash medium is transferred from its source, through the disposable set to the spinning membrane separator 301. In a preferred embodiment, the original cells of the cell suspension are concentrated and/or collected in either an in-process bag (for further processing) or collected in a final product bag which is subsequently removed from the disposable set. If (further) washing or diluting of the cell suspension is necessary, the cell suspension in the in-process bag may be washed (a second time) with the same or different wash medium following the process outlined above. Prior to the conclusion of each wash cycle, the cell suspension volume or weight is measured and recorded (step 550). When the concentration of the cells to wash medium reaches an acceptable level the final product bag is filled.

As shown in FIG. 28, once the desired volume of the final product is collected, the control and operation device prompts the operator to sample and seal the final product bag (step 552). A sample pouch is attached to the final product bag. The operator then seals and removes from the disposable set the washed cell suspension in the final product bag (step 552). The final product bag is then agitated (step 556). The operator opens the sample pouch by removing a clamp (step 558). The sample pouch is allowed to fill (step 560). Once the sample bag is filled, the clamp is closed and the sample pouch is sealed and removed (step 562). The operator then seals the disposable set lines (step 564) and confirms that the product bag has been sealed and removed, a sample pouch has been filled and removed, and that the disposable set lines have been sealed (step 566). The control and operation device then prompts the operator to remove the disposable set, as shown in step 568. The operator then removes and discards the disposable set, as shown in step 570.

Thus, an improved spinning membrane separator and methods and systems for using such a spinning membrane are disclosed. The description provided above is intended for illustrative purposes only, and is not intended to limit the scope of the disclosure to any specific method, system, or apparatus or device described herein.

What is claimed:

1. An automated blood collection system for collecting red blood cells comprising:
    a durable hardware component; and
    a disposable fluid flow circuit configured to interface with the durable hardware component, the disposable fluid flow circuit comprising a leukocyte reduction filter for removing leukocytes from red blood cells as the red blood cells pass through the filter, a source of additive solution, a first fluid flow path in communication with a source of red blood cells reduction filter, a second fluid flow path in communication with the source of additive solution, and a third fluid flow path in communication with both the first fluid flow path and the second fluid flow path on a first end of the third fluid flow path and in communication with the leukocyte reduction filter on a second end of the third fluid flow path;
    the durable hardware component further comprising a pump associated with one of the second fluid flow path and the third fluid flow path, and a programmable controller configured to control a flow rate of the additive solution through the disposable fluid flow circuit and to the leukocyte reduction filter, the programmable controller being further configured to flow additive solution to the leukocyte reduction filter at an increasing rate to flush the leukocyte reduction filter of red blood cells that remain in the leukocyte reduction filter after filtration of the red blood cells.

2. The system of claim 1 wherein the programmable controller is further configured to gradually increase the flow rate of additive solution to the leukocyte reduction filter to flush the leukoreduction filter of red blood cells step-wise.

3. The system of claim 1 wherein the programmable controller is further configured to continuously increase the flow rate of additive solution to the leukocyte reduction filter to flush the leukoreduction filter of red blood cells.

4. The system of claim 1 wherein the programmable controller is further configured to increase the flow rate of additive solution to the leukocyte reduction filter to flush the leukoreduction filter of red blood cells depending on one or more of a hematocrit of the red blood cells within the filter, an amount of hemolysis of the red blood cells within the filter and a pressure within the filter.

5. The system of claim 1 wherein the programmable controller is further configured to increase the flow rate of additive solution to the leukocyte reduction filter to flush the leukoreduction filter of red blood cells based on real-time measurements.

6. The system of claim 5 wherein the real-time measurements include one or more measurements of a hematocrit of the red blood cells, an amount of hemolysis of the red blood cells within the filter and a pressure within the filter.

7. The system of claim 1 wherein the pump comprises a variable speed pump.

8. The system of claim 1 wherein the durable hardware component further includes a blood separator comprising a membrane configured to spin about a generally vertically oriented axis within a housing.

9. The system of claim 1 wherein the additive solution comprises a low-viscosity non-biological fluid.

10. The system of claim 1 wherein the additive solution comprises a preservative solution.

11. The system of claim 1 wherein the programmable controller is further configured to increase the flow rate of additive solution to the leukocyte reduction filter to flush the leukoreduction filter of red blood cells according to an additive solution flush rate ramp-up schedule based on a first correlation between hematocrit and hemolysis at selected additive solution flush rates through the leukoreduction filter and a second correlation between hematocrit decay and time at the selected additive solution flush rates through the leukoreduction filter.

* * * * *